US012690883B2

(12) United States Patent
Lazzari et al.

(10) Patent No.: US 12,690,883 B2
(45) Date of Patent: Jul. 28, 2026

(54) SURGICAL CUTTING INSTRUMENT FOR ROBOTIC SURGERY AND METHOD

(71) Applicant: MEDICAL MICROINSTRUMENTS, INC., Wilmington, DE (US)

(72) Inventors: Giorgio Lazzari, Pisa (IT); Massimiliano Simi, Pisa (IT)

(73) Assignee: MEDICAL MICROINSTRUMENTS, INC., Wilmington, DE (US)

( * ) Notice: Subject to any disclaimer, the term of this patent is extended or adjusted under 35 U.S.C. 154(b) by 192 days.

(21) Appl. No.: 18/570,527

(22) PCT Filed: Jun. 16, 2022

(86) PCT No.: PCT/IB2022/055601
§ 371 (c)(1),
(2) Date: Dec. 14, 2023

(87) PCT Pub. No.: WO2022/269424
PCT Pub. Date: Dec. 29, 2022

(65) Prior Publication Data
US 2024/0268855 A1     Aug. 15, 2024

(30) Foreign Application Priority Data
Jun. 21, 2021     (IT) ......................... 102021000016199

(51) Int. Cl.
*A61B 17/3201*     (2006.01)
*A61B 17/00*     (2006.01)
(Continued)

(52) U.S. Cl.
CPC ........ *A61B 17/3201* (2013.01); *A61B 17/285* (2013.01); *A61B 17/295* (2013.01);
(Continued)

(58) Field of Classification Search
CPC ..... A61B 17/285; A61B 17/29; A61B 17/295; A61B 17/3201; A61B 2017/00017;
(Continued)

(56) References Cited

U.S. PATENT DOCUMENTS

| | | | |
|---|---|---|---|
| 6,063,095 A | 5/2000 | Wang et al. | |
| 6,364,888 B1 | 4/2002 | Niemeyer et al. | |

(Continued)

FOREIGN PATENT DOCUMENTS

| | | |
|---|---|---|
| DE | 102010009065 A1 | 8/2011 |
| DE | 102014006264 A1 | 11/2015 |

(Continued)

OTHER PUBLICATIONS

International Search Report and Written Opinion issued for International Patent Appl. No. PCT/IB2022/055601 mailed Sep. 22, 2022, 16 pgs.

*Primary Examiner* — Mohamed G Gabr
*Assistant Examiner* — Khoa Tan Le
(74) *Attorney, Agent, or Firm* — Merchant & Gould P.C.

(57) ABSTRACT

A surgical cutting instrument including a connection link connected to the distal end of a shaft having a body including integral convex ruled surfaces of connection, a first distal connecting portion; a support link articulated to the connection link and having convex ruled surfaces. A proximal connecting portion articulated to the first connection link defines a proximal rotational joint. A second distal connecting portion includes a blade holder link articulated to the support link. A blade holder link attachment root has a pulley portion, a drag portion, a blade link, a bendable cutting edge and a drag counter-portion. A reaction link articulates to the support link and to the blade/blade holder link, having a body including a pulley portion formed by convex ruled surfaces of the reaction link root. First and
(Continued)

second distances between the first and second termination seats of the root are constant for any cutting condition.

11 Claims, 24 Drawing Sheets

(51) Int. Cl.

| | |
|---|---|
| A61B 17/285 | (2006.01) |
| A61B 17/29 | (2006.01) |
| A61B 17/295 | (2006.01) |
| A61B 17/32 | (2006.01) |
| A61B 34/35 | (2016.01) |
| A61B 34/37 | (2016.01) |

(52) U.S. Cl.
CPC .............. *A61B 34/35* (2016.02); *A61B 34/37* (2016.02); *A61B 2017/00017* (2013.01); *A61B 2017/00353* (2013.01); *A61B 2017/00367* (2013.01); *A61B 2017/2908* (2013.01); *A61B 2017/320075* (2017.08)

(58) Field of Classification Search
CPC ........... A61B 2017/00353; A61B 2017/00367; A61B 2017/2908; A61B 2017/2947; A61B 2017/320075; A61B 2034/306; A61B 34/35; A61B 34/37; A61B 34/71
See application file for complete search history.

(56) References Cited

U.S. PATENT DOCUMENTS

| | | | |
|---|---|---|---|
| 6,424,885 B1 | 7/2002 | Niemeyer et al. |
| 6,459,926 B1 | 10/2002 | Nowlin et al. |
| 6,594,552 B1 | 7/2003 | Nowlin et al. |
| 6,671,581 B2 | 12/2003 | Niemeyer et al. |
| 6,766,204 B2 | 7/2004 | Niemeyer et al. |
| 6,879,880 B2 | 4/2005 | Nowlin et al. |
| 7,087,049 B2 | 8/2006 | Nowlin et al. |
| 7,155,315 B2 | 12/2006 | Niemeyer |
| 7,331,967 B2 | 2/2008 | Lee et al. |
| 7,373,219 B2 | 5/2008 | Nowlin et al. |
| 7,778,733 B2 | 8/2010 | Nowlin et al. |
| 7,806,891 B2 | 10/2010 | Nowlin et al. |
| 7,886,743 B2 | 2/2011 | Cooper et al. |
| 7,947,050 B2 | 5/2011 | Lee et al. |
| 7,967,137 B2 | 6/2011 | Fulbrook et al. |
| 8,004,229 B2 | 8/2011 | Nowlin et al. |
| 8,005,571 B2 | 8/2011 | Sutherland et al. |
| 8,123,740 B2 | 2/2012 | Madhani et al. |
| 8,220,468 B2 | 7/2012 | Cooper et al. |
| 8,281,670 B2 | 10/2012 | Larkin et al. |
| 8,368,649 B2 | 2/2013 | Hall |
| 8,375,808 B2 | 2/2013 | Blumenkranz et al. |
| 8,521,331 B2 | 8/2013 | Itkowitz |
| 8,540,748 B2 | 9/2013 | Murphy et al. |
| 8,620,473 B2 | 12/2013 | Diolaiti et al. |
| 8,677,820 B2 | 3/2014 | Nakagawa et al. |
| 8,812,160 B2 | 8/2014 | Hagn et al. |
| 8,831,782 B2 | 9/2014 | Itkowitz |
| 8,935,003 B2 | 1/2015 | Itkowitz et al. |
| 8,939,963 B2 | 1/2015 | Rogers et al. |
| 8,996,173 B2 | 3/2015 | Itkowitz et al. |
| 9,060,796 B2 | 6/2015 | Seo |
| 9,101,379 B2 | 8/2015 | Au et al. |
| 9,333,042 B2 | 5/2016 | Diolaiti et al. |
| 9,408,668 B2 | 8/2016 | Durant et al. |
| 9,452,020 B2 | 9/2016 | Griffiths et al. |
| 9,492,927 B2 | 11/2016 | Diolaiti et al. |
| 9,554,866 B2 | 1/2017 | Cunningham et al. |
| 9,629,680 B2 | 4/2017 | Winer |
| 9,632,573 B2 | 4/2017 | Ogawa et al. |
| 9,743,989 B2 | 8/2017 | Itkowitz et al. |
| 9,770,300 B2 | 9/2017 | Kwon et al. |
| 9,901,402 B2 | 2/2018 | Itkowitz et al. |
| 9,949,799 B2 | 4/2018 | Hingwe et al. |
| 9,968,405 B2 | 5/2018 | Cooper et al. |
| 10,013,082 B2 | 7/2018 | Schecter |
| 10,034,718 B2 | 7/2018 | Griffiths et al. |
| 10,052,164 B2 | 8/2018 | Overmyer |
| 10,085,810 B2 | 10/2018 | Vakharia et al. |
| 10,123,844 B2 | 11/2018 | Nowlin et al. |
| 10,188,472 B2 | 1/2019 | Diolaiti et al. |
| 10,219,870 B2 | 3/2019 | Mondry et al. |
| 10,219,898 B2 | 3/2019 | Forsell |
| 10,271,915 B2 | 4/2019 | Diolaiti et al. |
| 10,292,661 B1 | 5/2019 | LaBorde |
| 10,299,873 B2 | 5/2019 | Hares et al. |
| 10,299,883 B2 | 5/2019 | Kilroy et al. |
| 10,307,199 B2 | 6/2019 | Farritor et al. |
| 10,321,964 B2 | 6/2019 | Grover et al. |
| 10,357,320 B2 | 7/2019 | Beira |
| 10,357,324 B2 | 7/2019 | Flatt et al. |
| 10,376,323 B2 | 8/2019 | Farritor et al. |
| 10,376,337 B2 | 8/2019 | Kilroy et al. |
| 10,383,699 B2 | 8/2019 | Kilroy et al. |
| 10,393,109 B2 | 8/2019 | Wu et al. |
| 10,413,374 B2 | 9/2019 | Chassot et al. |
| 10,420,618 B2 | 9/2019 | Grover et al. |
| 10,470,830 B2 | 11/2019 | Hill et al. |
| 10,485,621 B2 | 11/2019 | Morrissette et al. |
| 10,512,514 B2 | 12/2019 | Nowlin et al. |
| 10,512,515 B2 | 12/2019 | Bailey |
| 10,524,871 B2 | 1/2020 | Liao |
| 10,531,929 B2 | 1/2020 | Widenhouse et al. |
| 10,543,050 B2 | 1/2020 | Itkowitz et al. |
| 10,561,468 B2 | 2/2020 | Cunningham et al. |
| 10,568,703 B2 | 2/2020 | Nobles et al. |
| 10,568,704 B2 | 2/2020 | Savall et al. |
| 10,582,975 B2 | 3/2020 | Simi |
| 10,603,123 B2 | 3/2020 | Vakharia et al. |
| 10,617,484 B2 | 4/2020 | Kilroy et al. |
| 10,624,708 B2 | 4/2020 | Hunter |
| 10,639,114 B2 | 5/2020 | Schuh et al. |
| 10,653,489 B2 | 5/2020 | Kopp |
| 10,661,453 B2 | 5/2020 | Koenig et al. |
| 10,736,701 B2 | 8/2020 | Savall et al. |
| 10,736,706 B2 | 8/2020 | Scheib |
| 10,751,136 B2 | 8/2020 | Farritor et al. |
| 10,758,298 B2 | 9/2020 | Felder et al. |
| 10,779,898 B2 | 9/2020 | Hill et al. |
| 10,786,327 B2 | 9/2020 | Anderson et al. |
| 10,789,329 B2 | 9/2020 | Lanting |
| 10,813,713 B2 | 10/2020 | Koch, Jr. et al. |
| 10,820,953 B2 | 11/2020 | Kralicky et al. |
| 10,842,577 B2 | 11/2020 | Kilroy et al. |
| 10,842,581 B2 | 11/2020 | Bailey |
| 10,864,051 B2 | 12/2020 | Simi |
| 10,881,477 B1 | 1/2021 | Genova et al. |
| 10,888,390 B2 | 1/2021 | Higuchi et al. |
| 10,898,281 B2 | 1/2021 | Cooper et al. |
| 10,912,618 B2 | 2/2021 | Vakharia et al. |
| 10,959,798 B2 | 3/2021 | Diolaiti et al. |
| 10,987,192 B2 | 4/2021 | Garcia Kilroy et al. |
| 11,037,464 B2 | 6/2021 | Ho et al. |
| 11,045,268 B2 | 6/2021 | Grover et al. |
| 11,083,532 B2 | 8/2021 | Liao |
| 11,083,534 B2 | 8/2021 | Hares |
| 11,096,746 B2 | 8/2021 | Savall et al. |
| 11,109,925 B2 | 9/2021 | Cooper et al. |
| 11,135,031 B2 | 10/2021 | Savall et al. |
| 11,172,997 B2 | 11/2021 | Kostrzewski et al. |
| 11,179,209 B2 | 11/2021 | Kralicky et al. |
| 11,179,211 B2 | 11/2021 | Zemlok et al. |
| 11,213,364 B2 | 1/2022 | Popovic |
| 11,246,670 B2 | 2/2022 | Swayze et al. |
| 11,266,469 B2 | 3/2022 | Fuerst et al. |
| 11,284,957 B2 | 3/2022 | Denlinger et al. |
| 11,284,959 B2 | 3/2022 | Bailey |
| 11,344,374 B2 | 5/2022 | Tekiela et al. |
| 11,357,597 B2 | 6/2022 | Jhaveri et al. |
| 11,399,908 B2 | 8/2022 | Diolaiti et al. |
| 11,406,465 B2 | 8/2022 | Zemlok et al. |

(56)  References Cited

U.S. PATENT DOCUMENTS

| | | |
|---|---|---|
| 11,417,928 B2 | 8/2022 | Cheng |
| 11,439,478 B2 | 9/2022 | Anderson et al. |
| 11,446,097 B2 | 9/2022 | Savall et al. |
| 11,457,987 B2 | 10/2022 | He et al. |
| 11,478,318 B2 | 10/2022 | Cone et al. |
| 11,484,379 B2 | 11/2022 | Sutherland et al. |
| 11,504,197 B1 | 11/2022 | Noonan et al. |
| 11,504,203 B2 | 11/2022 | Flatt et al. |
| 11,534,246 B2 | 12/2022 | Fuerst et al. |
| 11,534,252 B2 | 12/2022 | DiMaio et al. |
| 11,576,733 B2 | 2/2023 | Anglese |
| 11,607,279 B2 | 3/2023 | Chaplin |
| 11,666,401 B2 | 6/2023 | Denlinger et al. |
| 11,684,434 B2 | 6/2023 | Shelton, IV |
| 2002/0055795 A1 | 5/2002 | Niemeyer et al. |
| 2002/0128552 A1 | 9/2002 | Nowlin et al. |
| 2003/0004610 A1 | 1/2003 | Niemeyer et al. |
| 2003/0195664 A1 | 10/2003 | Nowlin et al. |
| 2004/0039485 A1 | 2/2004 | Niemeyer et al. |
| 2005/0194507 A1 | 9/2005 | White |
| 2006/0030840 A1 | 2/2006 | Nowlin et al. |
| 2006/0106493 A1 | 5/2006 | Niemeyer et al. |
| 2006/0241414 A1 | 10/2006 | Nowlin et al. |
| 2008/0119870 A1 | 5/2008 | Williams |
| 2008/0154246 A1 | 6/2008 | Nowlin et al. |
| 2009/0301927 A1 | 12/2009 | Fvlbrook et al. |
| 2010/0053085 A1 | 3/2010 | Hall |
| 2010/0274087 A1 | 10/2010 | Diolaiti et al. |
| 2011/0118748 A1 | 5/2011 | Itkowitz |
| 2012/0011932 A1 | 1/2012 | Nakagawa et al. |
| 2012/0059391 A1 | 3/2012 | Diolaiti et al. |
| 2012/0071891 A1 | 3/2012 | Itkowitz et al. |
| 2012/0071892 A1 | 3/2012 | Itkowitz et al. |
| 2013/0035697 A1 | 2/2013 | Ogawa et al. |
| 2013/0316681 A1 | 11/2013 | Huang et al. |
| 2013/0321262 A1 | 12/2013 | Schecter |
| 2014/0018960 A1 | 1/2014 | Itkowitz |
| 2014/0222021 A1 | 8/2014 | Diolaiti et al. |
| 2015/0025549 A1 | 1/2015 | Kilroy et al. |
| 2015/0038981 A1 | 2/2015 | Kilroy et al. |
| 2015/0038982 A1 | 2/2015 | Kilroy et al. |
| 2015/0066051 A1 | 3/2015 | Kwon et al. |
| 2015/0080909 A1 | 3/2015 | Itkowitz et al. |
| 2015/0157410 A1 | 6/2015 | Kilroy et al. |
| 2015/0182289 A1 | 7/2015 | Itkowitz et al. |
| 2016/0242860 A1 | 8/2016 | Diolaiti et al. |
| 2017/0035521 A1 | 2/2017 | Diolaiti et al. |
| 2017/0095295 A1 | 4/2017 | Overmyer |
| 2017/0095298 A1 | 4/2017 | Vakharia et al. |
| 2017/0224428 A1 | 8/2017 | Kopp |
| 2017/0252112 A1 | 9/2017 | Crawford et al. |
| 2017/0265949 A1 | 9/2017 | Crawford et al. |
| 2017/0312043 A1 | 11/2017 | Ogawa et al. |
| 2017/0319284 A1 | 11/2017 | Itkowitz et al. |
| 2018/0025666 A1 | 1/2018 | Ho et al. |
| 2018/0036088 A1 | 2/2018 | Kilroy et al. |
| 2018/0078034 A1 | 3/2018 | Savall et al. |
| 2018/0078319 A1 | 3/2018 | Nobles et al. |
| 2018/0078321 A1 | 3/2018 | Liao |
| 2018/0092706 A1 | 4/2018 | Anderson et al. |
| 2018/0161108 A1 | 6/2018 | Savall et al. |
| 2018/0168759 A1 | 6/2018 | Kilroy et al. |
| 2018/0250085 A1* | 9/2018 | Simi ........................ B25J 9/104 |
| 2019/0012006 A1 | 1/2019 | Schecter |
| 2019/0029770 A1 | 1/2019 | Bailey |
| 2019/0069960 A1 | 3/2019 | Vakharia et al. |
| 2019/0105032 A1* | 4/2019 | Crews ................ A61B 17/0469 |
| 2019/0110847 A1 | 4/2019 | Diolaiti et al. |
| 2019/0201152 A1 | 7/2019 | Diolaiti et al. |
| 2019/0239972 A1 | 8/2019 | Chassot et al. |
| 2019/0307524 A1 | 10/2019 | Popovic |
| 2019/0314097 A1 | 10/2019 | Diolaiti |
| 2019/0343594 A1 | 11/2019 | Garcia Kilroy et al. |
| 2019/0380791 A1 | 12/2019 | Fuerst et al. |
| 2019/0380802 A1 | 12/2019 | Savall et al. |
| 2019/0380809 A1 | 12/2019 | Fuerst et al. |
| 2020/0008901 A1 | 1/2020 | Garcia Kilroy et al. |
| 2020/0022775 A1 | 1/2020 | Garcia Kilroy et al. |
| 2020/0046439 A1 | 2/2020 | Tekiela et al. |
| 2020/0046450 A1 | 2/2020 | Tsao et al. |
| 2020/0069388 A1 | 3/2020 | Bailey |
| 2020/0085522 A1 | 3/2020 | Liao |
| 2020/0107894 A1 | 4/2020 | Wallace |
| 2020/0113641 A1 | 4/2020 | Itkowitz et al. |
| 2020/0138534 A1 | 5/2020 | Garcia Kilroy et al. |
| 2020/0170726 A1 | 6/2020 | Simi |
| 2020/0170727 A1 | 6/2020 | Simi |
| 2020/0197112 A1 | 6/2020 | Chin et al. |
| 2020/0197115 A1 | 6/2020 | Vakharia et al. |
| 2020/0205922 A1 | 7/2020 | Cone et al. |
| 2020/0214773 A1 | 7/2020 | Nobles et al. |
| 2020/0214779 A1 | 7/2020 | Masuda et al. |
| 2020/0222134 A1 | 7/2020 | Savall et al. |
| 2020/0289212 A1 | 9/2020 | Savall et al. |
| 2020/0289223 A1 | 9/2020 | Denlinger et al. |
| 2020/0330170 A1 | 10/2020 | Farritor et al. |
| 2020/0360097 A1 | 11/2020 | DiMaio et al. |
| 2020/0390507 A1 | 12/2020 | Sadaka |
| 2020/0390510 A1 | 12/2020 | Thompson et al. |
| 2020/0397517 A1 | 12/2020 | Unsworth |
| 2020/0397529 A1 | 12/2020 | Anderson et al. |
| 2020/0405408 A1 | 12/2020 | Shelton, IV et al. |
| 2020/0405434 A1 | 12/2020 | Schuh et al. |
| 2021/0030495 A1 | 2/2021 | Savall et al. |
| 2021/0052338 A1 | 2/2021 | Hill et al. |
| 2021/0052341 A1 | 2/2021 | Bailey |
| 2021/0059776 A1 | 3/2021 | Simi |
| 2021/0059781 A1 | 3/2021 | Peine et al. |
| 2021/0085301 A1 | 3/2021 | Au et al. |
| 2021/0106393 A1 | 4/2021 | Simi |
| 2021/0121260 A1 | 4/2021 | Genova et al. |
| 2021/0153964 A1 | 5/2021 | Diolaiti et al. |
| 2021/0153965 A1 | 5/2021 | Lau et al. |
| 2021/0153966 A1 | 5/2021 | Lau et al. |
| 2021/0196411 A1 | 7/2021 | Vakharia et al. |
| 2021/0196413 A1 | 7/2021 | Inoue |
| 2021/0197401 A1 | 7/2021 | Weintraub et al. |
| 2021/0290326 A1 | 9/2021 | Diolaiti et al. |
| 2021/0290328 A1 | 9/2021 | Miller et al. |
| 2021/0304639 A1 | 9/2021 | Ho et al. |
| 2021/0322117 A1 | 10/2021 | Liao |
| 2021/0322119 A1 | 10/2021 | Hares |
| 2021/0353381 A1 | 11/2021 | Usui et al. |
| 2021/0369365 A1 | 12/2021 | Goswami et al. |
| 2022/0015839 A1 | 1/2022 | Savall et al. |
| 2022/0015852 A1 | 1/2022 | Savall et al. |
| 2022/0031415 A1 | 2/2022 | Vargas et al. |
| 2022/0047345 A1 | 2/2022 | Choi et al. |
| 2022/0096189 A1 | 3/2022 | Popovic |
| 2022/0184823 A1 | 6/2022 | Bonny et al. |
| 2022/0192763 A1 | 6/2022 | Fuerst et al. |
| 2022/0211452 A1 | 7/2022 | Clark et al. |
| 2022/0218418 A1 | 7/2022 | Jolaeimoghaddam et al. |
| 2022/0226056 A1 | 7/2022 | Beckman et al. |
| 2022/0265380 A1 | 8/2022 | Bailey |
| 2022/0361736 A1 | 11/2022 | Danna et al. |
| 2022/0361970 A1 | 11/2022 | Griffiths et al. |
| 2022/0370163 A1 | 11/2022 | Schuh et al. |
| 2022/0378526 A1 | 12/2022 | Balicki et al. |
| 2022/0378527 A1 | 12/2022 | Basafa et al. |
| 2022/0378533 A1 | 12/2022 | McDiarmid et al. |
| 2022/0387131 A1 | 12/2022 | Anderson et al. |
| 2022/0395346 A1 | 12/2022 | Ihara et al. |
| 2022/0401162 A1 | 12/2022 | Unsworth |
| 2023/0028689 A1 | 1/2023 | Rabindran et al. |
| 2023/0045591 A1 | 2/2023 | de la Fuente Klein et al. |
| 2023/0149105 A1 | 5/2023 | Thornycroft et al. |

FOREIGN PATENT DOCUMENTS

| | | |
|---|---|---|
| EP | 2845556 A1 | 3/2015 |
| EP | 3245975 A1 | 11/2017 |
| EP | 3424651 A1 | 1/2019 |
| EP | 3459429 A1 | 3/2019 |

(56) References Cited

FOREIGN PATENT DOCUMENTS

| | | | |
|---|---|---|---|
| EP | 3574860 | A1 | 12/2019 |
| EP | 3586780 | A1 | 1/2020 |
| EP | 3852668 | A1 | 7/2021 |
| WO | 2013071071 | A1 | 5/2013 |
| WO | 2014151621 | A1 | 9/2014 |
| WO | 2016053657 | A1 | 4/2016 |
| WO | 2016171757 | A1 | 10/2016 |
| WO | 2016201207 | A1 | 12/2016 |
| WO | 2017-064301 | A1 | 4/2017 |
| WO | 2017-064303 | A1 | 4/2017 |
| WO | 2017-064306 | A1 | 4/2017 |
| WO | 2017094844 | A1 | 6/2017 |
| WO | 2018104252 | A1 | 6/2018 |
| WO | 2018107062 | A1 | 6/2018 |
| WO | 2018-189721 | A1 | 10/2018 |
| WO | 2018-189722 | A1 | 10/2018 |
| WO | 2018-189729 | A1 | 10/2018 |
| WO | 2019050878 | A2 | 3/2019 |
| WO | 2019099584 | A1 | 5/2019 |
| WO | 2019103954 | A1 | 5/2019 |
| WO | 2019-173266 | A1 | 9/2019 |
| WO | 2019-220407 | A1 | 11/2019 |
| WO | 2019-220408 | A1 | 11/2019 |
| WO | 2019-220409 | A1 | 11/2019 |
| WO | 2019240825 | A1 | 12/2019 |
| WO | 2020139405 | A1 | 7/2020 |
| WO | 2020153411 | A1 | 7/2020 |
| WO | 2021141920 | A1 | 7/2021 |
| WO | 2021188127 | A1 | 9/2021 |
| WO | 2022155067 | A1 | 7/2022 |

* cited by examiner

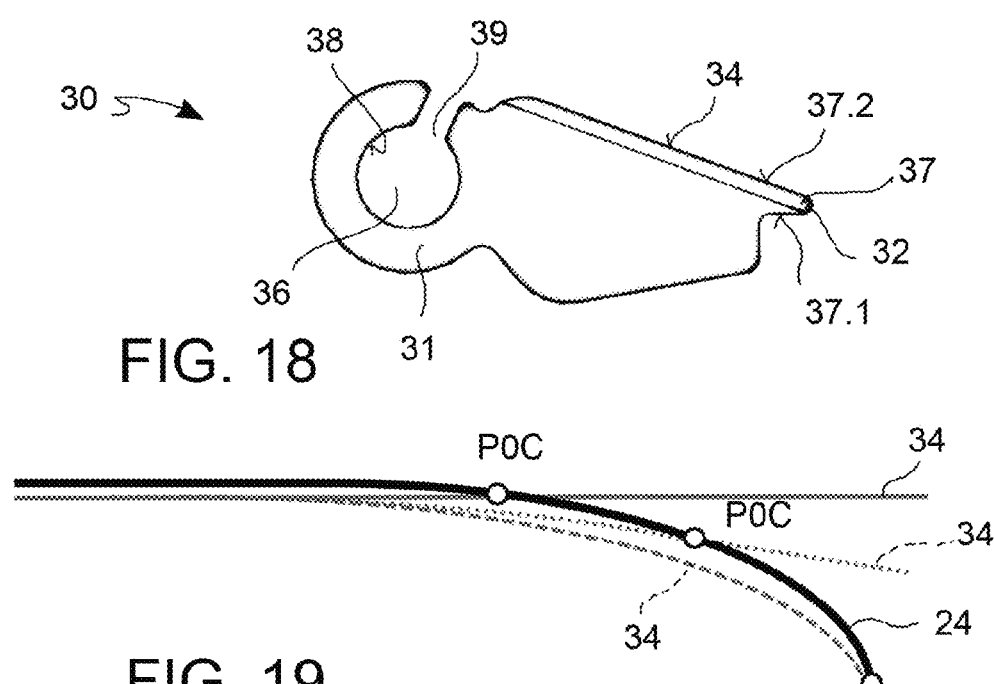
FIG. 18
FIG. 19
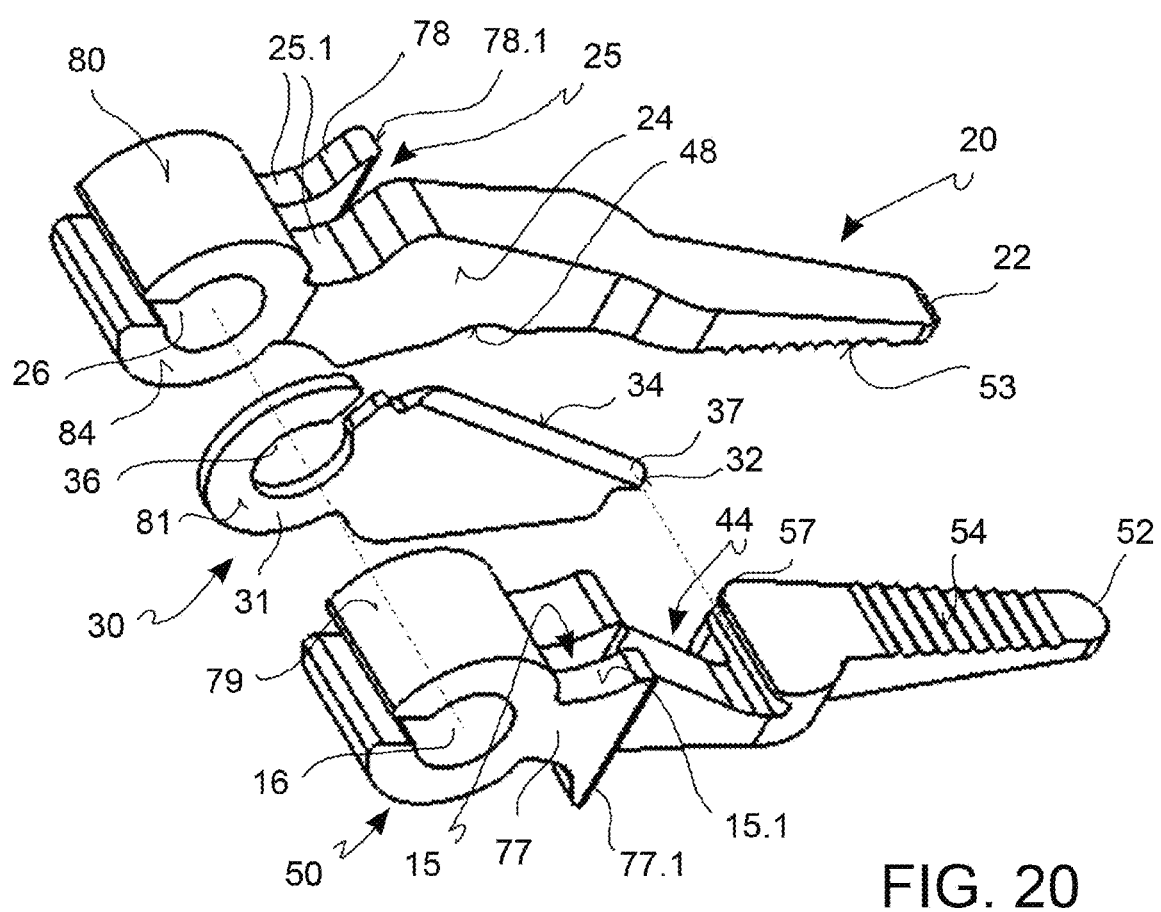
FIG. 20

SURGICAL CUTTING INSTRUMENT FOR ROBOTIC SURGERY AND METHOD

CROSS-REFERENCE TO RELATED APPLICATIONS

This application is a National Stage Application of PCT/IB2022/055601, filed Jun. 16, 2022, which claims benefit of priority to application No. 102021000016199, filed Jun. 21, 2021 in Italy, and which applications are incorporated herein by reference. To the extent appropriate, a claim of priority is made to each of the above-disclosed applications.

FIELD OF THE INVENTION

The present invention relates to a surgical instrument.

In particular, the present invention relates to a surgical instrument adapted to perform a cutting action.

A surgical cutting instrument according to the present invention is particularly suitable for robotic surgery.

The present invention further relates to a rotational joint of a surgical cutting instrument.

Furthermore, the present invention relates to a method.

Background Art

Robotic surgery apparatuses are generally known in the art and typically comprise a central robotic tower (or cart) and one or more robotic arms extending from the central robotic tower. Each arm comprises a motorized positioning system (or manipulator) for moving a surgical instrument distally attachable thereto, in order to perform surgical procedures on a patient. The patient typically lies on an operating bed located in the operating room, in which sterility is ensured to avoid bacterial contamination due to non-sterile parts of the robotic apparatus.

In the context of traditional, i.e., non-robotic, surgery, instruments of the needle-driver/sutures-cutter type are generally known, which typically comprise at the opposite end of the maneuvering rings a needle-driver/sutures-cutter formed by the two free ends having gripping surfaces for the surgical needle and blades for cutting the suture. In some cases, the blades are made in a seat or recess made in the body of the gripper that is accessible through a distinct and separate access opening with respect to the opening for accessing the gripping surfaces for the needle.

Surgical scissors are also known in the field, which comprise at the opposite end of the operating rings two opposite blades on the free ends. A spring can be provided for the maneuvering rings. Typically, the opening angle of the free ends useful to perform the cutting action in such traditional surgical scissors must be less than 25°.

Furthermore, in the field of robotic surgery, end-effector solutions of the needle-driver/sutures-cutter type for laparoscopy have been suggested, having opposite gripping surfaces and respective blades placed at the distal end of an elongated rod or an elongated shaft. Typically, the blade is co-molded with the respective gripping surface for the needle forming a cantilevered protrusion with respect to the gripping surface and placed proximally thereto, i.e., between the gripping surface and the pivot hinge of the gripping surfaces. Usually the blade wire is made in a second sharpening process performed for each individual piece. Therefore, a single molded piece usually comprises a root for forming a part of the hinge, a free end, a gripping surface and a blade which extends with respect to the gripping surface in the closing direction towards the opposite and faceable other blade of the end-effector of the needle-driver/sutures-cutter type.

Scissor-type end-effector solutions for robotic surgery have also been suggested, in which each free end of the end-effector is provided with a blade, as for example shown in US 2008/0119870.

Both in the surgical instruments for robotic surgery of the needle-driver/sutures-cutter type, and in those of the scissor type, a plurality of elastic washers of the "Belleville washer" type ensure a preload between the roots of the two pieces forming the end-effector to determine in closing a mechanical interference condition between the blades aimed at making the cut. Therefore, when the end-effector closes, the opposite blades enter interference and cause a transverse sliding away between the respective roots, counteracting the elastic influence action exerted by said elastic Belleville washers to the hinge.

Otherwise, US-2019/0105032 shows a cutting end-effector, in which the blades each comprise in a single piece an elastic cantilevered tab, said two elastic cantilevered tabs extending in a direction parallel to the pin towards each other, so that the elastic preload is given by the contact between the two cantilevered tabs. Thereby, assembling Belleville-type elastic washers on the hinge is avoided, thus allowing an axial space to be left at the hinge between the two blades to accommodate the sliding thereof relative to the variation of the elastic reaction exerted by the cantilevered elastic tabs thereof in mutual contact.

Another known example is given by US-2020-0107894 which shows a needle-driver/suture-cutter solution in which the blade is housed in a longitudinal pocket of the gripping link and is rotatable independently with respect thereto, so that it can be extracted if necessary.

Alternatively or in addition to the plurality of washers of the "Belleville washer" type, an adjustment screw can be provided at the hinge in order to adjust the cutting interference between the blades, usually forming the articulation pin itself. If the adjustment screw is provided in combination with the plurality of elastic washers of the "Belleville washer" type, it works by counteracting the elastic action of the springs to allow an end of adjustment in elastic preload.

Typically, the known surgical scissors attributable to the types described above have two blades both curved axially in the same direction to ensure a mutual contact of cutting interference which are adjusted so that they are capable of satisfactorily cutting only for small opening angles, for example not exceeding 20°, i.e., the blades cut well only close to or at the distal free end where the axial curvature (i.e., in the direction of the hinge axis) is more accentuated, while in the respective proximal sections thereof they are axially spaced apart and thus unsuitable for performing a precise cut (the tissue to be cut bends between the blades without separating). Conversely, if the blades are adjusted to be in mechanical cutting interference contact in the proximal portions thereof, i.e., for high opening angles, for example greater than 15°, they will be unsuitable for completely closing because the distal curvature thereof will in fact create closing stroke ends precluding the cutting capacity for small opening angles. Strongly increasing the tightening force of the blades, they could close but would necessarily axially distance themselves again in the proximal section thereof, losing the cutting capacity in the proximal area. For these reasons it is usually chosen to tighten the adjustment screws of the blades of the known surgical scissors so that a mechanical interference condition can be reached only close to the free ends, as they are easier to view and require a lower degree of opening, thus a smaller footprint.

The miniaturization of surgical instruments and in particular of the ends or end-effectors thereof for robotic surgery is particularly desirable because it opens up advantageous scenarios of accessibility in complex areas and potentially of minimal invasiveness for the patient undergoing surgery.

The known solutions of the type mentioned above are totally unsuitable for a boosted miniaturization because they would impose impossible processes for the production of the pieces as well as complicated assembly strategies of the pieces to obtain the assembled end-effector. For example, consider the need to assemble micro-parts to the hinge while counteracting the elastic reaction of Belleville-type elastic washers, as well as the objective extreme difficulty of manufacturing by co-molding micro-ridges and micro-undercuts which must be sufficiently robust to withstand rather high stresses when in operation and at the same time geometrically shaped to minimize frictions. In fact, as is well known, at the micro-scale surface forces such as friction are dominant over volume forces.

Furthermore, in surgical instruments having cutting end-effectors actuated by actuation cables or tendons, to ensure a high closing force such as to exert a precise cutting action without damaging the actuation tendons it is typically, necessary to make a reducer, i.e., a pulley of relatively large diameter, but this limits the miniaturization of the pieces especially close to the distal end of the end-effector. Otherwise, to maintain the size of the end-effector compact, it would be necessary to increase the tensile strength of the actuation tendons at the expense of the longitudinal bendability thereof and thus in any case imposing a distal pulley of relatively large diameter; or an attempt could be made to reinforce the tendons by increasing the diameter thereof, but as is apparent to those skilled in the art, both of these choices would be an obstacle severely hindering miniaturization.

Furthermore, as the scale decreases, it becomes increasingly complex to precisely size elements intended to form when rotational joints are assembled, such as end-effector gripping terminals of a surgical instrument, because small machining uncertainties at the level of the fulcrum, i.e., the hinge, impose enormous inaccuracies close to the respective cantilevered free ends and therefore at the cutting blades in the case of scissor-type instruments or at the gripping surfaces in the case of tools such as needle-driver/sutures-cutters.

Similarly, therefore, in an attempt to transmit a high closing force such as to exert a precise cutting action without damaging the actuation tendons, the provision of linkages associated with the blades (a solution in itself known in the art) would also be an obstacle to miniaturization, even for the sole objective difficulty of making the pieces on such a reduced scale that they simultaneously prove robust when in working conditions, as well as for the footprint in the area proximal to the common rotation axis of the free ends, as well as for the difficulty of assembly.

The end-effector portions which are placed distally with respect to the hinge, whether only the cutting blades or the cutting blades and gripping surfaces, are typically designed to perform extremely precise tasks and at the same time the cutting blades must ensure a precise and clean cutting action.

U.S. Ser. No. 10/864,051, WO-2017-064301, WO-2019-220407, WO-2019-220408, WO-2019-220409 and US-2021-059776 to the same Applicant disclose teleoperated robotic surgery systems having one or more surgical instruments controlled by one or more master interfaces.

Furthermore, U.S. Ser. No. 10/582,975, EP-3586780, WO-2017-064303, WO-2018-189721, WO-2018-189729, US-2020-0170727 and US-2020-0170726 to the same Applicant disclose various embodiments of surgical instruments suitable for robotic surgery and microsurgery. These types of surgical instruments typically comprise a proximal interface actuation portion (or backend portion) having an interface intended to be driven by a robotic manipulator, a rod, and an articulated cuff at the distal end of the rod. The articulated cuff consists of a plurality of links moved by a plurality of tendons (or actuation cables). Two terminal links have a free end and are adapted to operate directly on a patient's anatomy and/or handle a needle as well as a suture thread for performing anastomoses or other surgical therapies.

For example, WO-2017-064306 to the same Applicant shows a surgical instrument in which the tendons for actuating the degree of freedom of opening/closing of the articulated end-effector slide on convex ruled sliding surfaces of the end-effector links, simultaneously avoiding routing the tendons inside guide grooves or channels with concave section. Thereby, the cross-section of the sliding contact portion between the tendons and the link is minimized, thus reducing the sliding friction and allowing a boosted miniaturization of the articulated end-effector while ensuring a high dexterity given by the end-effector joints, such as rotational joints of pitch and yaw.

Furthermore, WO-2018-189722 to the same applicant discloses a surgical instrument in which the tendons for actuating the degree of freedom of opening/closing of the articulated end-effector, in addition to sliding on convex ruled sliding surfaces of the end-effector links, similar to what was previously discussed, are wound on said convex ruled sliding surfaces, describing arcuate paths which underlie a particularly high winding angle. In fact, by virtue of the low sliding friction of the tendons, they are capable of remaining in contact with the convex ruled surface of a link for a relatively long and arcuate longitudinal section.

In addition, US-2021-0106393 to the same applicant discloses some embodiments of a tendon consisting of intertwined polymer fibers. The use of polymer tendons allows reducing the sliding friction with respect to the use of metal tendons and at the same time an adequate dimensioning of the tendon allows traveling winding longitudinal paths in the articulated end-effector.

Furthermore, US-2020/0390507 shows a solution in which rollers are rotatably mounted on the links of the articulated terminal of the surgical instrument to guide the tendons. The provision of such rollers represents a clear obstacle to the miniaturization of the articulated terminal.

Therefore, the need is strongly felt to provide a surgical instrument solution having an articulated end-effector which is suitable for extreme miniaturization and at the same time robust, reliable and capable of providing a precise and repeatable cutting action, without imposing a reduced dexterity of the articulated end-effector.

Furthermore, the need is felt to suggest a surgical instrument solution for teleoperated robotic micro-surgery which although simple to assemble and to build as well as reliable and precise and robust when under operating conditions, is adapted to allow a desired and controlled spatial orientation of the cutting action with respect to, for example, the main longitudinal extension direction of the surgical instrument body which can be useful to facilitate the observation of the surgery.

The need is felt to suggest a solution which allows assembling an articulated tip surgical micro-instrument provided with grip and/or scissors and which consists of the
smallest number of components so that it can be assembled
easily and in a cost-affordable manner.

The need is felt to suggest a solution which allows making
micromechanical parts and in particular sharpened micro-
mechanical parts with a high geometric precision and repeat-
ability for the formation of an articulated tip micro-instru-
ment provided with grip and/or scissors.

Solution

It is an object of the present invention to obviate the
drawbacks complained of with reference to the background
art.

This and other objects are achieved by a surgical instru-
ment, as well as a method, as well as a rotational joint.

According to an aspect of the invention, a surgical cutting
instrument comprising a rod or shaft having a distal end and
an articulated end-effector connected to the distal end of the
rod.

Said articulated end-effector comprising a connection link
connected to the distal end of the rod having a body
comprising in a single piece one or more convex ruled
surfaces of connection links with parallel generator lines,
and a first distal connecting portion;

Said articulated end-effector comprising a support link
articulated to the connection link and having a body com-
prising in a single piece one or more convex ruled surfaces
of support links with parallel generator lines, and a proximal
connecting portion articulated to the first distal connecting
portion of the first connection link, defining a proximal
rotational joint for the connection link and the support link
so that they can rotate relatively about a common proximal
rotation axis, and a second distal connecting portion;

Said articulated end-effector comprising a blade holder
link articulated to the support link having a body comprising
in a single piece a blade holder link attachment root having
a pulley portion formed by one or more convex ruled
surfaces of the blade holder root with parallel generator
lines, and a drag portion.

Said articulated end-effector comprising a blade link,
integral in rotation with said blade holder link, having a
body comprising in a single piece a cutting edge and a drag
counter-portion engaged with said drag portion of the blade
holder link;

Said articulated end-effector comprising a reaction link
articulated to the support link and to the group formed by the
blade link and the blade holder link, having a body com-
prising in a single piece an attachment root having a pulley
portion formed by one or more convex ruled surfaces of
reaction link root, with parallel generator lines.

According to an aspect of the invention, the blade holder
attachment root and the reaction link attachment root define
with the second distal connecting portion of the support link
a distal rotational joint for the blade holder link, the reaction
link and the support link, so that they can relatively rotate
about a common distal rotation axis orthogonal to said
common proximal rotation axis.

According to an aspect of the invention, a counter-blade
portion is included which is integral in rotation with said
attachment root of the reaction link.

Said surgical cutting instrument further comprises a first
pair of antagonistic tendons extending along the rod and
connected to the blade holder link for moving the blade link
about said common distal rotation axis, and a second pair of
antagonistic tendons extending along the rod and connected
to said reaction link for moving the counter-blade portion about said common distal rotation axis. Furthermore, the
attachment root of the blade holder link comprises in a single
piece at least a first termination seat receiving said first pair
of antagonistic tendons and the attachment root of the
reaction link comprises in a single piece at least a second
termination seat receiving said second pair of antagonistic
tendons.

According to an aspect of the invention, said one or more
convex ruled surfaces with parallel generator lines of the
connection link are parallel to said common proximal rota-
tion axis, and at least one of said one or more convex ruled
surfaces with parallel generator lines of the support link is
parallel to said common proximal rotation axis, and said one
or more convex ruled surfaces of blade holder root with
parallel generator lines of the blade holder link and said one
or more convex ruled surfaces with parallel generator lines
of the reaction link are parallel to the common distal rotation
axis, and the first pair of antagonistic tendons and the second
pair of antagonistic tendons are adapted to slide longitudi-
nally on said one or more convex ruled surfaces of the
connection link and on said one or more convex ruled
surfaces of the support link and are adapted to wind/unwind
without sliding on the respective convex ruled surface of the
root of the blade holder link or the reaction link, to move in
opening/closing the blade link and the counter-blade por-
tion, respectively.

Preferably, the cutting edge of the blade link is adapted to
abut against said counter-blade portion during the movement
of the degree of freedom of opening/closing in a mechanical
interference contact condition to exert a cutting action, and
the cutting edge of the blade link is elastically flexible in a
direction parallel to the common distal rotation axis.

A first distance in a direction parallel to the common distal
rotation axis can be identified between the first termination
seat of the blade holder link root and a surface of said one
or more convex ruled surfaces of the support link, which is
constant for any cutting condition.

A second distance in a direction parallel to the common
distal rotation axis can be detected between the second root
termination seat of the further link and a surface of said one
or more convex ruled surfaces of the support link, which is
constant for any cutting condition.

In accordance with an embodiment, the blade holder link
comprises in a single piece a first cantilevered drag leg
extending from the blade holder link root forming a free end
of the first leg, axially delimiting said first termination seat,
and in which the reaction link comprises in a single piece a
second cantilevered drag leg extending from the reaction
link root forming a free end of the second leg, axially
delimiting said second termination seat, said first and second
cantilevered legs each comprising abutment and drag walls
placed undercut with respect to the respective termination
seats acting as dragging abutments for the respective tendon
termination. In such a case, it is possible to identify a first
distance in an axial direction between the first cantilevered
leg of the blade holder link and a surface of said one or more
convex ruled surfaces, for example of the support link, is
constant for any cutting condition and a second distance in
a direction parallel to the common distal rotation axis
between the second cantilevered leg and a surface of said
one or more convex ruled surfaces of the support link, is
constant for any cutting condition.

The first distance and the second distance can be mutually
equal.

The first distance and/or the second distance can be zero.

The attachment root of the blade holder link can comprise
a first surface facing axially outwards, and the root of the reaction link can comprise a second surface facing axially outwards, and in which a further axial distance can be detected between said first attachment root surface of the blade holder link and said second attachment root surface of the reaction link, which is constant for any cutting condition.

In accordance with an embodiment, the blade holder link comprises in a single piece a first cantilevered drag leg extending from the blade holder link root forming a free end of the first leg, axially delimiting said first termination seat, and in which the reaction link comprises in a single piece a second cantilevered drag leg extending from the reaction link root forming a free end of the second leg, axially delimiting said second termination seat, said first and second cantilevered legs each comprising abutment and drag walls placed undercut with respect to the respective termination seats acting as dragging abutments for the respective tendon termination. In such a case, it is possible to identify a first distance in an axial direction between the first cantilevered leg of the blade holder link and a surface of said one or more convex ruled surfaces, for example of the support link, is constant for any cutting condition and a second distance in a direction parallel to the common distal rotation axis between the second cantilevered leg and a surface of said one or more convex ruled surfaces of the support link, is constant for any cutting condition.

According to an embodiment, the overall sliding friction force exchanged between each tendon and all the ruled surfaces of the links on which the tendon slides, when in operating conditions, is much less than the tensile force transmitted by the same tendon to achieve the elastic bending deformation of the blade portion of the blade link when the degree of freedom of opening/closing is moved in closing to exert a cutting action. In other words, said sliding friction force of the tendons can be much less than the mechanical interference contact friction force between the blade link and the counter-blade portion. For this purpose, the tendons can be made of polymer material, and the links can be made of metallic material, and the convex ruled surfaces with parallel generator lines of the links can be smooth, to reduce the longitudinal sliding friction of the tendons on the links. For example, the ruled surfaces of the links are obtained by wire electro-erosion.

Said distal rotational joint can be a rigid rotational joint in the axial direction. Preferably, elastic elements are not included in the coupling and the elasticity is provided distally with respect to the rotational joint, i.e., on the blade.

Preferably, all the convex ruled surfaces of the connection link, the support link, the pulley portion of the blade holder link and the pulley portion of the reaction link lack longitudinal channels. Therefore, the actuation tendons do not slide inside concave channels.

A third pair of antagonistic tendons can be provided for moving the support link about said common proximal rotation axis with respect to the connection link, the support link comprising at least a third termination seat which receives the tendon terminations of said third pair of antagonistic tendons. Preferably, the actuation tendons of the support link of said third pair of antagonistic tendons wind/unwind without sliding longitudinally on said one or more convex ruled surfaces of the support link, which therefore act as pulley surfaces for the actuation tendons of the third pair of antagonistic tendons.

According to an aspect of the invention, a cutting method for a surgical instrument comprising the step of providing a articulated end-effector at the distal end of a rod comprising a connection link and a support link articulated together in a proximal rotational joint, in which said support link is articulated in a distal rotational joint with: a blade link having a cutting edge, and a blade holder link integral in rotation with the blade link, and a reaction link having a counter-blade portion.

Furthermore, the method comprises the steps of longitudinally sliding the actuation tendons of at least one pair of antagonistic tendons on one or more convex ruled surfaces with parallel generator lines of at least one of a connection link and a support link to orient the cutting edge of the blade link in a desired orientation, and longitudinally sliding the actuation tendons of at least one pair of antagonistic actuation tendons of the distal rotational joint on one or more convex ruled surfaces with parallel generator lines of the connection link and support link to bring the cutting edge into contact with said counter-blade portion.

The method further comprises elastically bending at least one of the cutting edge and the counter-blade portion, making a mechanical interference contact therebetween, exerting a cutting action.

The step of longitudinally sliding the antagonistic tendons of at least one pair of antagonistic actuation tendons of the distal rotational joint on the convex ruled surfaces with parallel generator lines of the connection link and the support link, can comprise the step of winding at least one movement tendon of the distal rotational joint on the convex ruled surfaces on which it slides, by a winding angle between 60° and 300°, and preferably greater than 120°.

According to an aspect of the invention, a rotational joint of a cutting joint having a rotation axis actuated by actuation tendons comprises a distal connecting portion of a support link, an attachment root of a blade link having an elastically bendable body in an axial direction, an attachment root of a blade holder link integral in rotation with the blade link, and an attachment root of a reaction link integral in rotation with a counter-blade portion, in which the cutting edge of the blade link is adapted to abut against said counter-blade portion during the movement of the degree of freedom of opening/closing in a mechanical interference contact condition to exert a cutting action.

The root of the blade holder link comprises in a single piece at least a first termination seat for a first pair of antagonistic tendons, and the root of the reaction link comprises in a single piece at least a second termination seat for a second pair of antagonistic tendons. The support link comprises in a single piece one or more convex ruled surfaces with parallel generator lines on which the tendons of the first and second pairs of antagonistic tendons slide during the cutting action.

Said rotational joint is rigid in the axial direction so that a first distance in the direction parallel to the common distal rotation axis between the first termination seat of the blade holder link root and a surface of said one or more convex ruled surfaces of the support link is constant for any cutting condition; and a second distance in the direction parallel to the common distal rotation axis between the second termination seat of the reaction link root and a surface of said one or more convex ruled surfaces of the support link is constant for any cutting condition.

By virtue of the suggested solutions, extreme and boosted miniaturization of an articulated end-effector is allowed, for example which reproduces a wrist, without pulleys which are replaced by surfaces ruled in one piece with links, having a very small radius. Therefore, the known metal tendons can be replaced by miniaturized polymer tendons which, by virtue of the low friction, slide on such ruled surfaces defining the movement thereof, It is possible to make surgical cutting instruments of minimum size having a simplified opening-closing and cutting mechanism, replacing an adjustment dowel and/or a Belleville spring train with the inclusion of an elastic blade (and preferably a curved counter-blade) the closure with interference of which exerts the deformation and the cutting action thereof.

Those components (keyed pulleys or rotationally connected to the links, Belleville-type springs on the distal articulation pin, metal actuation tendons) which are relatively bulky and/or difficult to assemble as the scale descends, with consequent risks of intolerable clearance, which would represent an obstacle to miniaturization, are in fact eliminated.

The attachment root having a convex ruled winding surface for the respective tendon forming a pulley portion without longitudinal channels, comprises geometric drag elements adapted to allow the interlocking of a further component, which is preferably a planar and elastic blade, and such geometric elements are such as to guide the blade integrally against the counter-blade in the opening and closing action.

BRIEF DESCRIPTION OF THE DRAWINGS

Further features and advantages of the surgical instrument will appear from the following description of preferred embodiments, given by way of non-limiting illustration, with reference to the accompanying drawings (it should be noted that references to "an" embodiment in this disclosure do not necessarily refer to the same embodiment, and are to be understood as at least one, furthermore, for the purposes of conciseness and reduction of the total number of drawings, a certain drawing can be used to show the features of more than one embodiment, and not all elements of the drawing may be necessary for a certain embodiment), in which:

FIG. 1-B shows an axonometric view of a surgical instrument, according to an embodiment;

FIG. 18 shows a vertical elevation view of a blade link, according to an embodiment;

FIG. 19 is a diagram which diagrammatically shows a plan view of the conformation assumed by a blade portion and a counter-blade surface of the portion of the end-effector in FIG. 17 in various mechanical cutting interference configurations, according to an embodiment;

FIG. 20 shows an axonometric view with separate parts of a portion of the end-effector in FIG. 17;

FIG. 41-B is a plan view of the end-effector portion in FIG. 41-A;

FIG. 41-C is an axonometric view of the end-effector portion in FIG. 41-A.

DETAILED DESCRIPTION OF SOME EMBODIMENTS

Figure 1A:
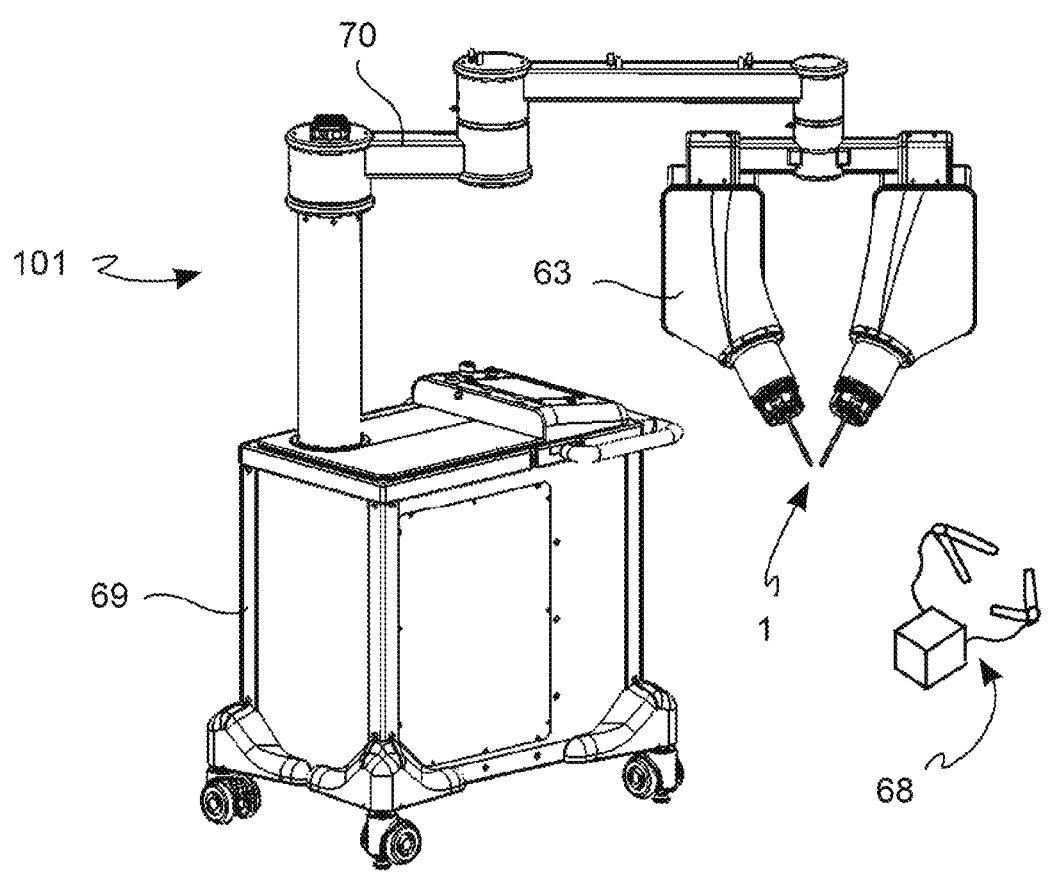
FIG. 1-A shows an axonometric view of a robotic surgery system, according to an embodiment.

Reference throughout this description to "an embodiment" is meant to indicate that a particular feature, structure or function described in relation to the embodiment is included in at least one embodiment of the present invention. Therefore, the formulation "in an embodiment" in various parts of this description do not necessarily all refer to the same embodiment. Furthermore, particular features, structures or functions such as those shown in different drawings can be combined in any suitable manner in one or more embodiments.

In accordance with a general embodiment, a surgical cutting instrument 1 is provided. For example, said surgical cutting instrument 1 is a surgical scissor type instrument. For example, said surgical cutting instrument 1 is an instrument of the needle-driver/suture-cutter type.

The surgical instrument 1 comprises a rod 7 or shaft 7 having a distal end 8 and an articulated end-effector 9 (in other words an articulated end device 9 connected to the distal end 8 of the rod 7.

Figure 1B:
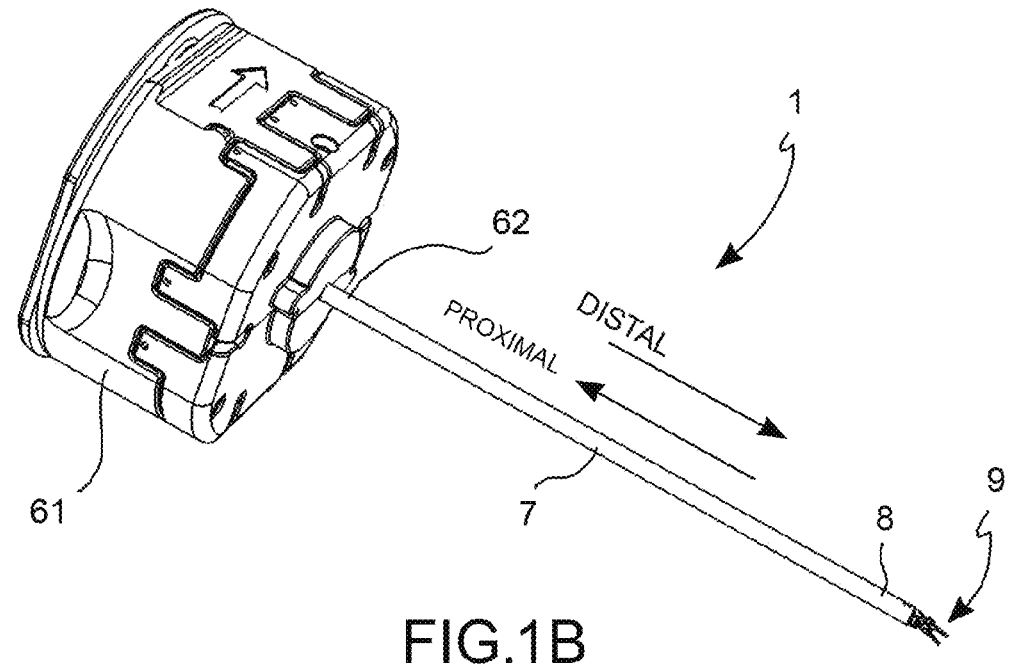
Figure 2:
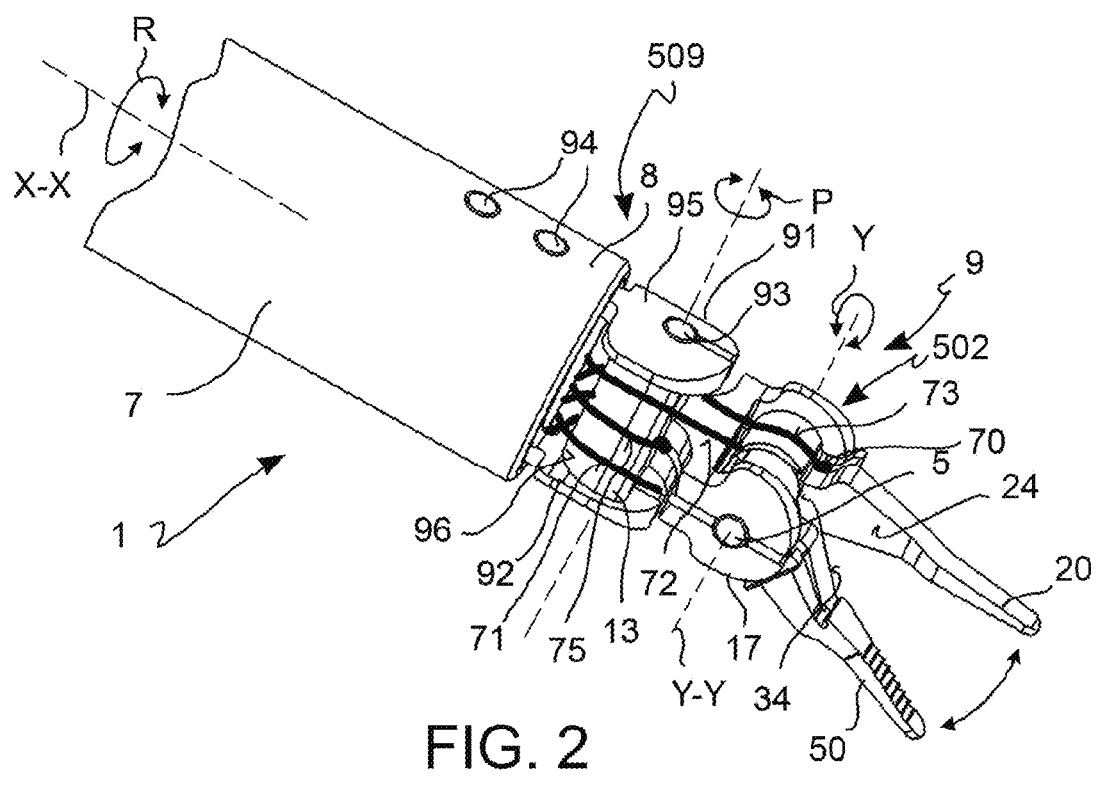
FIG. 2 shows an axonometric view of a portion of a surgical instrument of the needle-driver/suture-cutter type comprising an end-effector at the distal end of the rod, according to an embodiment, in which the actuation tendons are diagrammatically shown.
Figure 3:
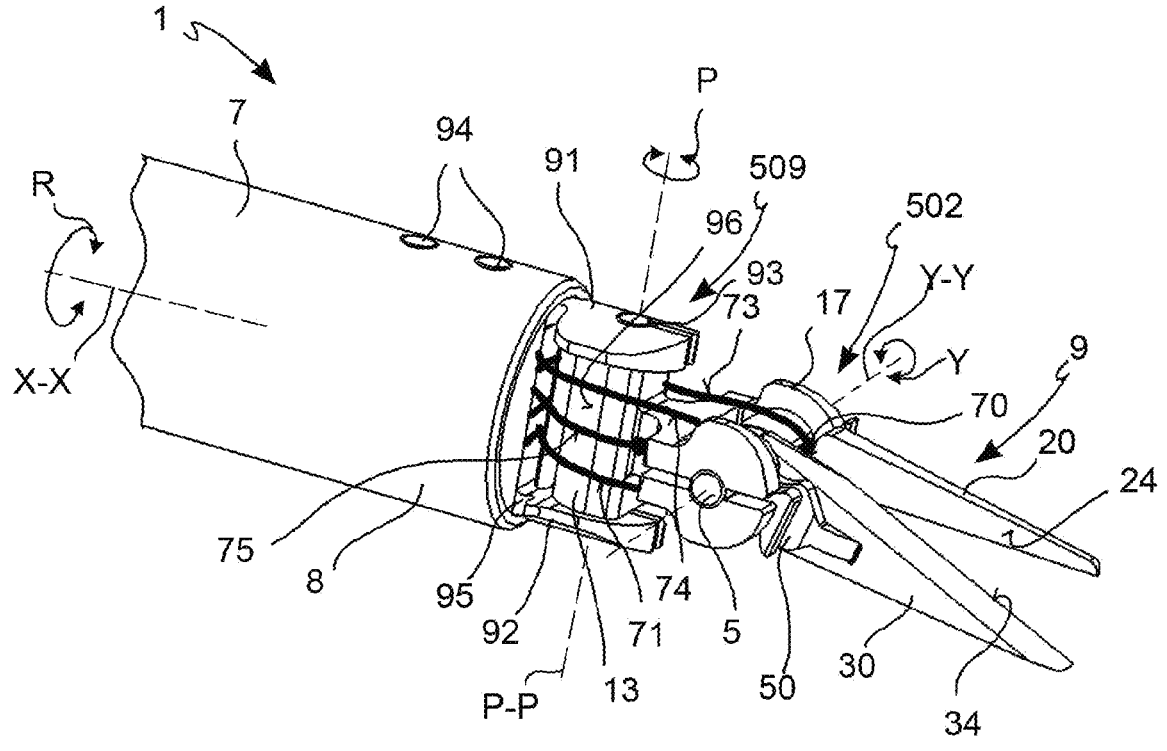
FIG. 3 shows an axonometric view of a portion of a surgical instrument of the surgical scissors type comprising an end-effector at the distal end of the rod, according to an embodiment, in which the actuation tendons are diagrammatically shown.
Figure 4:
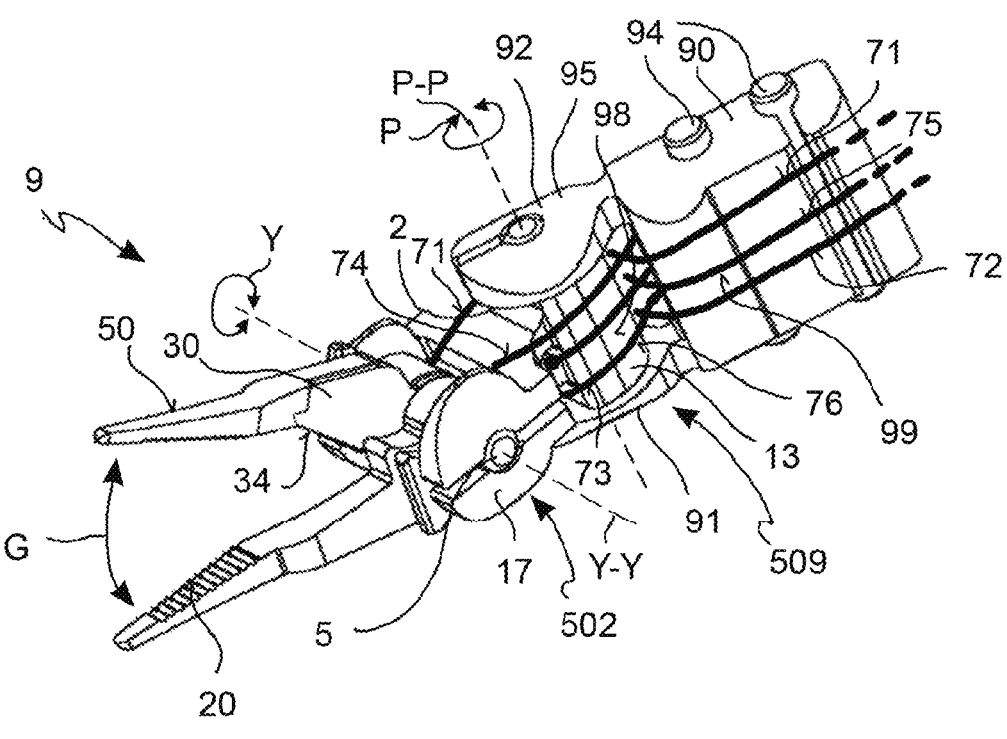
FIG. 4 shows an axonometric view of an end-effector of a surgical instrument of the needle-driver/suture-cutter type according to an embodiment, in which the actuation tendons are diagrammatically shown.
Figure 5:
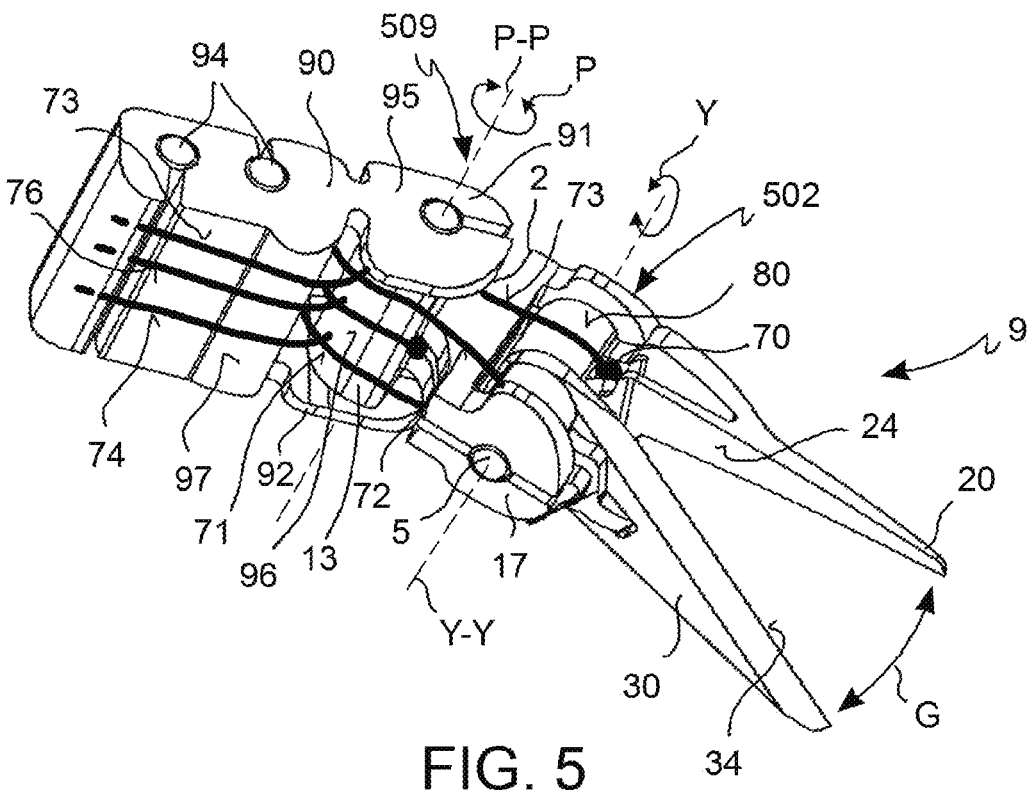
FIG. 5 shows an axonometric view of an end-effector of a surgical instrument of the scissors type according to an embodiment, in which the actuation tendons are diagrammatically shown.

Said surgical instrument 1 is particularly suitable, but not uniquely intended, for robotic surgery and can be connectable to a robotic manipulator 103 comprising motorized actuators of a robotic surgery system 101, as for example shown in FIG. 1-A. For example, said surgical instrument 1 can be associated with a mechanical and manual control and actuation device.

The robotic surgery system 101 comprising said surgical instrument 1 is particularly suitable, but not uniquely intended, for robotic microsurgery operations. The robotic surgery system 101 can be intended for robotic laparoscopy operations.

Not necessarily said rod 7 or shaft 7 is a rigid shaft and for example can be a bendable shaft and/or an articulated shaft, although in accordance with a preferred embodiment said shaft 7 is a rigid shaft. A proximal interface portion 104 or backend portion 104 of the surgical instrument 1 can be included at the proximal end 102 of the rod 7, to form the interface with a robotic manipulator 103 of the robotic surgery system 101, as shown for example in FIG. 1-B. A sterile barrier can be interposed between the robotic manipulator and the proximal interface portion 104 of the surgical instrument. For example, said proximal interface portion 104 can comprise a set of interface transmission elements for receiving the driving actions imparted by the robotic manipulator 103 and transmitting them to the articulated end-effector 9. In accordance with an embodiment, the surgical instrument 1 is detachably associated with the robotic manipulator 103 of the robotic surgery system 101.

The articulated end-effector 9 at the distal end 8 of the rod 7 can comprise a plurality of links articulated to one another in one or more rotational joints movable by a number of pairs of antagonistic actuation tendons extending from the proximal interface portion 104 to the articulated end-effector 9 inside the rod 7 ending in termination seats included on at least some of the links of the articulated end-effector 9. The pair of actuation tendons of one or more pairs of antagonistic tendons can be obtained with a single tendon forming a round trip path from the proximal interface portion 104 of the instrument to a link of the articulated end-effector of the instrument.

Preferably, the term "link" refers to a body made in a single piece, i.e., a monobloc body.

Not necessarily all the links forming the articulated end-effector 9 are articulated, i.e., movable, with one another and/or with respect to the distal end 8 of the rod 7.

For example, said end-effector 9 can be an articulated cuff of the "roll-pitch-yaw" type according to a terminology widely adopted in the field. For example, said end-effector 9 can be an articulated end-effector 9 of the "snake" type, i.e., comprising a multitude of coplanar and/or non-planar rotational joints.

Said articulated end-effector 9 comprises a (first) connection link 90 connected to the distal end 8 of the rod 7 having a body comprising in a single piece, one or more convex ruled surfaces of connection links 97, 99 with parallel generator lines. The connection link 90 further comprises in a single piece a first distal connecting portion 95. Preferably said first distal connecting portion 95 of the first connection link 90 comprises two prongs 91, 92 and is adapted to form a proximal rotational joint having a proximal rotation axis P-P. In accordance with a preferred embodiment, the convex ruled surfaces generatrix lines 97, 99 of the connection link 90 are all parallel to the proximal rotation axis P-P.

The connection link 90 can be rigidly fixed by fixing device 94 (in the example shown as a pair of fixing pins 94, but alternatively the fixing device 94 can comprise pins, rivets, staples, one or more threaded elements, interlocking profiles, or the like) to the distal end 8 of the rod 7 and can comprise two prongs 91, 92 forming the distal connecting portion 91, 92 to form a proximal rotational joint 509 or pitch rotational joint 509 having a common proximal rotation axis P-P, or pitch axis P-P.

Said articulated end-effector 9 comprises a (second) support link 2 articulated to the first connection link 90 and having a body comprising in a single piece one or more convex ruled surfaces of support links 96, 98 with parallel generator lines.

The support link 2 further comprises in a single piece a proximal connecting portion 13 articulated to the first distal connecting portion 95 of the first connection link 90, defining a proximal rotational joint 509 for the connection link 90 and the support link 2 so that they can rotate relatively about a common proximal rotation axis P-P.

The support link 2 further comprises in a single piece a second distal connecting portion 17. The distal connecting portion 17 of the support link 2 preferably comprises a support structure, for example comprising two prongs 3, 4, for defining a distal rotation axis Y-Y i.e., for forming a distal rotational joint 502 or yaw rotational joint 502 having a common distal rotation axis Y-Y, or yaw axis Y-Y, which can be orthogonal to the pitch proximal rotation axis P-P.

The support structure of the support link 2 is preferably a rigid support structure, i.e., it is for example a rigid support fork, the relative position of the prongs 3, 4 is rigidly determined as is the relative position of a prong 3, 4 and a ruled surface 96, 98. In accordance with an embodiment, said distal rotation axis Y-Y is a yaw rotation axis Y-Y and said proximal rotation axis P-P is a pitch rotation axis P-P, in which the yaw rotation axis Y-Y and the pitch rotation axis P-P are orthogonal to each other. Thereby, the connection link 2 with the proximal and distal connecting portions 13, 17 thereof, defines in a single piece two rotational joints 509, 502 having rotation axes P-P, Y-Y orthogonal to each other.

The articulated end-effector 9 further comprises a (third) blade holder link 50, articulated to the support link 2 having a body comprising in a single piece an attachment root of a blade holder link 51 having a pulley portion 79 formed by one or more convex ruled surfaces 79 of blade holder root with parallel generator lines. The blade holder link 50 comprises in a single piece a proximal attachment root 51 which is articulated in said distal rotational joint 502.

Advantageously, the articulated end-effector 9 further comprises a (fourth) blade link 30, integral in rotation with said blade holder link 50, having a body comprising in a single piece a cutting edge 34. The cutting edge 34 is adapted to perform a cutting action. The blade link 30 comprises in a single piece a proximal attachment root 31 which is articulated in said distal rotational joint 502. The blade link 30 preferably comprises in a single piece an attachment root 31 arranged next to the root 51 of the blade holder link 50 and preferably the root 31 of the blade link 30 is next to, in direct and intimate contact with, the root 51 of the blade holder link 50.

The body of the blade holder link 50 further comprises in a single piece a drag portion 57 and the body of the blade holder link 30 further comprises in a single piece a drag counter-portion 37 engaged with said drag portion of the blade holder link 50. The drag engagement can be obtained by an engagement between the blade link 30 and the blade holder link 50. The drag engagement between the blade link 30 and the blade holder link 50 can be arranged distally with respect to the common rotation axis Y-Y, i.e., distally with respect to the attachment roots 31 and 51. In such a case, the drag engagement portion 37 (or drag portion 37) of the blade link 30 is preferably positioned far from the blade link root 31 so as to ensure a precise drag, even though the drag portion 37 of the blade link 30 can be positioned at the blade link root 31 to achieve a more advantageous mechanical transfer.

The articulated end-effector 9 further comprises a (fifth) further reaction link 20 articulated to the support link 2 and the blade holder link 50 having a body comprising in a single piece a further attachment root 21 of the reaction link 20 having a pulley portion 80 one or more convex ruled surfaces 80 with parallel generator lines.

The support link 2, the group formed by the blade holder link 50 and the blade link 30, and the second tip are articulated to each other in said common rotation axis Y-Y defining an axial direction coincident with or parallel to the common rotation axis Y-Y. In other words, the distal connecting portion 17 of the support link 2 is articulated with respect to the group formed by the root 51 of the blade holder link 50 and the root 31 of the blade link 30, and the root 21 of the fifth, further reaction link 20 in said distal common rotation axis Y-Y. Preferably, for clarity of presentation, an axial direction coincident or parallel with the direction of the common rotation axis Y-Y is defined.

Preferably, for clarity of presentation, with reference to the blade link 30 and/or the blade holder link 50, there is further defined an internal axial direction facing along the axial direction towards said fifth, further reaction link 20 and similarly, with reference to the second tip 20, said internal axial direction will be facing opposite, i.e. towards the blade link 30 and/or blade holder link 50.

The proximal and distal directions (or senses) are understood as referring in accordance with the common meaning of the terms, as shown by the arrows in FIG. 1-B.

Preferably, for clarity of presentation, the term "radial" will refer to a direction which is substantially orthogonal to the common rotation axis Y-Y and incident thereto.

Preferably, for clarity of presentation, it also means a longitudinal direction which globally can be substantially coincident with the longitudinal extension direction of the surgical instrument 1, as well as locally with the longitudinal extension direction of the elongated body of the blade link 30 and/or the blade holder link 50 and or the reaction link 20.

The root 21 of the further fifth reaction link 20 and the group formed by: the root 51 of the blade holder link 50 and the root 31 of the blade link 30 are articulated with respect to the distal portion 17 of the support link 2 about said common rotation axis Y-Y defining a degree of freedom of orientation of yaw Y. Therefore, the common rotation axis Y-Y (or a straight extension thereof) crosses said two prongs 3, 4, and said roots 21, 31, 51 and can be defined by an articulation pin 5.

Furthermore, the root 21 of the further fifth reaction link 20 is articulated with respect to the group formed by: the root 51 of the blade holder link 50 and the root 31 of the blade link 30 about said common rotation axis Y-Y, defining a relative degree of freedom of opening/closing G (or degree of freedom of cutting G, or degree of freedom of grip G according to a widely adopted terminology, although the activation of this degree of freedom does not necessarily results in a gripping action) to exert the cutting action.

With further advantage, a counter-blade portion 24 integral in rotation with said attachment root 21 of the reaction link 20 is included. Therefore, the reaction link 20 is integral in rotation with the counter-blade portion 24. Not necessarily, the reaction link 20 is in a single piece with the counter-blade portion 24, although in accordance with a preferred embodiment the reaction link 20 comprises the attachment root 21 and the counter-blade portion 24 in a single piece.

The surgical cutting instrument 1 further comprises a first pair of antagonistic tendons 71, 72 extending along the shaft 7 and connected to the blade holder link 50 to move the blade link 30 about said common distal rotation axis Y-Y. The attachment root 51 of the blade holder link 50 comprises in a single piece at least a first termination seat 15 which receives said first pair of antagonistic tendons 71, 72.

The surgical cutting instrument 1 further comprises a second pair of antagonistic tendons 73, 74 extending along the shaft 7 and connected to said further reaction link 20 for moving the counter-blade portion 24 about said common rotation axis of yaw Y-Y. The attachment root 21 of the further reaction link 20 comprises in a single piece at least a second termination seat 25 which receives said second pair of antagonistic tendons 73, 74.

Each tendon has a main longitudinal extension and is adapted to work exclusively tensioned.

Each tendon is in contact with the links 90, 2, 20, 30, 50 of the articulated end-effector 9 preferably exclusively on said convex ruled surfaces 79, 80, 96, 97, 98, 99 of at least some of the connection link 90, the support link 2, the blade holder link 50 (especially the root 51 of the blade holder link 50), the reaction link 20 (especially the root 21 of the reaction link 20). Preferably, the actuation tendons avoid being in contact with the blade link 30, and the blade link 30 is dragged in rotation by the blade holder link 50.

Advantageously, said one or more convex ruled surfaces 97, 99 with parallel generator lines of the connection link 90 are parallel to said common proximal rotation axis P-P, and at least one of said one or more convex ruled surfaces 96, 98 with parallel generator lines of the support link 2 is parallel to said common proximal rotation axis P-P. Furthermore, said one or more convex ruled surfaces 79 of the blade holder root 51 with parallel generator lines of the blade holder link 50 and said one or more convex ruled surfaces 80 of the pulley portion of the further root 21 with parallel generator lines of the further reaction link 20 are parallel to the common distal rotation axis Y-Y.

With further advantage, the first pair of antagonistic tendons 71, 72 and the second pair of antagonistic tendons 73, 74 are adapted to longitudinally slide on said one or more convex ruled surfaces 97, 99 of the connection link 90 and on said one or more convex ruled surfaces 96, 98 of the support link 2 and are adapted to wind/unwind without longitudinally sliding on the respective convex ruled surface of root 79 or 80 of the blade holder link 50 or the further reaction link 20 to move the blade link 30 and the counter-blade portion 24 in opening/closing, respectively.

Figures 9A, 9B:
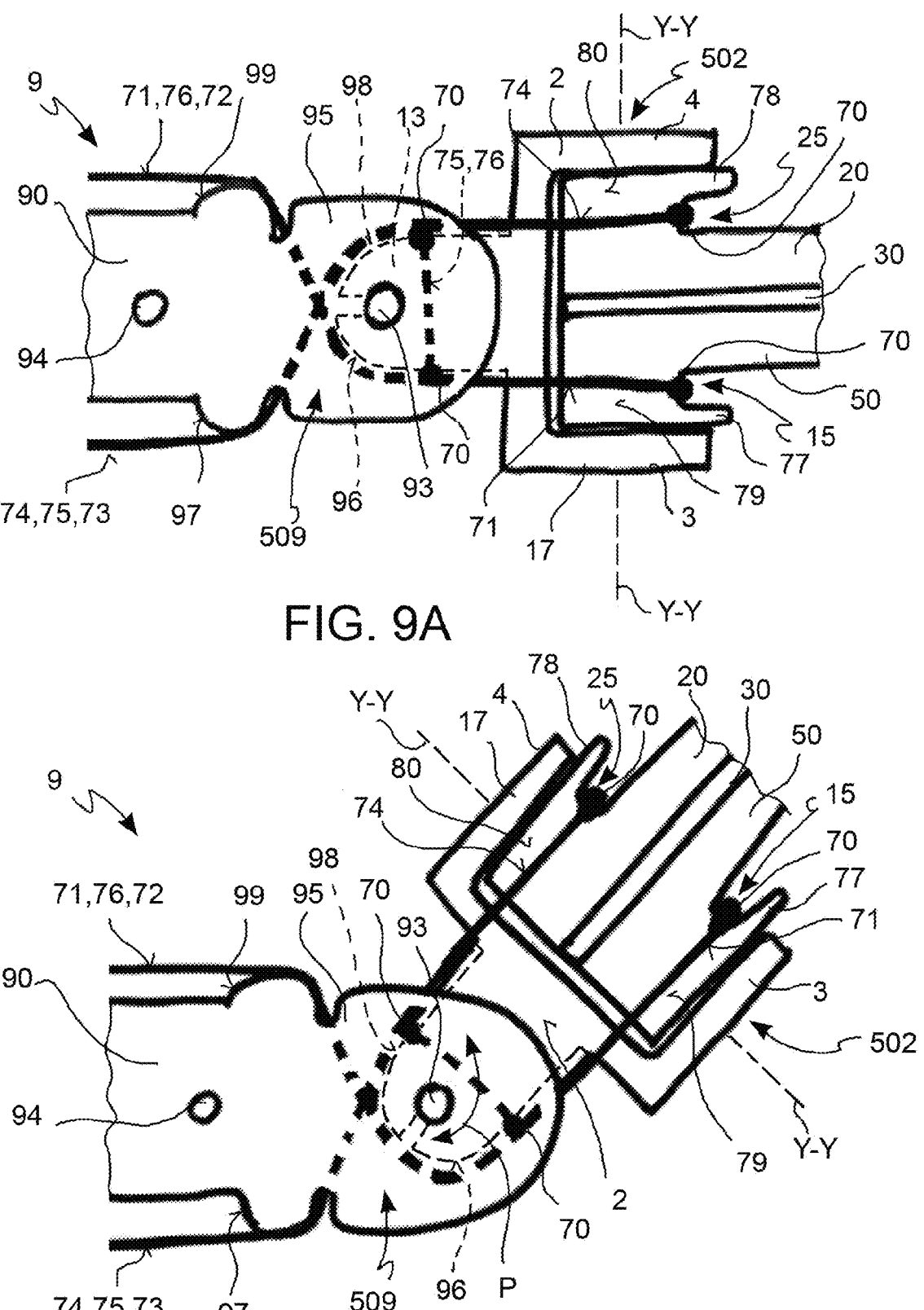
FIGS. 9-A and 9-B diagrammatically show an end-effector portion of a surgical instrument respectively in two operating configurations, according to an embodiment, in which the actuation tendons are diagrammatically shown.
Figure 10:
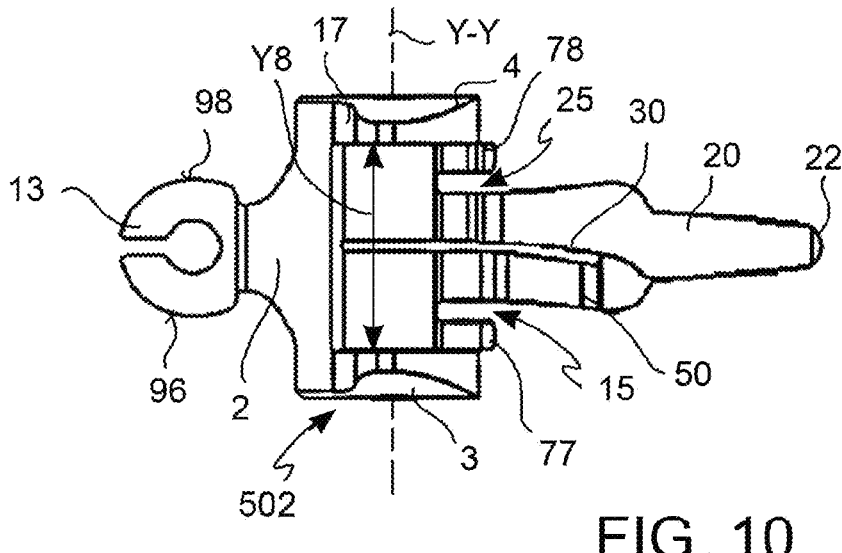
FIGS. 10, 11 and 12 show some embodiments of a portion of an end-effector of a surgical instrument in plan view.
Figure 11:
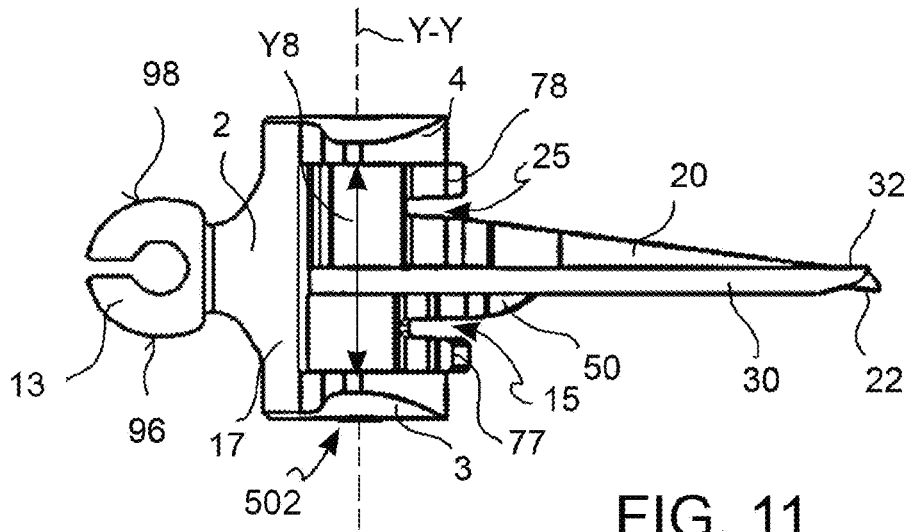
Figure 12:
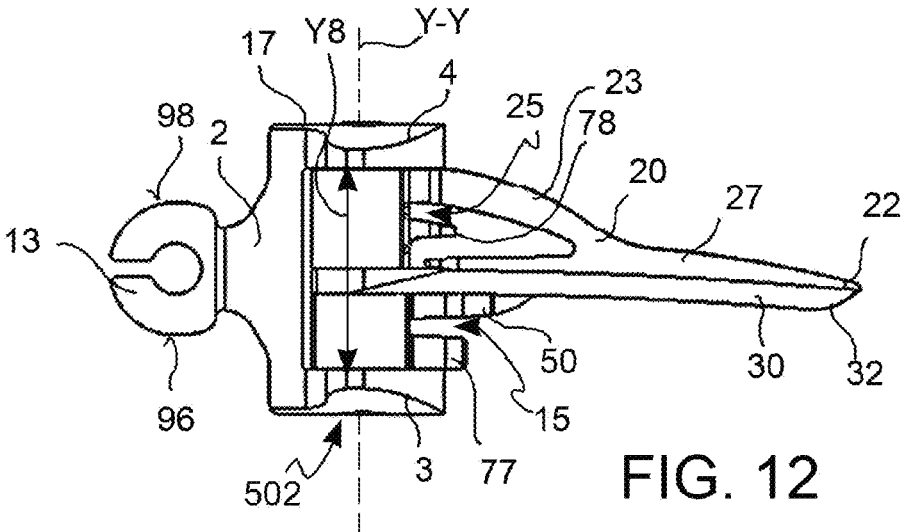
Figure 13:
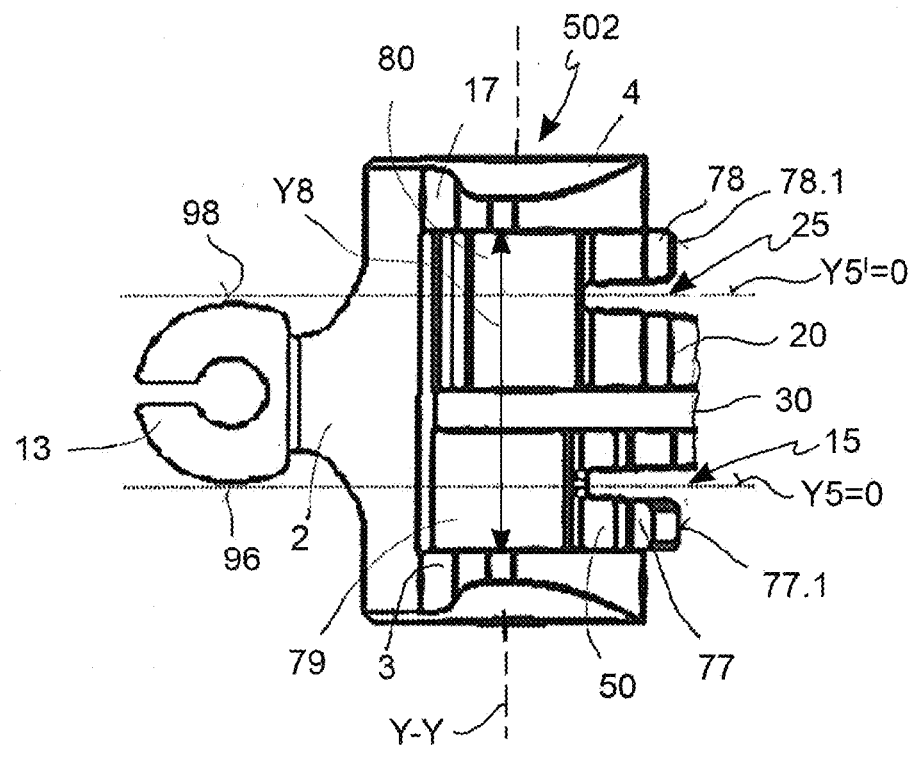
FIGS. 13 and 14 show a plan view of a distal rotational joint of an end-effector of a surgical instrument, according to some embodiments.
Figure 14:
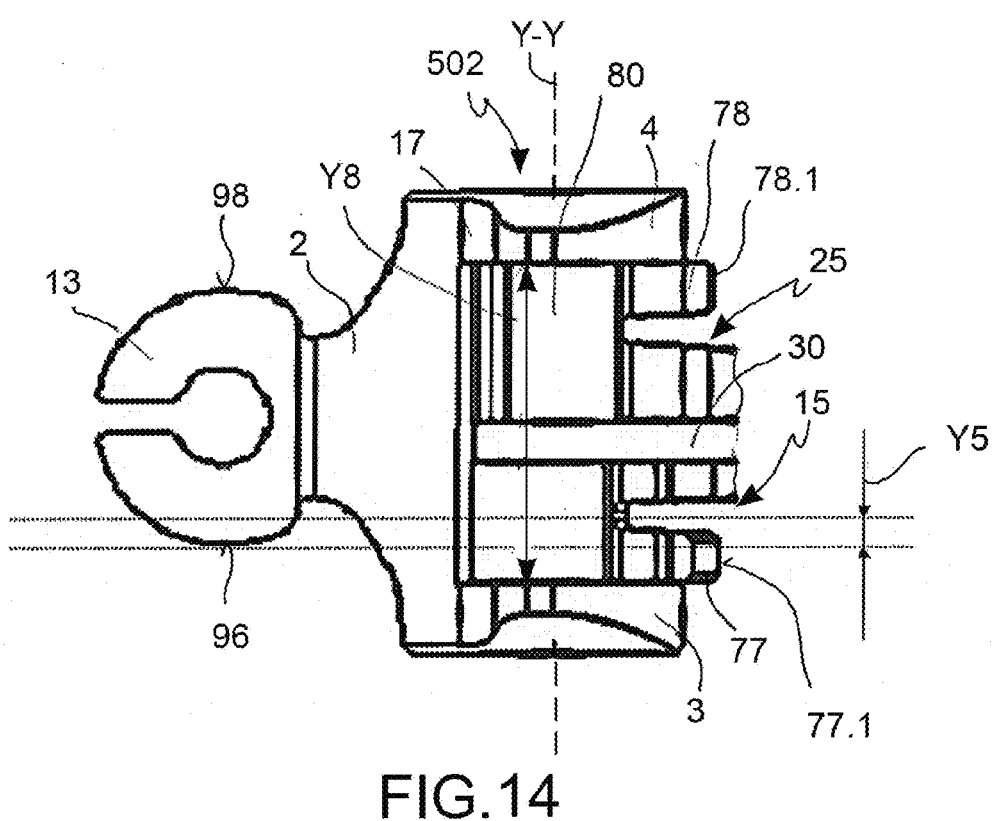
Figure 15A:
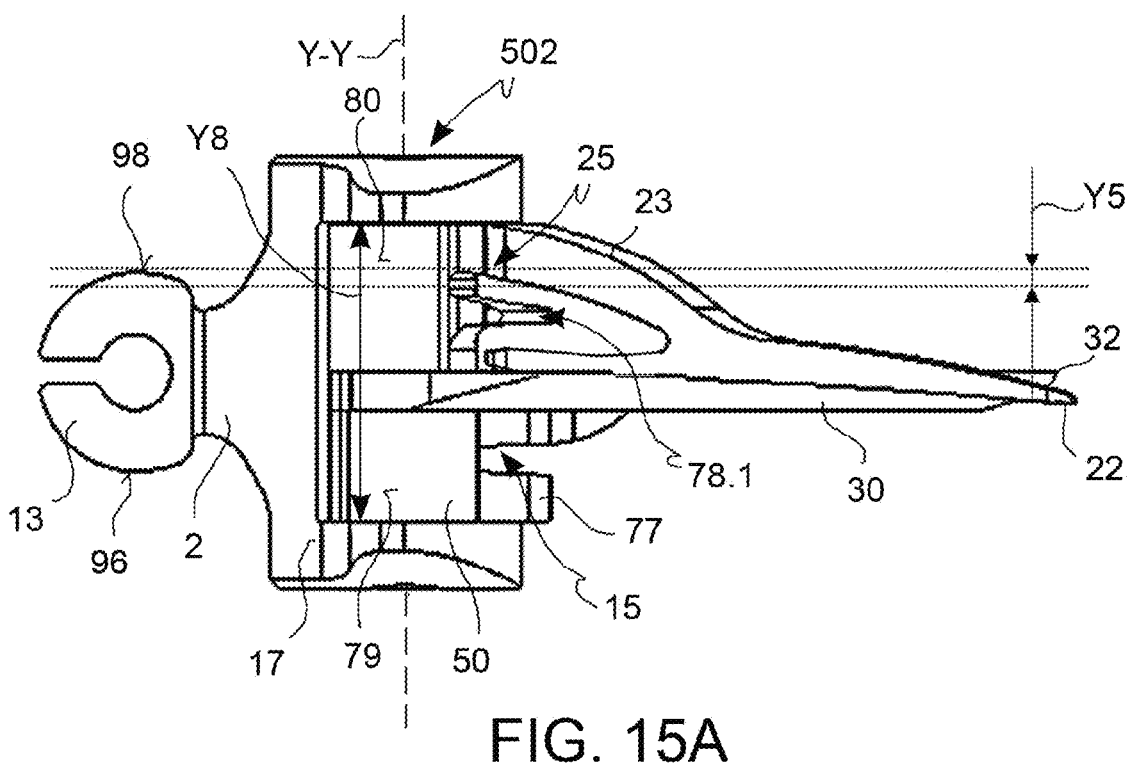
FIGS. 15-A and 15-B show a plan view of a distal rotational joint of an end-effector of a surgical instrument in two cutting configurations.
Figure 15B:
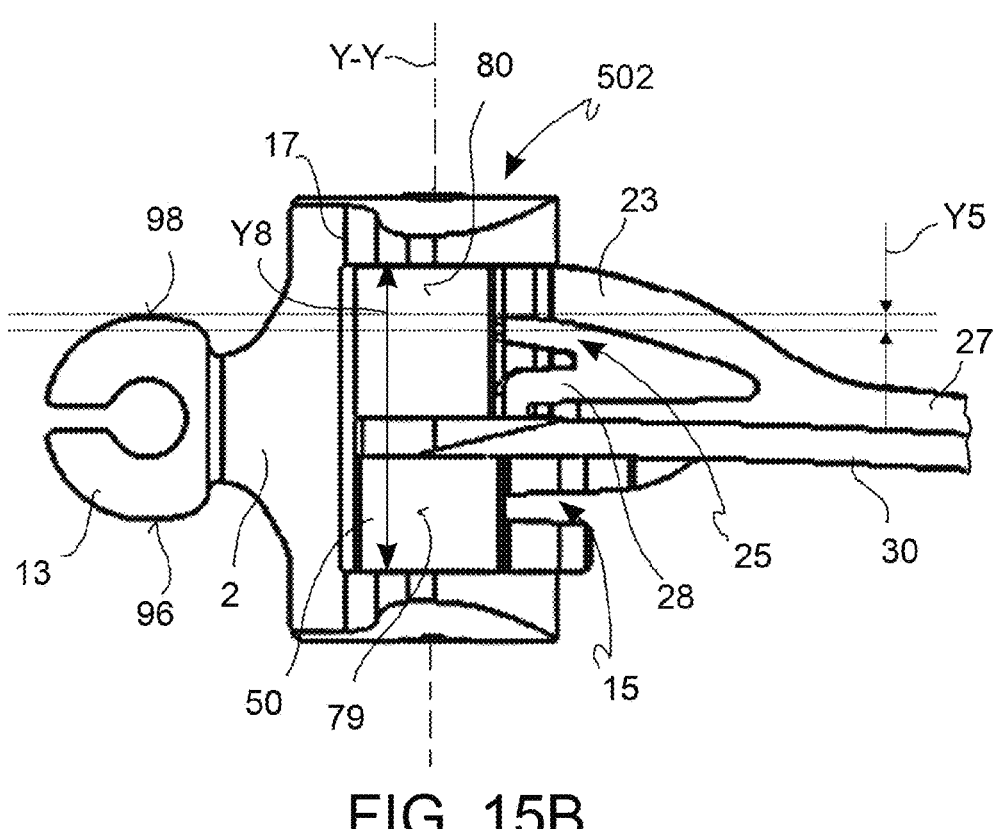
Figure 16:
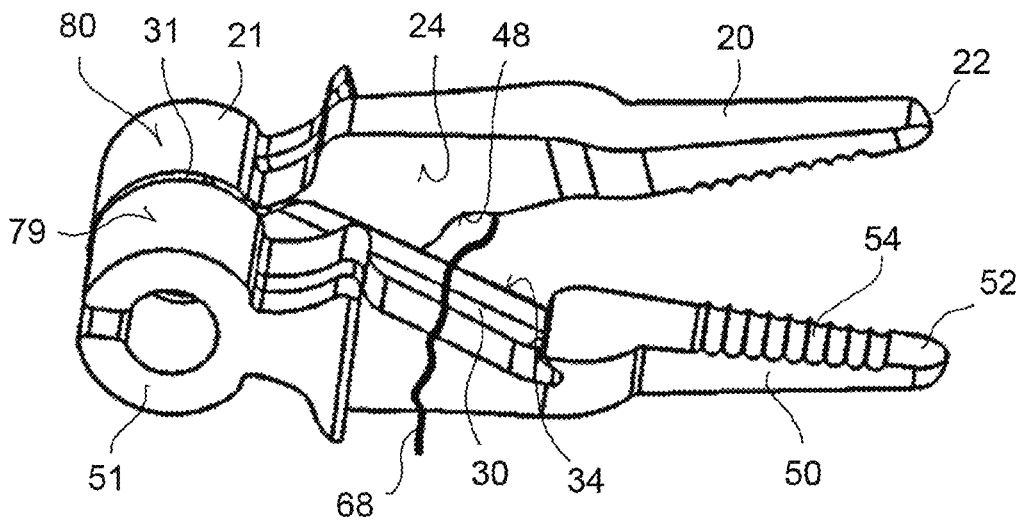
FIG. 16 shows an axonometric view of a surgical instrument of the needle-driver/suture-cutter type, according to an embodiment, during the cutting of a suture thread.
Figure 17:
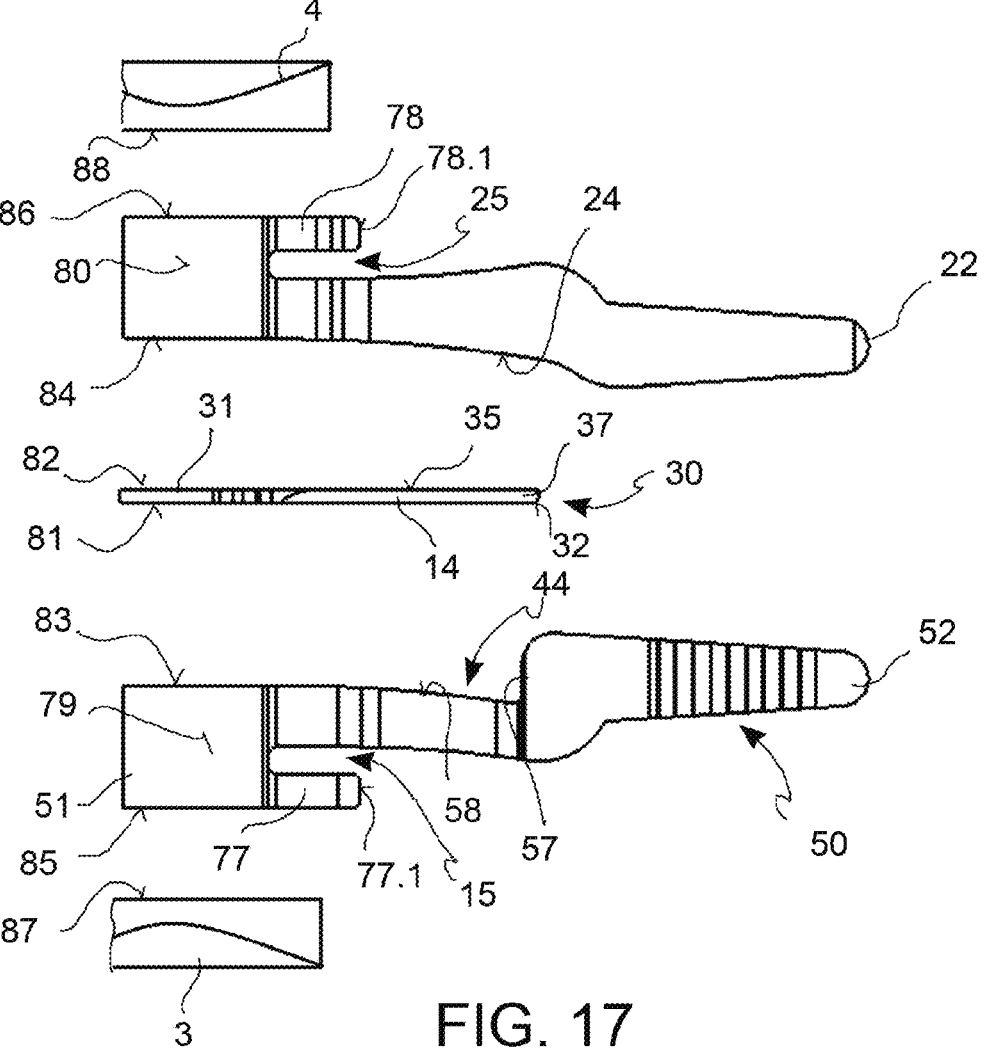
FIG. 17 shows a plan view with separate parts of a portion of an end-effector of a surgical instrument of the needle-driver/suture-cutter type, in accordance with an embodiment.

As diagrammatically shown in FIGS. 9-A and 9-B, actuation tendons 71, 72, 73, 74 of the pairs of antagonistic tendons adapted to activate the distal rotational joint 502 of the end-effector 9 and slide longitudinally on one or more convex ruled surfaces 97, 99 of the connection link 90, and slide longitudinally on one or more convex ruled surfaces 96, 98 of the support link 2. In other words, the sliding of the actuation tendons on the ruled surfaces occurs place in the longitudinal extension direction of the tendons themselves 71, 72, 73, 74. The path of each tendon 71, 72, 73, 74 is stationary with respect to the convex ruled surfaces on which it slides, i.e., although each tendon slides longitudinally, it does not slide axially, and the longitudinal extension direction of each tendon does not vary in any operating condition. In addition, preferably the actuation tendons 71, 72, 73, 74 of the pairs of antagonistic tendons adapted to activate the distal rotational joint 502 of the end-effector 9 comprise a first pair of tendons 71, 72 terminated on the root 51 of the blade holder link 50 and a second pair of tendons 73, 74 terminated on the root 21 of the reaction link 20, in which the first pair of tendons 71, 72 winds without sliding longitudinally on said pulley surface 79 formed by one or more convex ruled surfaces 79 with parallel generator lines to the distal rotation axis Y-Y, and in which the second pair of tendons 73, 74 winds without sliding longitudinally on said pulley surface 80 formed by one or more convex ruled surfaces 80 with parallel generator lines to the distal rotation axis Y-Y.

Meanwhile, the convex ruled surfaces 97, 99 of the connection link 90, and the convex ruled surfaces 96, 98 of the support link 2 lack guide channels or grooves for keeping the tendon inside a guide groove. The geometric relationship between the termination seats 15, 25 of the tendons 71, 72, 73, 74 and the ruled surfaces 79, 80, 96, 97, 98, 99 on which the actuation tendons of the distal rotational joint 502 slide longitudinally or wind without sliding favors the stationarity of the path of each tendon even in the absence of guide channels, or grooves on the body of the links of the end-effector. In addition, the absence of guide channels or grooves to guide the tendons allows keeping the contact surface between the cross-section of each tendon and the convex ruled surface on which it slides minimized, while keeping the sliding friction minimized.

As diagrammatically shown in FIGS. 9-A and 9-B, antagonist actuation tendons 75, 76 adapted to activate the proximal rotational joint 509 of the articulated end-effector 9 terminate on the support link 2 and do not slide longitudinally with respect to the support link 2, i.e., they do not slide longitudinally on said one or more ruled surfaces 96, 98 of the support link 2, but wind thereabout without sliding, while they slide longitudinally on said one or more ruled surfaces 97, 98 of the link 90 to move the proximal rotational joint P-P. Preferably, the body of the support link 2 comprises in a single piece at least a third termination seat 6 for receiving the third pair of antagonistic actuation tendons 75, 76, as explained in the following.

Therefore, the longitudinal extension of the tendons is locally orthogonal to the lines generating the ruled surfaces on which the tendons are locally in contact.

As mentioned above, the distal rotational joint 502 is capable of causing a cutting action.

Figure 41A:
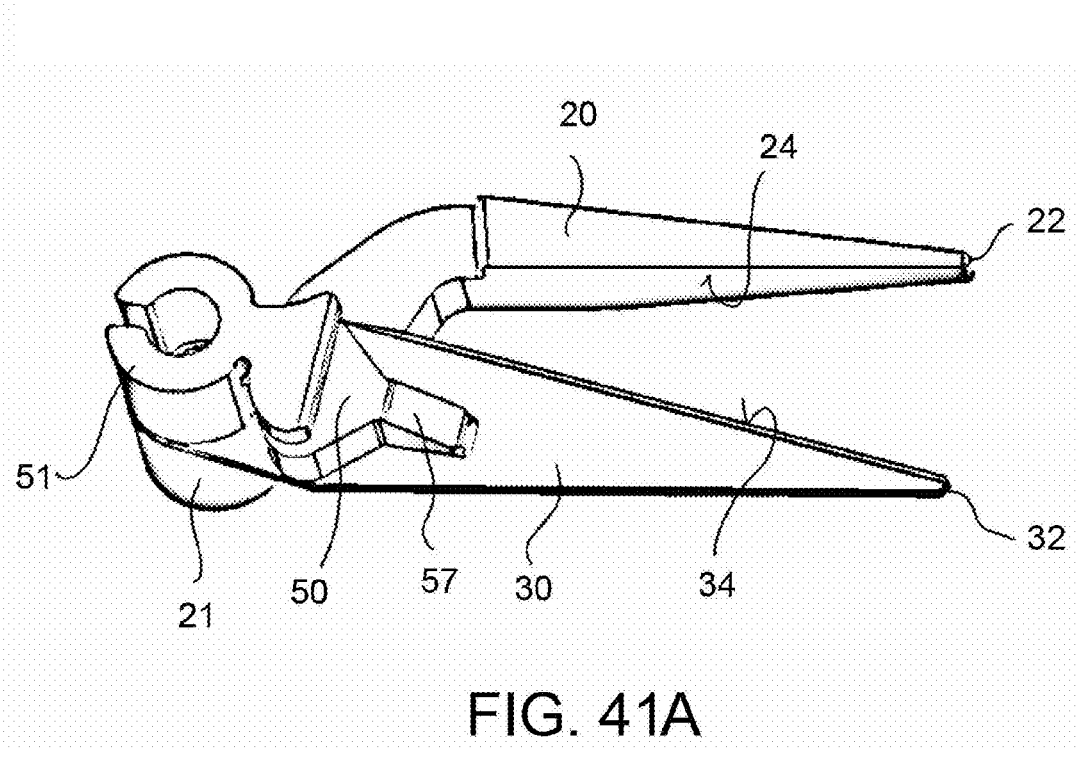
FIG. 41-A is an axonometric view of a portion of an end-effector of a surgical instrument of the surgical scissors type, according to an embodiment, in a closed configuration of the degree of freedom of opening/closing.
Figure 41B:
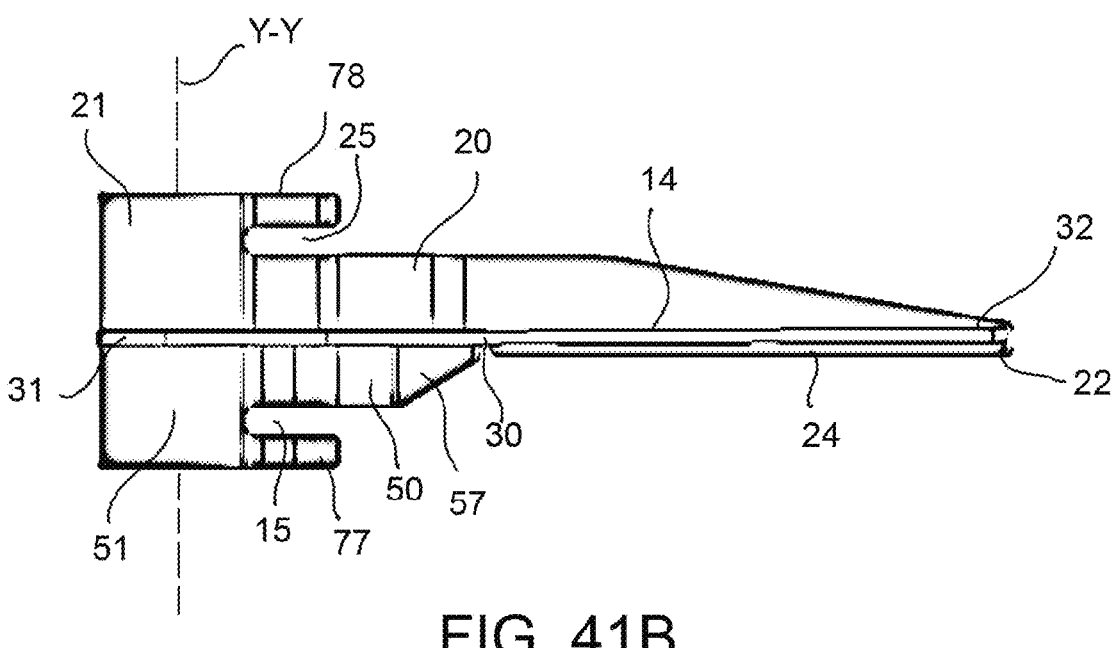
Figure 41C:
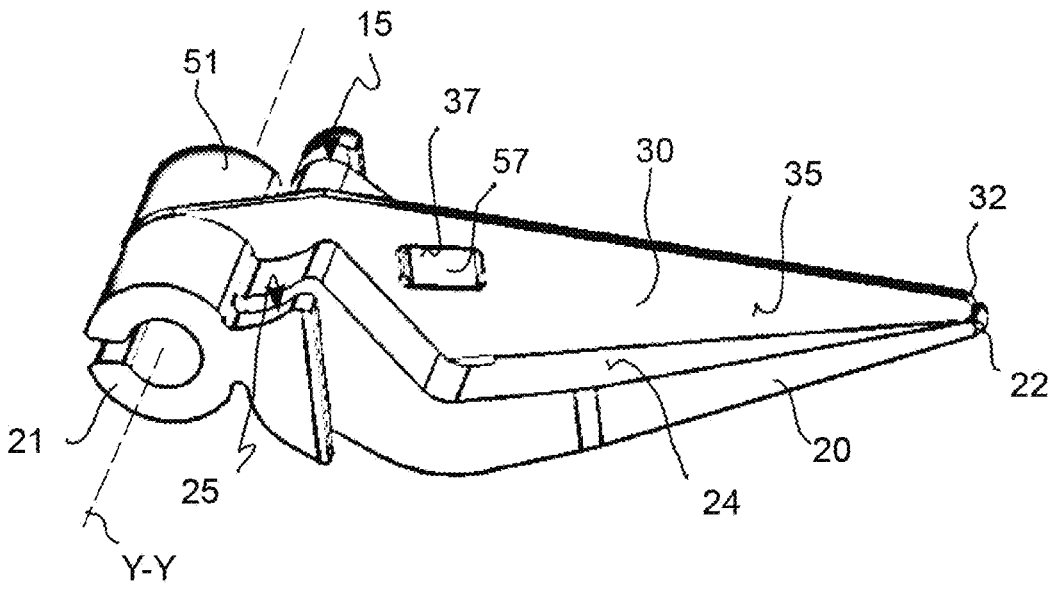
Figure 42:
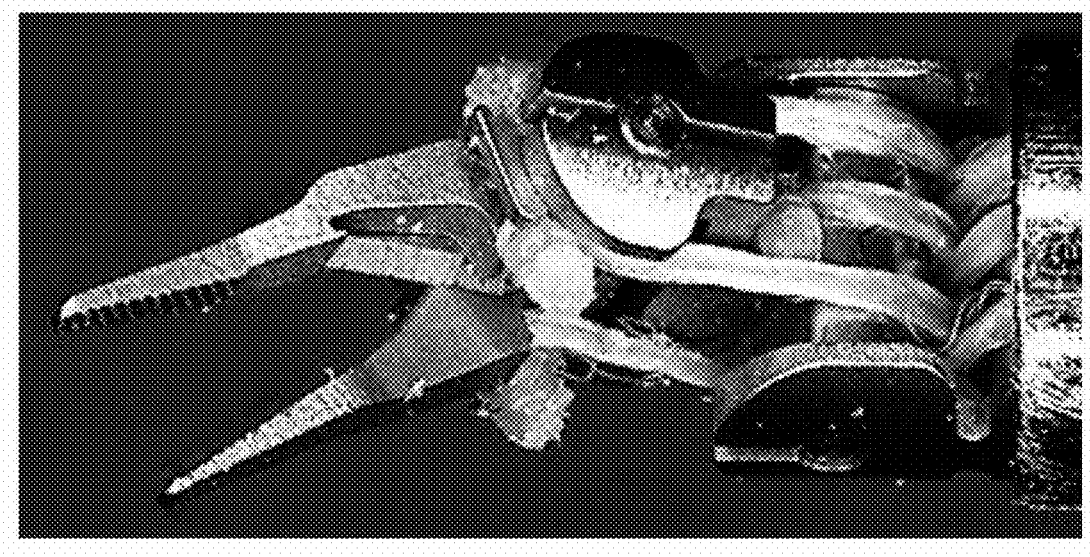
FIG. 42 is an electron microscope photographic image showing an articulated end-effector of a surgical instrument of the needle-driver/scissor type according to an embodiment.
Figure 43:
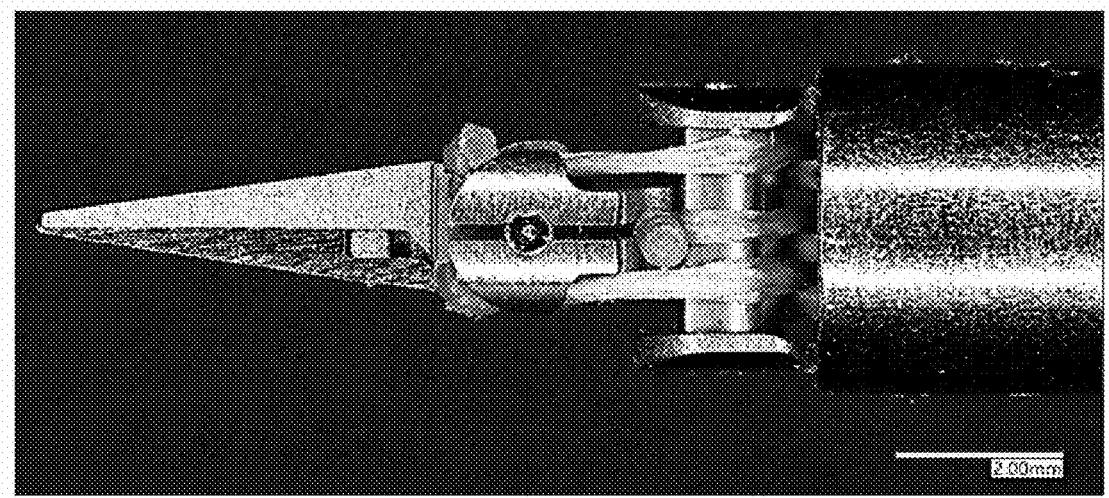
FIG. 43 is an electron microscope photographic image showing an articulated end-effector of a surgical instrument of the surgical scissors type, according to an embodiment, in which the scale of the image is shown at the bottom right ("2.00 mm").

In accordance with an alternative embodiment, shown for example in FIG. 41, the cutting action is performed with a blade 14 which acts as a hammer, abutting against the counter-blade which acts as an anvil.

Preferably, the cutting edge 34 of the blade link 30 is adapted to abut against said counter-blade portion 24 integral in rotation with said reaction link 20, during the movement of the degree of freedom of opening/closing G in a mechanical interference contact condition to exert a cutting action.

Preferably, the cutting edge 34 of the blade link 30 is elastically bendable in a direction parallel to the common distal rotation axis Y-Y. A blade portion 14 integral in rotation with the first termination seat 15 for the first pair of antagonistic tendons 71, 72 is elastically bendable in the axial direction and said counter-blade portion 24 is adapted to abut against said cutting edge 34, elastically bending the body of the blade link 30 in the axial direction. The blade portion 14 is a portion of the body of the blade link 30 comprising in a single piece said cutting edge 34 i.e., the cutting edge 34 belongs to the blade portion 14.

Thereby, the elasticity in an axial direction for obtaining the cutting action is provided at least partially by the elasticity of the blade portion 14, while the distal rotational joint 502 to which the root 31 of the blade link 30 is articulated, is axially rigid, i.e., it is not elastically loaded because relative displacements between the distal connecting portion 17 of the support link 2 and the roots 21, 31, 51 of the reaction, blade and blade holder links on the distal rotation axis Y-Y are avoided.

Therefore, said cutting edge 34 of the blade portion 14 of the blade link 30 and said counter-blade portion 24 integral in rotation with the reaction link 20 reach a mechanical interference contact condition to exert a cutting action.

The mechanical interference contact between the cutting edge 34 and the counter-blade portion 24 integral in rotation with the reaction link 20 which results in the cutting action simultaneously bendingly deforms the body of the blade link 30. The bending deformation of the blade portion 14 of the body of the blade link 30 during the cutting action is axially directed, i.e., it is directed substantially parallel to the common rotation axis Y-Y.

The counter-blade portion 24 preferably comprises a surface facing axially inwards adapted to form mechanical interference contact abutment with the cutting edge 34 of the blade link 30 for axially bending the blade portion 14 of the blade link 30. The reaction link 20 then exerts a reaction in the axial direction to the elastic bending of the blade link 30 during the cutting action. The body of the reaction link 20 can be elastically deformable.

The deformed configuration of the blade portion 14 when the blade link 30 and the reaction link 20 are in a substantially closed configuration is maximally bent, and in any case more bent than the configuration of the blade portion 14 when the blade link 30 and the reaction link 20 are in a partially closed and partially open configuration. Preferably but not necessarily, when the opening angle is maximally open and the blade portion 14 is free, the cutting edge 34 is straight and the blade link body 30 has a substantially planar configuration at least at the blade portion 14 thereof.

The at least one point of contact POC between the cutting edge 34 and the counter-blade portion 24 preferably varies in position and/or size as a function of the opening angle of the degree of freedom of opening/closing G and preferably tends to move in the distal direction as the opening angle is reduced, thereby accentuating the bending by elastic deformation of the body of the blade link 30.

"Point of contact POC" preferably means the most distal portion of the contact area between cutting edge 34 and counter-blade portion 24, although the contact area can be similar to a point in some configurations of an embodiment.

The elastically deformable bending cutting edge 34 can be sharp, i.e., it can be subjected to sharpening in order to have a locally reduced thickness as compared to the thickness of the body of the blade portion 14 and/or a sharp conformation in the cross-section thereof. For example, the cross-section of the blade link 30 has at the cutting edge 34 a pointed shape in which the faces of the blade portion 14 of the blade link form an angle to each other in the range 30°-60°. Preferably, the cutting edge 34 is sharpened so as to be flush with an axially facing blade surface 35 of the blade portion 14 of the blade link 30 which is placed axially facing the counter-blade portion 24. In other words, the blade portion

14 14 of the blade link body 30 comprises a blade surface 35 facing axially inwards and said cutting edge 34 forming the edge of the blade surface 35.

During the cutting action, the blade surface 35 of the blade link 30 can be in contact in at least one portion thereof with the counter-blade portion 24 integral in rotation with the reaction link 20, exchanging frictional forces directed substantially in the opening/closing direction G.

Preferably, the overall sliding friction force exchanged between each tendon and all the ruled surfaces of the links on which the tendon slides, when in operating conditions, is much lower (for example from one to three orders of magnitude lower) than the tensile force required by the tendons to achieve the elastic bending deformation of the blade portion 14 of the blade link 30 when the degree of freedom of opening/closing G is moved in closing to exert a cutting action, i.e., it is much lower than the mechanical interference contact friction force between the blade link 30 and the counter-blade portion 24. For this purpose, the tendons can be made of polymer material, and the links can be made of metallic material, and the convex ruled surfaces with parallel generator lines of the links can be smooth, to reduce the longitudinal sliding friction of the tendons on the links. For example, the ruled surfaces of the links are obtained by wire electro-erosion.

In accordance with an embodiment, said counter-blade portion 24 integral in rotation with the reaction link 20 comprises a curved protruding surface having a concavity facing axially inwards. Thereby, the protrusion of the counter-blade portion 24 is given by the curvature thereof having a concavity facing axially inwards.

In accordance with an embodiment, the counter-blade portion 24 integral in rotation with the reaction link 20 protrudes towards the rotational footprint of the blade link 30, to elastically bend the body of the blade link 30 when the counter-blade portion 24 is in mechanical interference contact with the cutting edge 34. In other words, the counter-blade portion 24 protrudes axially inwards. In accordance with an embodiment, said protruding of the counter-blade portion 24 accentuates towards the distal direction, i.e., away from the common rotation axis Y-Y along the longitudinal extension of the reaction link 20 and preferably said protruding is maximum close to or at the distal end 32 of the body of the blade link 30.

Preferably, the term "approaching rotational footprint" is meant to indicate the volume of space which can be occupied by the body of an element during the relative rotation movement of the closing of the degree of freedom of grip G.

Not necessarily the blade surface 35 is a flat portion, i.e., lying on a plane and can be a curved or arched portion, although in accordance with an embodiment it is a flat portion.

In accordance with an embodiment, the body of the blade link 30 has a two-dimensional main extension, i.e., lying on a preferably flat or arched lying surface, and has a substantially reduced thickness with respect to the extension on said preferably flat or arched lying surface.

In accordance with an embodiment, the cutting edge 34 is substantially straight in the preferably flat or arched lying surface, avoiding the provision of concavities in the lying surface of the body of the blade link 30.

Preferably, the thickness of the blade link 30 is significantly smaller than the thickness of the attachment root 51 of the blade holder link 50 and of the attachment root 21 of the reaction link 20, and is chosen so that the blade portion 14 of the body of the blade link 30 is elastically bendable when in operating conditions, transversely to the longitudinal extension of the cutting edge 34, and in particular in the direction of the thickness of the blade link 30. In particular, the body of the blade link 30 is preferably more bendable than the body of the reaction link 20, and preferably also more flexible than the body of the counter-blade portion 24. The flexibility of the blade link 30 and thus the flexibility of the cutting edge 34 is intended in the direction of the thickness thereof, i.e., in a direction orthogonal to the lying surface, whether flat or arched, of the blade link 30. For example, the blade link 30 has an arched, i.e., concave, conformation having a concavity facing in a direction exiting from/entering into the lying plane and in such a case the lying surface of the body of the blade link 30 is an arched surface as is the blade surface 35.

Not necessarily the blade link 30 and thus the cutting edge 34 must be elastically deformable in the lying surface, i.e., a bendability in a direction orthogonal to the thickness thereof is not necessarily included.

The ratio between the thickness of the body of the blade link 30 at the level of the blade portion 14 (excluding in this evaluation the thickness of the cutting edge 34, which as mentioned is preferably sharpened) and the thickness of the root 51 of the link 50 and/or the thickness of the second root 21 of the reaction link 20 can be between ⅕ and ¹⁄₂₀. In absolute value the thickness of the blade link 30 can be between 0.1 mm and 0.5 mm and in accordance with an embodiment substantially equal to 0.2 mm.

As mentioned above, the blade link 30 is integral in rotation with the blade holder link 50. Thereby, the cutting edge 34 is integral in rotation with a distal free end which can be formed by the body of the blade holder link 50 and/or the body of the blade link 30. In the case where the free end is formed by the body of the blade link 30 it can coincide with the distal end 32 of the blade link 30. Being elastically flexible, the cutting edge 34 can be elastically deformed with respect to the blade holder link 50 integral therewith in rotation when in operating conditions. The elastic deformation of the cutting edge 34 preferably occurs in a transverse direction with respect to the longitudinal extension direction of the body of the blade holder link 50, i.e., in a transverse direction with respect to the direction joining the proximal attachment root 51 and the free end integral in rotation to the cutting edge 34, in other words in the direction of the thickness of the body of the blade link 30.

In accordance with an embodiment, the blade link 30 is substantially planar when in a non-deformed configuration, i.e., it lies on a definable lying plane. The bending elasticity of the blade link 30 tends to bring the blade portion 14 back into said non-deformed planar configuration. Therefore, the blade surface 35 facing axially inwards can be parallel, and preferably also aligned for example seamlessly, to an axially facing internal contact surface 83 of the root 51 of the blade holder link 50. Preferably, the cutting edge 34 is straight when in a non-deformed condition, i.e., it extends substantially in a straight line parallel to, and preferably as a straight extension of, the axially facing internal contact surface 83 of the root 51 of the link 50. In other words, in accordance with an embodiment, the cutting edge 34 extends parallel to the definable lying plane of the blade link 30.

The cutting edge 34 can be aligned with the longitudinal extension direction X-X of the rod 7 in at least one operating configuration, for example in the case in which the shaft 7 is a straight and rigid shaft and the cutting edge 34 is out of contact with a protruding portion of the counter-blade portion 24.

In accordance with an embodiment, said counter-blade portion 24 can be made protruding in a direction which is transverse, preferably orthogonal, to the longitudinal extension of the reaction link body 20 and is also transverse, preferably orthogonal, to the common rotation axis Y-Y. The counter-blade portion 24 is not necessarily made sloping, even while protruding.

In accordance with an embodiment, said counter-blade portion 24 is a curved surface. Thereby, the counter-blade portion 24 protrudes due to the arched shape thereof. The concavity of the counter-blade portion 24 is preferably axially and internally facing, i.e., in a direction parallel to the common rotation axis Y-Y and facing the rotational footprint of the cutting edge 34.

The counter-blade portion 24 can act as a wedge to appropriately bend the cutting edge 34 and the body of the blade link 30 to exert the cutting action substantially along the entire longitudinal extension of the counter-blade portion 24.

The attachment root 31 of the blade link 30 when in operating conditions does not bend elastically, for example because it is rigidly interposed in an axial direction between the prongs 3, 4 of the support link 2 and has opposite contact surfaces 81, 82 in direct and intimate contact with respective opposite contact surfaces facing axially inwards of other links, such as a contact surface 83 of the root 51 of the blade holder link 50 and an opposite contact surface 84 of the root 21 of the reaction link 20. During the movement of the degree of freedom of opening/closing G there will be relative sliding with direct and intimate contact between the contact surface 84 facing axially inwards of the root 21 of the reaction link 20 and the contact surface 82 of the root 31 of the blade link 30. In accordance with a preferred embodiment, the attachment root 31 of the blade link 30 is axially interposed between the root 51 of the blade holder link 50 and the root 21 of the reaction link 20. Preferably, the contact surface 82 of the root 31 of the blade link 30 is axially aligned with the blade surface 35 and seamlessly joined thereto. In turn, the prongs 3, 4 of the distal connecting portion 17 of the support link 2 comprise opposite contact surfaces 87, 88 facing axially inwards which are in direct and intimate contact with surfaces 85, 86 facing axially outwards, in which preferably said surfaces 85, 86 facing axially outwards belong to the blade holder link 50 and reaction link 20. Where a further counter-blade link 40 is included, as explained below, it can comprise a root 41 thereof having two opposite contact surfaces of counter-blade links in direct and intimate contact, for example with a contact surface 82 of the blade link 30 and a contact surface facing axially inwards of the reaction link 20.

Such a pack arrangement of the roots 21, 31, 51 between the prongs 3, 4 of the distal connecting portion 17 of the support link 2 creates an axially rigid rotational joint Y, i.e., relative displacements between the roots 21, 31, 51 of the reaction links 20, 30, 50 in the direction of the common rotation axis Y-Y are avoided.

During the cutting action, the elasticity is at least partially provided by the elastic flexibility of the body of the blade link 30 in a blade portion 14 which is located distally with respect to the attachment root 31 of the blade link 30.

The axial distance Y5 in the direction parallel to the common distal rotation axis Y-Y between the first termination seat 15 of the root 51 of the blade holder link 50 and a surface 96 of said one or more convex ruled surfaces 96, 98 of the support link 2 is constant for any cutting condition.

Likewise, the axial distance Y5' in the direction parallel to the common distal rotation axis Y-Y between the second termination seat 25 of the root 21 of the further reaction link 20 and a surface 98 of said one or more convex ruled surfaces 96, 98 of the support link 2 is constant for any cutting condition.

I.e., as the opening angle of the degree of freedom of opening/closing G varies, the axial distance Y5, Y5' between a convex ruled surface 96, 98 of the support link 2 and a termination seat 15, 25 of the first or second pair of tendons 71, 72, 73, 74 remains the same.

In accordance with an embodiment, said first distance Y5 is zero i.e., the termination seat 15 is longitudinally aligned with a convex ruled surface 96 of the support link 2. In such a case, the actuation tendons 71, 72 of the blade holder link 50 can have respective distal paths parallel to each other. Similarly, in accordance with an embodiment, said second distance Y5' is zero i.e., the termination seat 25 is longitudinally aligned with a convex ruled surface 98 of the support link 2. In such a case, the actuation tendons 73, 74 of the reaction link 20 can have respective distal paths parallel to each other.

Since the axial distances Y5, Y5' remain unchanged in any cutting condition, i.e., no sliding is provided along the articulation pin 5 of the distal rotation axis Y-Y, such distances or other axial distances can be evaluated between different points of the articulated end-effector 9. In accordance with an embodiment, the attachment root 51 of the blade holder link 50 comprises a first surface 85 facing axially outwards, and in which the further root 21 of the further reaction link 20 comprises a second surface 86 facing axially outwards, and in which the distance Y8 in the axial direction between said first surface 85 of the attachment root 51 of the blade holder link 50 and said second surface 86 of the further attachment root 21 of the reaction link 20 is constant for any cutting condition. The surfaces 85, 86 can be flat surfaces orthogonal to the distal rotation axis Y-Y.

In accordance with a preferred embodiment, the axial distance Y5 between the first termination seat 15 of the root 51 of the blade holder link 50 and a surface 96 of said one or more convex ruled surfaces 96, 98 of the support link 2 is equal to the axial distance Y5' between the second termination seat 25 of the root 21 of the further reaction link 20 and a surface 98 of said one or more convex ruled surfaces 96, 98 of the support link 2.

Therefore, avoiding axial sliding along the articulation pin 5 between the roots, as well as between the roots and the prongs, keeps the geometric relationship between the ruled surfaces 96, 98 of the support link 2 on which the tendons 71, 72, 73, 74 of the first or second pair of tendons slide longitudinally to actuate the degree of freedom of opening/closing G, i.e., to exert the cutting action and the termination seats 15, 25 for the respective tendons made in a single piece with the root 51 of the blade holder link 50 or the root 21 of the reaction link 20, respectively, without thereby preventing the relative rotation between said links about the common distal rotation axis Y-Y.

In the direction parallel to the rotation axis the tendons do not slide with respect to the respective ruled surfaces thereof.

A rigid axially rotational joint 502 of a cutting joint is thus made. A blade having a cutting edge 34 and a counter-blade 24 which are integral in rotation with the axially rigid rotational joint 502 are provided, capable of jointly exerting a cutting action during the closing movement of the degree of freedom of opening/closing.

Therefore, it is possible to avoid the provision of elastic elements of the Belleville type fitted to the articulation pin 5 or otherwise interposed between the prongs 3, 4 of the distal portion 17 of the support link 2. In addition, the provision of an adjustment screw adapted to tighten the roots together in an axial direction is avoided.

Said axially rigid distal rotational joint 502 also allows the cutting edge 34 to be oriented by rotating it about the rotation axis of yaw Y-Y, allowing control over the adjustment of the cutting orientation.

Such a distal rotational joint 502 is axially rigid also for any orientation of the degree of freedom of yaw Y, i.e., for any movement of the assembly formed by the blade holder links 50, blade link 30 and reaction link 20 with respect to the distal portion 17 of the support link 2, as well as for any orientation of the degree of freedom of pitch P of the proximal rotational joint 509, i.e., for any movement of the assembly formed by the support link 2, and the blade holder links 50, blade link 30 and reaction link 20 with respect to the connection link 90 to the shaft. Preferably, the connection link 90 to the shaft is rigidly fixed to the distal end 8 of the rod 7, for example by means of a pair of pins 94, and in this case the degree of freedom of pitch P can be understood as an orientation of the support link 2 with respect to the shaft 7 particularly where the shaft 8 is a rigid shaft.

As mentioned above, in order to move the links of the articulated end-effector 9 about said common axes of proximal rotation P-P and/or distal Y-Y i.e., pitch P-P and/or yaw Y-Y to activate the degrees of freedom of the articulated end-effector 9, preferably the surgical instrument 1 comprises a plurality of pairs of antagonistic actuation tendons extending from the backend portion 104 to the articulated end-effector 9 through the shaft 9 and ending on at least some of the links of the articulated end-effector 9, as explained below.

In accordance with a preferred embodiment, the root 51 of the blade holder link 50 comprises in a single piece a first termination seat 15 which receives a first pair of antagonistic tendons 71, 72, and the root 21 of the reaction link 20 comprises in a single piece a second termination seat 25 which receives a second pair of antagonistic tendons 73, 74. Those skilled in the art will appreciate that in this preferred embodiment, each of said first and second pairs of antagonist actuation tendons comprises an opening actuation tendon 71, 73 and a closing actuation tendon 72, 74. By creating the terminating seats 15, 25 in a single piece with the respective link 20, 50, it is possible to keep the number of pieces minimized, facilitating assembly and favoring miniaturization. Furthermore, the root 31 of the blade link 30 is allowed to be made very thin, or at least thin as the bendable portion, elastically simplifying the creation of the blade link 30 and at the same time allowing a fine characterization of the mechanical properties thereof functional to the cutting action. In addition, in accordance with a preferred embodiment, each termination seat 15, 25 acts as a termination seat for both antagonistic tendons of the respective pair of antagonistic tendons, helping to keep the number of operations to be performed on each of the links 20, 50 minimized, favoring miniaturization. Therefore, the blade link 30 does not comprise any termination seat and is dragged in rotation by the blade holder link 50. Thereby, it is possible to keep the number of actuation tendons small, as well as to keep the number of termination seats to a minimum, thus favoring miniaturization.

In accordance with an embodiment, the first termination seat 15 of the blade holder link 50 and the second termination seat 25 of the reaction link 20 are each delimited by a cantilevered drag leg 77, 78 extending longitudinally from the respective root next to the body of the respective link. Each cantilevered leg 77, 78 is preferably made in a single piece with the respective link thereof and is proximally attached to the respective root 51, 21 and protrudes canti-levered longitudinally alongside the body of the blade holder link 50 or the body of the reaction link 20 respectively, forming a free end of the leg 77.1, 78.1. Thereby, each termination seat 15, 25 of the blade holder link 50 and the reaction link 20 are substantially radial slots, and preferably also longitudinal slots, having a radially-facing bottom wall formed by the respective attachment root.

Preferably, the extension of the cantilevered drag leg 77, 78 and of the respective adjacent portion of the body of the blade holder link 50 or of the reaction link 20 respectively is substantially identical, so as to face abutment and drag walls 15.1, 25.1 of the edge of the respective termination seat 15, 25 which are placed side by side at the same level in the opening/closing direction and which act as abutment and drag abutments for the respective tendon termination 70 of each actuation tendon 71, 72, 73, 74 of the pair of antagonistic tendons received in the first or second termi-nation seat 15, 25 respectively. The tendon termination 70 of each actuation tendon can be an enlarged portion, for example formed by a knot or a boss, which abuts against said abutment and drag walls 15.1, 25.1 of the edge of the respective termination seat 15, 25. In other words, said abutment and drag walls 15.1, 25.1 of the edge of each termination seat 15, 25 comprise edge walls which act as closing drag abutments, and opposite edge walls facing to be opposite which act as opening drag abutments. Therefore, abutment and drag walls 15.1, 25.1 of the termination seats 15 and 25 are arranged as an undercut for the respective tendon termination 70 in the respective termination seat 15, 25, and each termination seat 15, 25 is a through termination seat and preferably having an access opening facing longi-tudinally towards the free end of the respective link. There-fore, the distal portions of each actuation tendon 71, 72, 73, 74 of said first and second pairs of antagonistic tendons intersect, and/or overlap, in the respective termination seat 15, 25 to bring the respective tendon termination 70 to abut against the abutment and drag walls 15.1, 25.1 with respect thereto placed as undercut circumferentially to exert the dragging in rotation on the blade holder link 50 and/or on the reaction link 20 in the opening and/or closing direction of the degree of freedom of opening/closing G.

Therefore, in this case, said first axial distance Y5 can be defined as a distance in the direction of the rotation axis Y-Y between the first cantilevered leg 77 of the blade holder link 50 and a surface 96 of said one or more convex ruled surfaces 96, 98 of the support link 2, and such first axial distance is constant for any cutting condition. Likewise, in this case, said second distance Y5' can be defined as a distance in a direction parallel to the common distal rotation axis Y-Y between the second cantilevered leg 78 and a surface 98 of said one or more convex ruled surfaces 96, 98 of the support link 2 is constant for any cutting condition.

In accordance with a preferred embodiment, as mentioned above, the root 51 of the blade holder link 50 and the root 21 of the reaction link 20 each comprise at least one pulley surface 79, 80 facing opposite with respect to the common rotation axis Y-Y which laps the respective drag seat 15, 25 from circumferentially opposite sides and which can con-tinue inside the respective termination seat 15, 25 forming the bottom radially-facing wall, i.e., facing opposite with respect to the common rotation axis Y-Y, so that a distal portion close to the respective tendon termination 70 of each tendon of said first and second pairs of tendons 71, 72, 73, 74 winds about said at least one pulley surface 79, 80 when the tendon termination 70 abuts against the abutment and drag walls 15.1, 25.1 thereof of the respective termination seat 15, 25.

In accordance with a preferred embodiment, the at least one pulley surface 79 of the root 51 of the blade holder link 50 and the at least one pulley surface 80 of the root 21 of the reaction link 20 are all convex ruled surfaces with parallel generator lines and parallel to the common rotation axis Y-Y which do not comprise circumferential channels or grooves for guiding or retaining the tendons. The at least one pulley surface 79, 80 can be interrupted at a radial cutting channel 19, 29, where present.

Figure 6A:
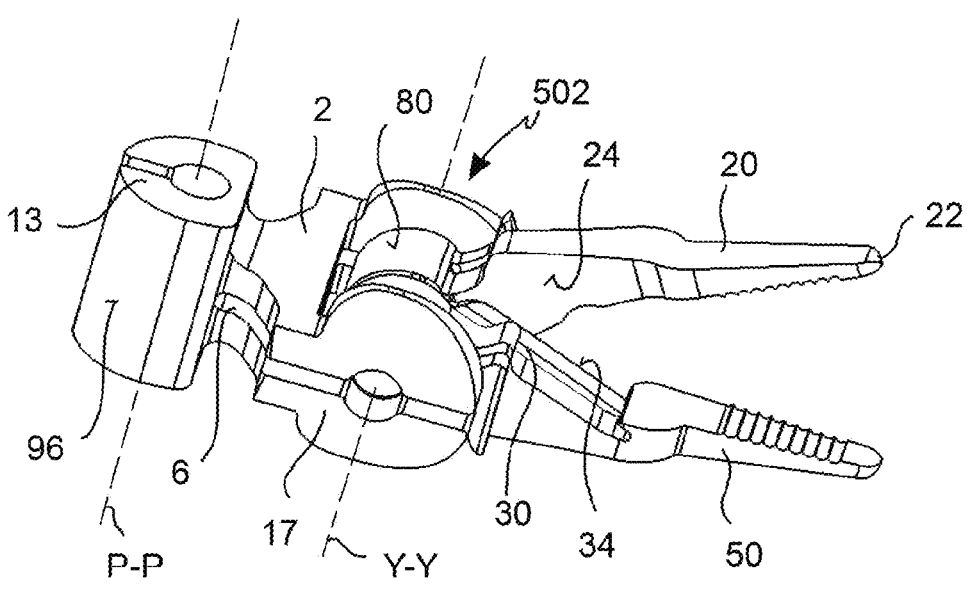
FIGS. 6-A and 6-B show an axonometric view of a portion of an end-effector of a surgical instrument of the needle-driver/suture-cutter type, according to an embodiment, with assembled parts and with separate parts, respectively.
Figure 6B:
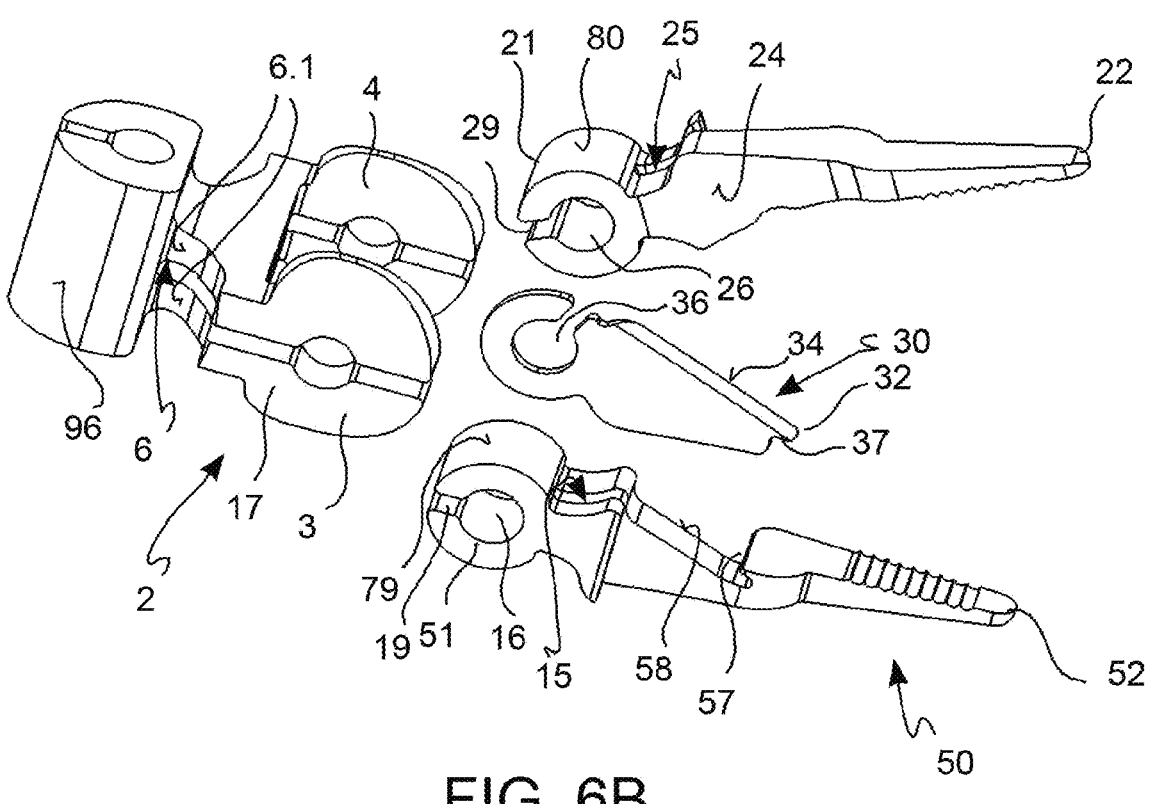
Figure 7A:
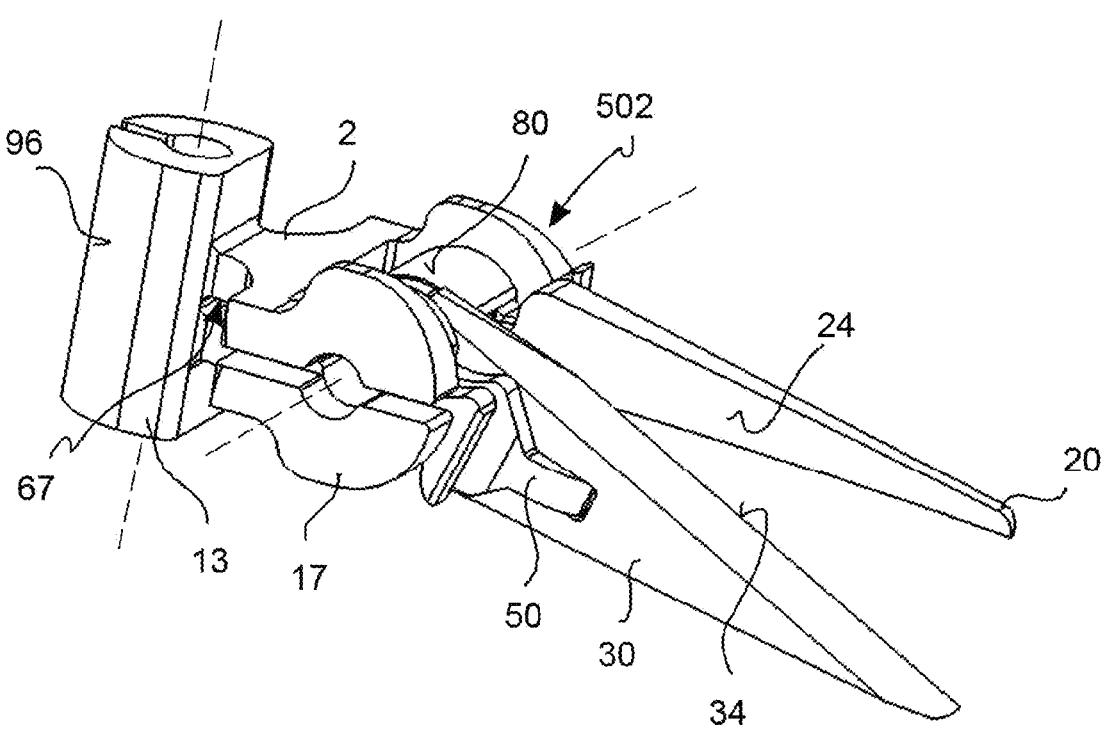
FIGS. 7-A and 7-B show an axonometric view of a portion of an end-effector of a surgical instrument of the surgical scissors type, according to an embodiment, with assembled parts and with separate parts, respectively.
Figure 7B:
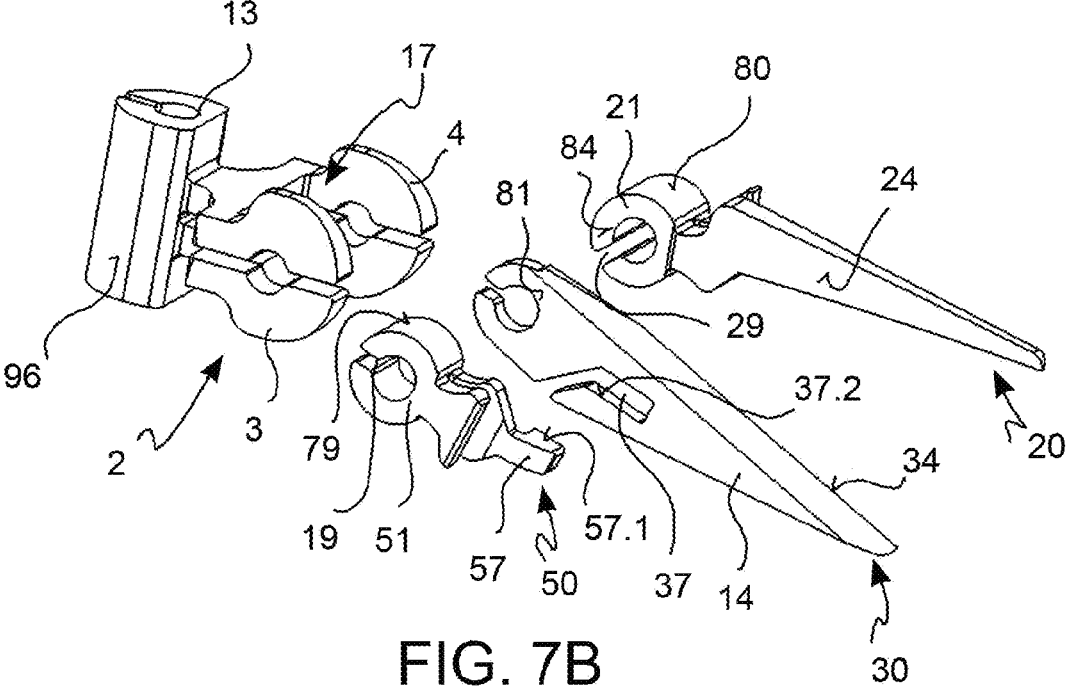
Figure 8A:
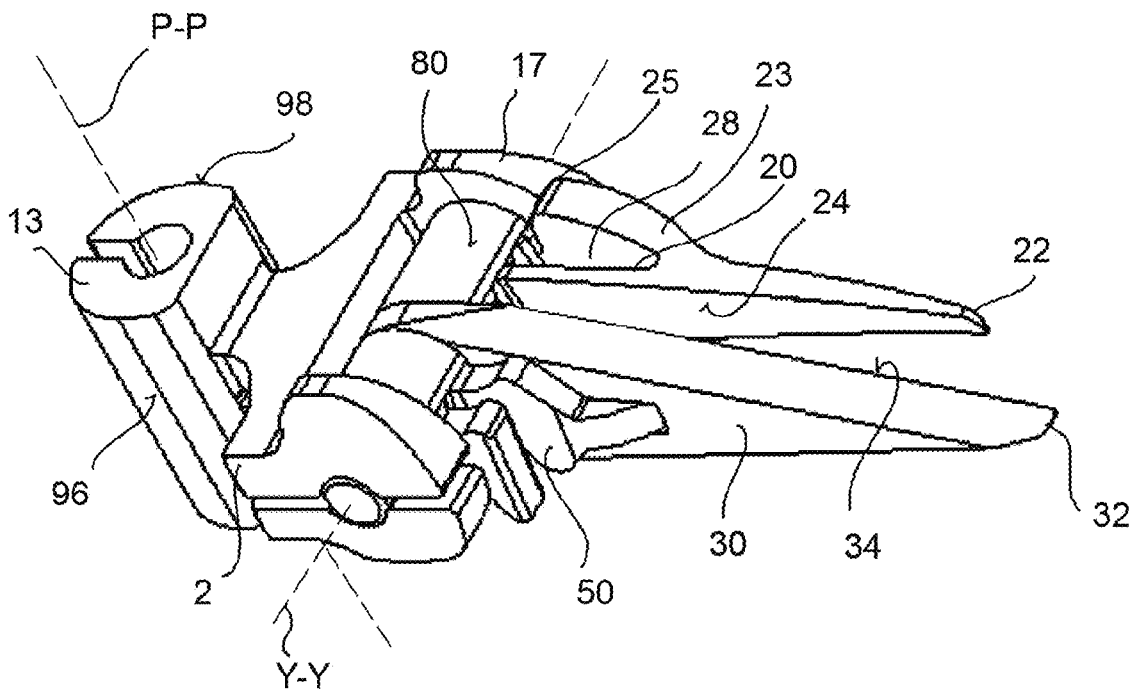
FIGS. 8-A and 8-B show an axonometric view of a portion of an end-effector of a surgical instrument of the surgical scissors type, according to an embodiment, with assembled parts and with separate parts, respectively.
Figure 8B:
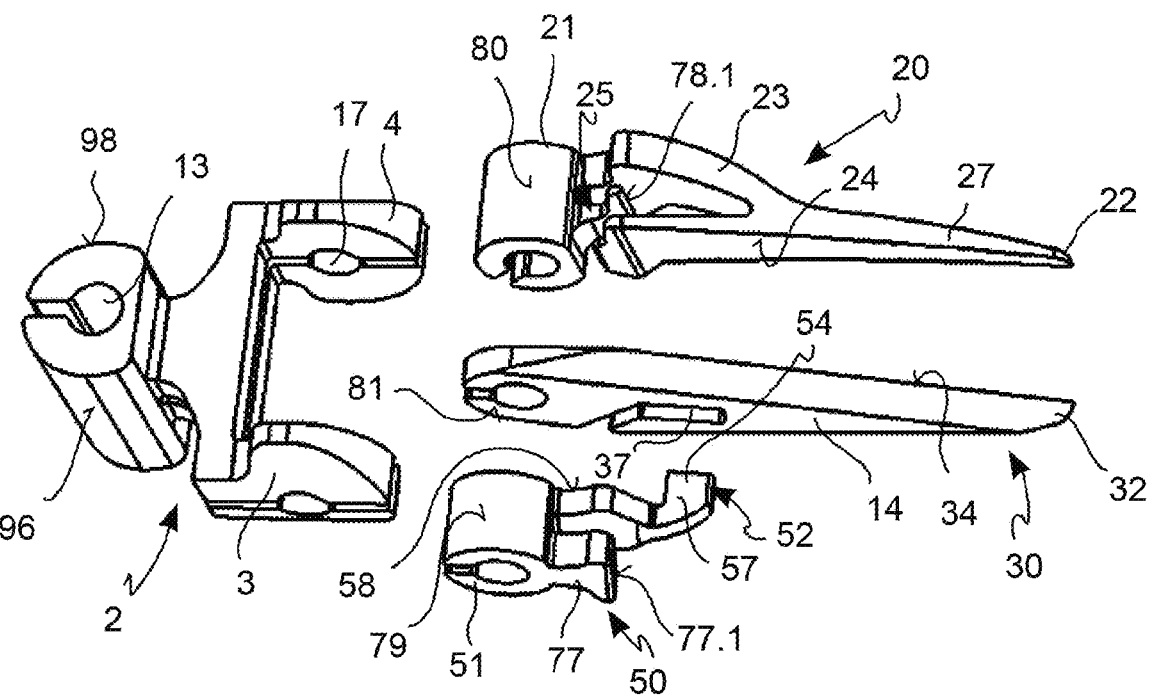

In accordance with an embodiment, the surgical instru-ment 1 further comprises a third pair of antagonistic tendons 75, 76 for moving the support link 2 about said common proximal rotation axis P-P. Therefore, the support link 2 can comprise at least a third termination seat 6 which receives the tendon terminations 70 of said third pair of antagonistic tendons 75, 76. In accordance with an embodiment as shown for example in FIGS. 6-A and 6-B, said at least a third termination seat 6 of the support link 2 is a single termina-tion seat passing directly axially, i.e., parallel to the common distal rotation axis Y-Y through the body of the support link 2, which forms abutment and drag walls 6.1 for the tendon terminations 70 placed as undercut for the respective actua-tion tendon 75, 76 of the third pair of tendons, similarly to what is explained above with reference to the first and second termination seats 15, 25. In accordance with an embodiment, the support link 2 comprises two separate and distinct third termination seats 6, one seat for each tendon 75, 76 of the third pair of antagonistic tendons.

In accordance with a preferred embodiment, the support link 2 comprises one or more convex ruled surfaces 96, 98 with parallel generator lines and all parallel to the common proximal rotation axis P-P, and the actuation tendons 71, 72, 73, 74 of the first and second pairs of antagonistic tendons slide longitudinally on said one or more convex ruled surfaces 84, 86 of the support link 2 during the actuation of the blade holder link 50 and/or the reaction link 20, in which said one or more convex ruled surfaces 96, 98 of the support link 2 do not comprise guide channels or grooves for receiving and guiding the tendons. The support link 2 can also comprise one or more convex ruled surfaces parallel to the common distal rotation axis Y-Y (not shown in the figure) on which the actuation tendons 71, 72, 73, 74 of the first and second pairs of antagonistic tendons slide longitu-dinally during the actuation of the blade holder link 50 and/or the reaction link 20.

The same one or more convex ruled surfaces 96, 98 with parallel generator lines and all parallel to the common proximal rotation axis P-P of the support link 2 can also act as a pulley surface for the actuation tendons 75, 76 of the third pair of antagonistic tendons. Said one or more convex ruled surfaces 96, 98 of the support link 2 extend on opposite sides of the support link 2. In accordance with an embodi-ment, the pulley surface for the actuation tendons 75, 76 of the third pair of antagonistic tendons is formed by the internal surface of the termination seat 6 of the support link 2.

In accordance with an embodiment, the link 97, 99 comprises one or more convex ruled surfaces 71, 72, 73, 74, 75, 76 with parallel generator lines and all parallel to the common proximal rotation axis P-P, in which the actuation tendons 97, 99 of said first, second and third pairs of antagonistic tendons slide longitudinally on said one or more convex ruled surfaces 90 of the link 90. Said one or more convex ruled surfaces 97, 99 of the connection link 60 extend on opposite sides of the connection link 90, and between the connection link 90 and the support link 2 the tendons 71, 72, 73, 74, 75, 76 of each of said first, second and third pairs of antagonistic tendons mutually cross to slide or wrap without sliding on the one or more convex ruled surfaces 96, 98 of the support link 2 facing to be opposite to the ruled surface 97, 99 of the connection link 90 on which they slide proximally. For example, said one or more convex ruled surfaces 96, 98 of the support link 2 are interposed between the prongs 91, 92 of the link 90 and are oriented to be opposite to the common proximal rotation axis P-P.

The ruled convex surfaces 79, 80, 96, 97, 98, 99 with parallel generator lines of the links in sliding or winding contact with the tendons 71, 72, 73, 74, 75, 76 are preferably all external surfaces for the respective link.

The actuation tendons 71, 72, 73, 74, 75, 76 are preferably polymer tendons formed by intertwined polymer fibers. For example, said intertwined polymer fibers comprise high molecular weight polyethylene (UHMWPE) fibers.

In accordance with a preferred embodiment, the group formed by said root 51 of the blade holder link 50, said root 31 of the blade link 30 and said root 21 of the reaction link 20 is globally interposed between said two prongs 3, 4 of the support link 2 and in direct and intimate contact therewith. Thereby, relative movements between the roots and between each root and the prongs are avoided, and therefore where the articulation pin 5 is included, relative sliding along the articulation pin 5 between the roots and the prongs are avoided during the elastic deformation of the blade link 30. In other words, the roots and the prongs are preferably next to and in direct and intimate contact with one another and there are no elastic reactions therebetween, even if distally, i.e., at a certain longitudinal distance with respect to the common rotation axis Y-Y the geometric conformation of the respective links imposes that the rotational approaching dimensions of the respective links can overlap and/or interfere, as for example can occur for the cutting interference contact between the cutting edge 34 of the blade link 30 and the counter-blade portion 24 integral in rotation with the reaction link 20.

By virtue of such a package arrangement of the roots, a reaction is provided to the elastic bending of the blade body during the cutting action, meanwhile avoiding the provision of elements which exert an elastic action between the roots, consequently simplifying the assembly and favoring an extreme miniaturization.

By virtue of such a pack arrangement of the roots, impingements of the root 31 of the blade link 30, which is preferably thinner than the articulation pin 5 are avoided so as to provide a satisfactory certainty of positioning the cutting edge 34 with respect to the counter-blade portion 24 for each opening angle of the degree of freedom of grip G, thus providing extreme cutting precision.

The roots preferably have a cylindrical geometry about the common rotation axis Y-Y, and where the third root 31 has a substantially smaller thickness than the first root 11 and the second root 21, the third root 31 has a discoidal-type cylindrical geometry. Similarly, this can apply to the fourth root 41 of the counter-blade link 40, if included.

Although the manufacture of the pieces by means of a wire electro-erosion process allows obtaining boosted tolerances, minimum local micro-clearances can be included in the direction of the common rotation axis Y-Y of the order of a fraction of a tenth of a millimeter between at least some of said contact surfaces of the roots and/or the prongs to ensure a direct and intimate contact and at the same time allow the relative rotation about the common rotation axis Y-Y during the actuation of the degree of freedom of opening/closing G and/or yaw Y. The articulation pin 5 can be in interference, i.e., integral in rotation with at least one of said roots and/or said prongs.

In particular, as a consequence of the fact that the support link 2, the blade holder link 50, the blade link 30 and the reaction link 20 are made in separate pieces, in any case a minimum micro-clearance in the axial direction is necessarily included, i.e., in the direction of the common rotation axis Y-Y between the respective contact surfaces, and globally said micro-clearance is in accordance with an embodiment in a range between ¹⁄₂₀ and ⅕ of the thickness of the root 31 of the blade link 30 and is divided, i.e., distributed locally between the contact surfaces of the prongs 3, 4 of the support link 2 and of the roots of the respective links, where the contact surfaces of the prongs and of the roots respectively of the blade holder link 50 and of the reaction link 20 are made by wire electro-erosion (WEDM).

Therefore, the wording "direct and intimate contact" also intends to indicate the embodiments in which a minimum micro-clearance is in any case included between at least some of, but also all, the contact surfaces of the prongs and of the roots of the respective links. During the cutting action and in particular for relatively high opening angles of the degree of freedom of opening/closing G (e.g., angle greater than 20°-30°), the mechanical interference contact between the cutting edge 34 of the blade link 30 and the counter-blade portion 24, therefore, can generate a minimum micro-displacement of the order of a hundredth of a millimeter of the root 31 of the blade link 30 along the articulation pin 5.

For example, from an analysis conducted by the inventors, it emerges that in accordance with an embodiment the thickness of the root 31 of the blade link 30 is about 0.2 mm and the overall micro-clearance in the direction of the common rotation axis Y-Y which is, in operating conditions, distributed locally between the contact surfaces of the prongs and the roots of the respective links is globally about 0.02 mm, and that when in operating conditions the local micro-clearance in the direction of the common rotation axis Y-Y between the root 31 of the blade link 30 and the root 21 of the reaction link 20 is about 0.01 mm, i.e., substantially equal to ¹⁄₂₀ of the thickness of the root 31 of the blade link 30.

By virtue of the fact that the support link 2 with two prongs 3, 4, the root 51 of the blade holder link 50, the root 21 of the reaction link 20 and the root 31 of the blade link 30 are made in separate pieces imposing both a minimum clearance in the direction of the common rotation axis Y-Y as explained above, it allows maneuvering in opening/closing rotation said degree of freedom of opening/closing G in a precise and controlled manner both in the opening and closing direction, at the same time exerting the cutting action.

In accordance with a preferred embodiment, said root 51 of the blade holder link 50 comprises a first through hole 16, and said root 21 of the reaction link 20 comprises a second through hole 26, and said root 31 of the blade link 30 comprises a third through hole 36, in which said first through hole 16 of the root 51, and said second through hole 26 of the root 21, and said third through hole 36 of the root 31 are aligned in axis with said common rotation axis Y-Y. In accordance with an embodiment, a articulation pin 5 is received inside said first, second and third through holes 16, 26, 36. In this case, said articulation pin 5 can be made as a cantilevered leg in a single piece with one of the prongs 3, 4, or it can be made in two pieces in the form of two opposite and aligned cantilevered legs each in a single piece with one of the prongs 3, 4 of the support structure, although in accordance with a preferred embodiment the articulation pin 5 is a separate piece both with respect to the roots 51, 21, 31, and with respect to the prongs 3, 4. In accordance with an embodiment, each of the two prongs 3, 4 comprises a through hole of the prong aligned in axis with said common rotation axis Y-Y and aligned with each and all of said first, second and third through holes 16, 26, 36.

In accordance with an embodiment, said first through hole 16 of the root 51, and said second through hole 26 of the root 21, and said third through hole 36 of the root 31 are all circular through holes and coaxial to said common rotation axis Y-Y and receive a single articulation pin 5 extending in the direction of the common rotation axis Y-Y from a first prong 3 of the distal connecting portion 17 of the support link 2 to a second prong 4 of the distal connecting portion 17 of the support link 2. In accordance with an embodiment, said first through hole 16 of the first root 51, and said second through hole 26 of the second root 21, and said third through hole 36 of the third root 31 all have substantially the same diameter and receive said articulation pin 5 in direct and intimate contact for the entire circumferential extension of the respective hole edge.

The provision of said third circular through hole 36 of the root 31 of the blade link 30 in direct and intimate contact with the articulation pin 5 for the entire circumferential extension of the hole edge thereof, allows exerting a reaction to the cutting action exerted by the cutting edge 34 of the blade link 30. In particular, during the cutting action the opening angle of the degree of freedom of grip G is progressively reduced, resulting in a mechanical interference contact between the cutting edge 34 (and preferably also the blade surface 35) of the blade link 30 and the counter-blade portion 24 integral in rotation with the reaction link 20, and therefore a direct friction force in the opening direction is generated on the cutting edge 34 (and preferably also on the blade surface 35) of the body of the blade link 30 in contact with the counter-blade portion 24 which is balanced by a reaction to the friction of the cutting action exchanged in a portion of mutual contact between the hole edge of the third through hole 36 of the root 31 of the blade link 30 and the articulation pin 5. The friction reaction of the cutting action is preferably directed substantially along a radial direction with respect to the common rotation axis Y-Y. The reaction to the friction of the cutting action preferably affects an arc surface 38 of the thickness of the hole edge of the third circular through hole 36 of the root 31 of the blade link 30 facing the through hole 36.

Where at least some, but also all, of the through holes of the roots are made by wire electro-erosion (WEDM), a radial cutting channel 19, 29, 39 is provided on the respective root between the hole edge and the external edge of the respective root as an effect of the continuous cutting path of the cutting wire used for making the through holes by wire electro-erosion. Preferably, the arrangement of the radial cutting channel on the respective root is studied based on the static or dynamic behavior of the respective link, when in operating conditions. In particular, in accordance with a preferred embodiment, the cutting channel 39 of the root 31 of the blade link 30 is radially offset with respect to the cutting channel 29 of the root 21 of the link 20 to prevent the edges of the cutting channels from interlocking with each other during the opening/closing action.

In accordance with an embodiment, the through hole of each of said two prongs 3, 4 of the distal connecting portion 17 of the support link 2 is a circular through hole coaxial to said common rotation axis Y-Y. Where the prongs 3, 4 are made by wire electro-erosion, at least one radial channel between the hole edge and the external edge of the respective prong can be included on the prong.

As mentioned above, said articulated end-effector 9 of the surgical instrument 1 further comprises a blade link 30 comprising in a single piece a third proximal attachment root 31 and a cutting edge 34 elastically deformable by bending which can be sharpened, i.e., it can be subject to sharpening to have a locally reduced thickness with respect to the thickness of the body of the blade link 30 and/or a sharp conformation in cross-section.

In accordance with an embodiment, said blade link 30 is made by shaping, i.e., by cutting, suitably a substantially flat elastic sheet or strip. For example, the elastic sheet or strip can be made of steel for blades and shaped by wire electro-erosion (WEDM) and/or photo-etching and/or laser cutting and/or chemical etching. Preferably, the elastic sheet or strip is sharpened on one edge thereof to form the cutting edge 34 of the blade link 30. The sharpening can be carried out by wire electro-erosion (WEDM) and/or grinding, for example stone or diamond grinding. In accordance with an embodiment, one or more edges of the shaped sheet or strip are sharpened by wire electro-erosion (WEDM) in a step in which the cutting wire flows in an inclined direction, non-orthogonal to the lying plane of the sheet or strip.

In accordance with an embodiment, the body of the blade link 30 has a two-dimensional main extension, i.e., lying on a preferably flat or arched lying surface, and has a substantially reduced thickness with respect to the extension on said preferably flat or arched lying surface.

In accordance with an embodiment, the cutting edge 34 of the blade link 30 is substantially straight in the preferably flat or arched lying surface, avoiding the provision of concavities in the lying surface of the body of the blade link 30.

Preferably, the thickness of the blade link 30 is significantly smaller than the thickness of said links 20, 50 and is chosen so that the blade is elastically bendable when in operating conditions transversely to the longitudinal extension of the blade link 30, i.e., in the direction of the thickness. In particular, the blade link 30 must be more bendable than the reaction link 20 and preferably also more bendable than the blade holder link 50. The flexibility of the blade link 30 and thus the flexibility of the cutting edge 34 of the blade link 30 is intended in the direction of the thickness thereof, i.e., in a direction orthogonal to the blade link lying surface. Such a lying surface of the body of the blade link 30 can substantially correspond to the lying plane of the starting metal strip or sheet which suitably processed forms the blade link 30, even though in accordance with a possible embodiment the body of the blade link 30 is forced to have an arched, i.e., concave, conformation having a concavity facing in a direction exiting from/entering the lying plane of the starting elastic strip or sheet and in this case the lying surface of the blade link body will be an arched surface.

Not necessarily the blade link 30 and thus the cutting edge 34 of the blade link 30 must be elastically deformable in the lying surface, i.e., a bendability in a direction orthogonal to the thickness thereof is not necessarily included.

The material of the blade link 30 can be a different material with respect to the material of the support link 2, reaction link 20 and/or blade holder link 50. For example, the blade link 30 can be made of steel for blades. One or more surface treatments can be included on the blade link 30, for example coatings and/or heat treatments, for example to make the cutting edge 34 harder and more resistant to wear when in operating conditions. In accordance with an embodiment, the cutting edge 34 comprises a surface treatment at least on the surface 35 intended to work by mechanical interference contact against a counter-blade when in operating conditions.

The blade link 30 can be subjected to bending for example by press-bending. Curving by press-bending can provide the blade link 30 with the desired elastic properties, for example the blade link 30 can be bent towards the counter-blade axially to locally modify the mechanical interference action.

The ratio between the thickness of the blade link 30 at the level of the root 31 thereof (excluding in this evaluation the thickness of the cutting edge 34, which as mentioned is preferably sharpened) and the thickness of the root 51 of the blade holder link 50 and/or the thickness of the root 21 of the reaction link 20 can be between ⅕ and ½o. In absolute value, the thickness of the blade link 30 can be between 0.1 mm and 0.5 mm and in a preferential form between 0.1 and 1 mm.

As mentioned above, the support link 2, the blade holder link 50, the blade link 30 and the reaction link 20 are made in separate pieces, and preferably are formed by four separate pieces articulated in a common rotation axis Y-Y i.e., constrained to rotate with respect to a common rotation axis Y-Y, or common rotation axis of yaw Y-Y. In an embodiment, the articulated end-effector 9 consists of exactly said four pieces (i.e., said four links 2, 20, 30, 50) articulated together in said common axis Y-Y, plus a further piece which is a articulation pin 5 defining said common axis Y-Y, plus said further connection link 90 with the shaft 7 which is articulated with respect to the support link 2 in the common proximal rotation axis of pitch P-P by means of a further proximal articulation pin 93 defining said common proximal rotation axis of pitch P-P (in total seven pieces; the actuation tendons are excluded from the count). By virtue of this embodiment, where the common rotation axis of pitch P-P is non-parallel (preferably orthogonal) to the common rotation axis of yaw Y-Y, it allows obtaining a articulated cuff at the distal end of the rod 7 and where the rotation axis of pitch P-P is non-parallel and preferably orthogonal to the common rotation axis of yaw Y-Y, the articulated cuff is provided with the degrees of freedom of pitch, yaw and grip G, in which the degree of freedom of grip G is adapted to manage gripping and cutting. Where the connection link 90 is made in a single piece with the distal end 8 of the rod 7 (not shown in the figure), the articulated end-effector 9 will still be formed by said seven pieces which are: the distal end 8 of the rod 7, the support link 2, the blade link 30, the blade holder link 50, the reaction link 20, and said two articulation pins 5, 93.

A degree of freedom of roll R integral with the shaft 7 and preferably also with the backend portion 104 can be provided, for example a degree of freedom of roll R which allows the entire surgical instrument 1 to be rotated about the longitudinal extension axis X-X of the rod 7.

Those skilled in the art will appreciate that minimizing the number of pieces greatly simplifies the assembly of the articulated end-effector 9 of the surgical instrument 1, making it suitable for an extreme miniaturization. In particular, avoiding the provision of elastic preload elements in the axial direction (such as Belleville-type elastic washers fitted on the articulation pin 5), i.e., in the direction of the common rotation axis Y-Y between the distal connecting portion 17 of the support link 2, allows simplifying the assembly of the pieces and therefore favors an extreme miniaturization of the articulated end-effector 9, as well as consequently of the cross-section of the rod 7, while ensuring a satisfactory strength and resistance to the stresses which can arise when in operating conditions.

In accordance with a preferred embodiment, at least one of the blade link 30 and the blade holder link 50 comprises a distal free end. The distal end 32 of the body of the blade link 30 can form the distal free end of the assembly formed by the blade link 30 and the blade holder link 50. Alternatively, the distal end 32 of the blade link 30 is rotationally constrained to the drag portion 57 of the blade holder link 50, acting as a drag engagement portion 37 of the blade link 30, i.e., the drag portion 37 of the blade link 30 can coincide with the distal end 32 thereof.

In accordance with an embodiment, the reaction link comprises a distal free end 22.

Figure 34:
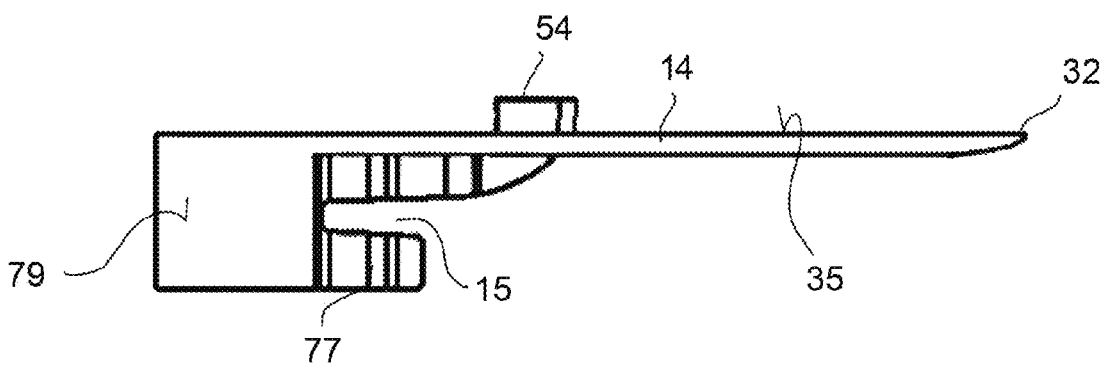
FIG. 34 shows a plan view of a link having in a single piece a blade portion and a termination seat for a pair of antagonistic tendons, according to an alternative embodiment.

In accordance with an alternative embodiment, the blade link 30 and the blade holder link 50 are made in a single piece and therefore the root 31 and the root 51 are made in a single piece, as shown for example in FIG. 34.

Surgical Instrument of the Surgical Scissor Type

With reference to the foregoing description of embodiments of the invention, said surgical instrument 1 can be a surgical scissor type instrument as shown for example in FIGS. 3, 5, 7-8, 11-12, 15, 30-40 and 43. Embodiments of said surgical instrument 1 will be described below, in which said surgical instrument 1 is a surgical scissor type instrument.

In accordance with a preferred embodiment, the distal end 32 of the blade link forms a distal free end.

Preferably, the counter-blade portion 24 is made in a single piece with the body of the reaction link 20.

In accordance with a preferred embodiment, the body of the reaction link 20 is also axially elastically bendable for exerting the cutting action. Therefore, during the cutting action, the mechanical interference contact between the cutting edge 34 of the blade link 30 and the counter-blade portion 24 of the reaction link 20 results in an axially externally directed elastic bending deformation of the blade link 30 and simultaneously results in an elastic bending deformation of the reaction link 20 also directed axially externally. It should be noted that the external axial direction of the blade portion 14 is intended as opposite the external axial direction of the reaction link 20.

Figure 35:
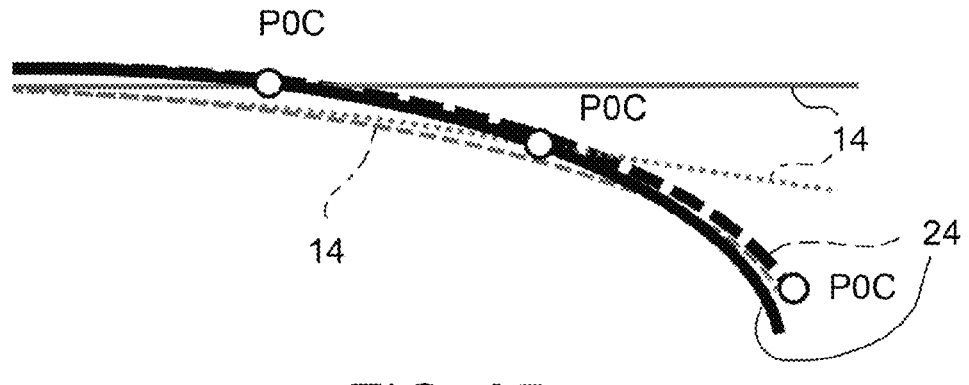
FIG. 35 is a diagram which diagrammatically shows a plan view of the conformation assumed by a blade portion and a counter-blade surface of the portion of the end-effector in FIG. 33 in various mechanical cutting interference configurations, according to an embodiment.
Figure 36:
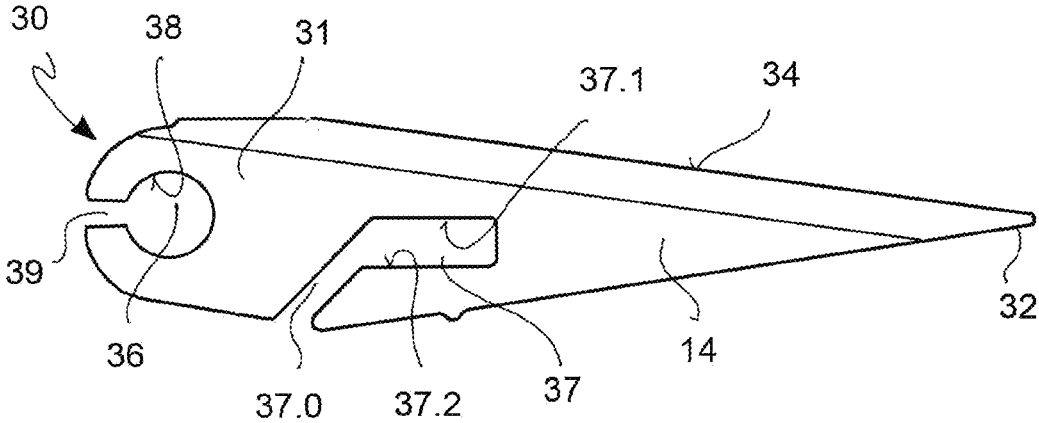
FIG. 36 is a vertical elevation view of a blade link in vertical elevation, according to an embodiment.

As shown for example in the diagram in FIG. 35, where the counter-blade portion 24 of the reaction link 20 is a curved protruding surface with concavity facing axially inwards, i.e., facing the blade link 30 in which the protrusion is accentuated distally close to or at the distal free end 22 of the reaction link 20, during the cutting action and preferably with small opening angles, i.e., less than a certain threshold for example less than 5°, the point of contact POC between the cutting edge 34 and the counter-blade portion 24 is close to the free ends 32, 22 and results in an elastic bending of the external axial blade link 30 with respect to the non-deformed configuration thereof and at the same time an elastic bending of the reaction link 20 with respect to the non-deformed configuration thereof. In other words, the blade link 30 and the reaction link 20 reach an equilibrium configuration for performing the cutting action at low opening angles in which both the body of the blade link 30 and the body of the reaction link 20 are both elastically bent in an external axial direction with respect to the respective non-deformed configuration.

As mentioned above, "point of contact POC" preferably means the most distal portion of the contact area between cutting edge 34 and counter-blade portion 24.

It should be noted that when the point of contact POC between the cutting edge 34 and the counter-blade portion 24 is in a more rearward position, i.e., more proximal with respect to the configuration described above, for example for opening angles of about 10°-25°, the configuration of the reaction link 20 can describe a more pronounced curvature than when the point of contact POC is close to or at the free distal end 22 (opening angles less than the threshold, for example less than 5° or less than 10°, because the reaction link 20 can be more rigid proximally and more bendable distally close to or at the free distal end 22, but this does not necessarily mean that the body of the blade link 30 is also deformed, i.e., bent, describing a more pronounced curvature than when the point of contact POC is close to or at the free distal end 22 of the reaction link 20 (opening angles less than the threshold, for example less than 50 or less than 10° because the curvature of the counter-blade portion 24 can be chosen so that it is more accentuated at the distal free end 22 of the reaction link 20. In accordance with a preferred embodiment, the body of the reaction link 20 is tapered longitudinally, resulting axially thinner as the distal free end 22 of the reaction link 20 is approached, so as to allow the bendability of the reaction link 20.

In accordance with an embodiment, the counter-blade portion 24 of the reaction link 20 is a curved protruding surface with concavity facing axially inwards, i.e., facing the blade link 30 in which the protrusion of the counter-blade portion 24 is accentuated distally close to or at the distal free end 22 of the reaction link 20 and also the body of the blade link 30 in the blade portion thereof with the cutting edge 34 is a curved protruding portion with concavity facing axially inwards, i.e., facing the counter-blade portion 24, in which the protrusion of the blade link 30 is accentuated distally close to or at the distal free end 32 thereof. In other words, in this embodiment, the blade surface 35 facing axially inwards of the blade link 30 is a concave protruding surface with concavity facing axially inwards, i.e., towards the counter-blade portion and the protrusion becomes accentuated distally close to or at the first free distal end 32 of the first tip 30. In this embodiment, also the cutting edge 34 preferably describes a curved path with a concavity facing axially inwards.

In accordance with an embodiment in which the blade link 30 and the blade holder link 50 further comprise respective drag engagement portions 37, 57 to make the blade link 30 and the blade holder link 50 integral in rotation, the drag engagement portion 57 of the blade holder link 50 is made as an internal axial protrusion 57, i.e., an axial ridge 57 extending axially internally comprising an opening drag surface 57.2 and an opposite closing drag surface 57.1, and in which the drag engagement portion 37 of the blade link 30 is made as an axially through slot 37 which receives said axial ridge 57 of the blade holder link 50, said axially through slot 37 delimited by an opening drag surface 37.2 in dragging contact with said opening drag surface 57.2 of the axial ridge 57 of the blade holder link 50 and an opposite closing drag surface 37.1 in dragging contact with said closing drag surface 57.2 of the axial ridge 57 of the blade holder link 50. Therefore, in this case, the axial ridge 57 of the blade holder link 50 can be inserted in the slot 37 of the blade link 30 by an inlet opening 37.0, and then runs through the inlet channel and is then rotated with respect to the blade link 30 so as to obtain the drag engagement. In other words, in this case, the blade 30 comprises an opening drag leg extending cantilevered in a longitudinal direction, for example directed proximally towards the common rotation axis Y-Y, and which does not work to obtain the cutting action, in which said cantilevered opening drag leg comprises said opening drag surface 37.2 and delimits the inlet opening 37.0 with an edge thereof.

The axial ridge 57 of the drag engagement of the blade holder link 50 can be obtained at the distal end 52 of the blade holder link 50. Thereby, the blade holder link 50 has a squat conformation with an enlarged and/or bent distal end 52 which forms said axial ridge 57.

Not necessarily, during the cutting action in which the blade link 30 elastically bends, the blade link 30 axially slides externally with respect to the axial ridge 57 of the blade holder link 50 because the bending deformation of the blade link 30 axially externally can occur only distally with respect to said drag engagement slot 37, the blade holder link 50 can comprise a surface 58 facing axially inwards between the root 51 thereof and the axial ridge 57 which is in contact with the blade link 30.

The position of the axial ridge 57 of the blade holder link 50 as well as the extension thereof in the internal axial direction can be chosen so that an axially internal portion of the axial ridge 57 with respect to the closing drag surface 57.1 forms a closing stroke end surface 54 for the second tip 20, adapted to receive in abutment a surface of the reaction link 20 acting as a closing stroke end for the degree of freedom of opening/closing G. Therefore, the axial ridge 57 of the blade holder link 50 can perform both the function of making the drag engagement with the blade link 30 and the function of making the closing stroke end abutment.

Preferably the closing stroke end surface 54 extends at a longitudinal level in which the cutting edge 34 is already present, i.e., the closing stroke end surface 54 extends axially cantilevered from the blade surface 35.

In accordance with an embodiment as shown for example in FIG. 34 in which the blade link 30 and the blade holder link 50 are made in a single piece forming a tip link, a closing stroke end abutment extending axially cantilevered from the blade surface 35 is provided.

The closing stroke end surface 54 preferably extends from the blade holder link 50 in the rotational approaching footprint of the reaction link 20.

Figures 37, 38:
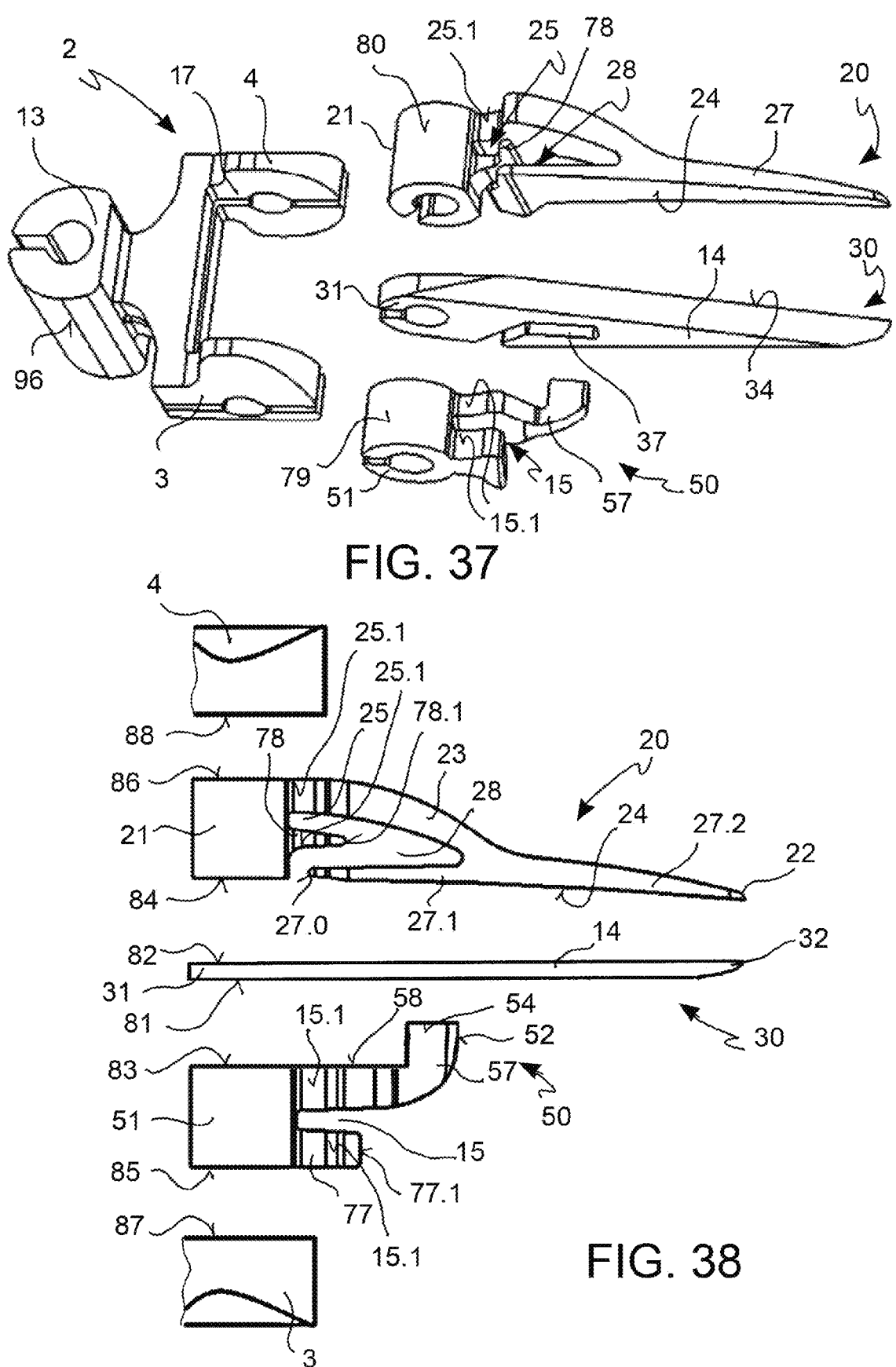
FIG. 37 shows an axonometric view with separate parts of a portion of an end-effector of a surgical instrument of the surgical scissors type, according to an embodiment.
FIG. 38 shows a plan view with separate parts of a portion of an end-effector of a surgical instrument of the surgical scissors type, according to an embodiment.

In accordance with an embodiment as for example shown in FIG. 38, the elongated body of the reaction link 20 is elastically bendable in the axial direction to exert the cutting action, in which the body of the reaction link 20 comprises a connecting stem 23 extending from the root 21 in the distal direction and ending in a cutting interface portion 27 of the body of the reaction link 20, in which said cutting interface portion 27 has a longitudinally and axially internally elongated body comprising two longitudinally opposite free ends and said counter-blade portion 24 therebetween. Preferably, the distal free end of the cutting interface portion 27 coincides with said distal free end 22 of the reaction link 20 and the opposite proximal free end 27.0 of the cutting interface portion 27 extends cantilevered towards the common rotation axis Y-Y, i.e., towards the root 21 of the reaction link 20. Thereby, the connecting stem 23 and the cutting interface portion 27 of the reaction link 20 form a sort of "T" structure in which two cantilevered arms 27.1 and 27.2 protrude longitudinally opposite from the distal top of the connecting stem 23 of the cutting interface portion 27 each having a free end, and in which the counter-blade portion 24 belongs to both arms 27.1 and 27.2 of the cutting interface portion and faces opposite with respect to the connecting stem 23.

Thereby, a counter-blade deformation seat 28 is formed between the proximal arm 27.1 of the cutting interface portion 27 and the connecting stem 23 to receive the axial deformation of the counter-blade portion 24, i.e., of the proximal arm 27.1 of the cutting interface portion 27 with the proximal free end 27.0 thereof. In accordance with an embodiment, the second termination seat 25 for the second pair of antagonistic actuation tendons 73, 74 is placed axially between the connecting stem 23 and the proximal arm 27.1 of the cutting interface portion 27. In accordance with an embodiment, the distal cantilevered leg 78 of the second termination seat 25 extends distally cantilevered between the connecting stem 23 and the proximal arm 27.1 of the cutting interface portion 27, so that the connecting stem 23 axially externally delimits the second termination seat 25 of the reaction link 20 and so that the distal cantilevered leg 78 of the second termination seat 25 axially externally delimits at least a portion of the counter-blade deformation seat 28. In accordance with an embodiment, the second termination seat 25 opens into said counter-blade deformation seat 28 and therefore in this embodiment the antagonistic actuation tendons 73, 74 can be inserted in the respective second termination seat 25 which opens in the distal direction, after having axially inserted them in the opening formed between the proximal free end 27.0 of the proximal arm 27.1 of the cutting interface portion 27 and the root 21 and after having moved them inside the counter-blade deformation seat 28 in a distal direction along the axially internal portion of the cantilevered leg 78 to then insert them in the inlet in the second termination seat 25, and thus in this embodiment the assembly of the antagonistic actuation tendons 73, 74 is preferably performed when the reaction link 20 and the blade link 30 form an opening angle (e.g., opening angle of about 90°) such that the counter-blade portion 24 of the proximal arm 27.1 of the body of the reaction link 20 is out of contact with the cutting edge 34 of the blade link 30, freeing the axial access at the opening formed between the proximal free end 27.0 and the root 21.

By virtue of the provision of such a reaction link 20 comprising said connecting stem 23 ending in said cutting interface portion 27, in which said counter-blade portion 24 belonging to said cutting interface portion 27 and having a proximal arm 27.1 with a proximal free end 27.0 and a longitudinally opposite distal arm 27.2 having a distal free end coincident with said second free end of the reaction link 20, it is possible to create an elastically bendable reaction link 20 in an external axial direction along substantially the entire longitudinal extension of the counter-blade portion 24, thus allowing exerting a precise cutting action also for high opening angles, for example opening angles in the range 25°-60° and preferably in the range 28°-58°, which correspond to a situation in which the point of contact POC belongs to said proximal arm 27.1 of the cutting interface portion, and preferably is close to or at the proximal free end 27.0 of the cutting interface portion 27. In this case and at high opening angles, the blade of the blade link 30 does not necessarily elastically bend to exert the cutting action and the elasticity can only be provided by the reaction link 20. In particular, in accordance with an embodiment, when the point of contact POC is at the proximal free end 27.0 of the proximal arm 27.1 the opening angle is about 58° and a cutting action is still exerted.

Therefore, by virtue of the provision of such a reaction link 20 comprising said connecting stem 23 ending in said cutting interface portion 27, it is possible to create a solution adapted to make a precise cut for opening angles in the range 0°-60°, while minimizing the actuation forces at the blade holder link 50 or at the reaction link 20 exerted by tensile action on the respective actuation tendons, and meanwhile allows keeping minimized the radius of the pulley surface

79, 80 of the respective root 51, 21 at tendon termination 15, 25, thus simultaneously allowing extreme miniaturization.

Figure 39A:
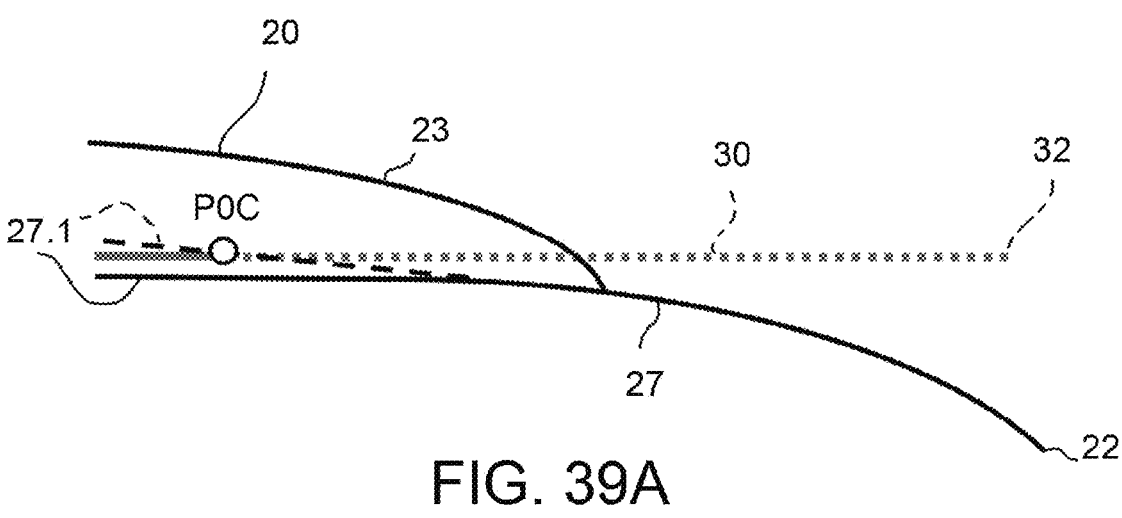
FIGS. 39-A, 39-B and 39-C are diagrams which diagrammatically show in view the conformation assumed by a blade portion and a counter-blade surface of the portion of the end-effector in FIG. 38 in various mechanical cutting interference configurations, according to an embodiment.
Figure 39B:
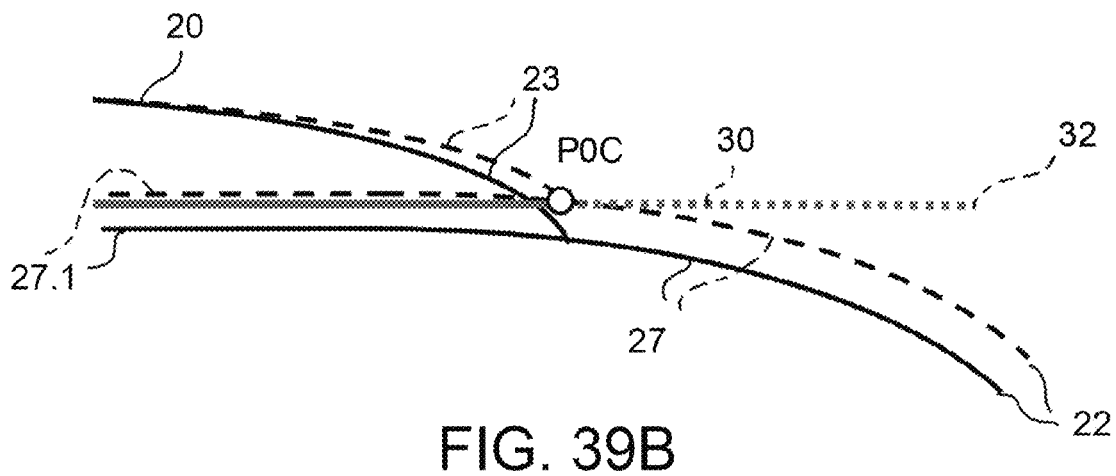
Figure 39C:
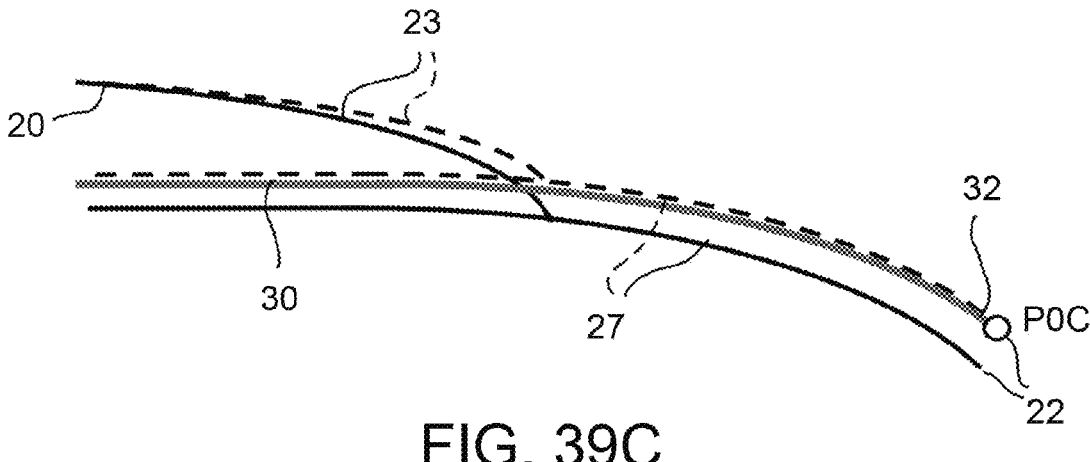
Figure 40:
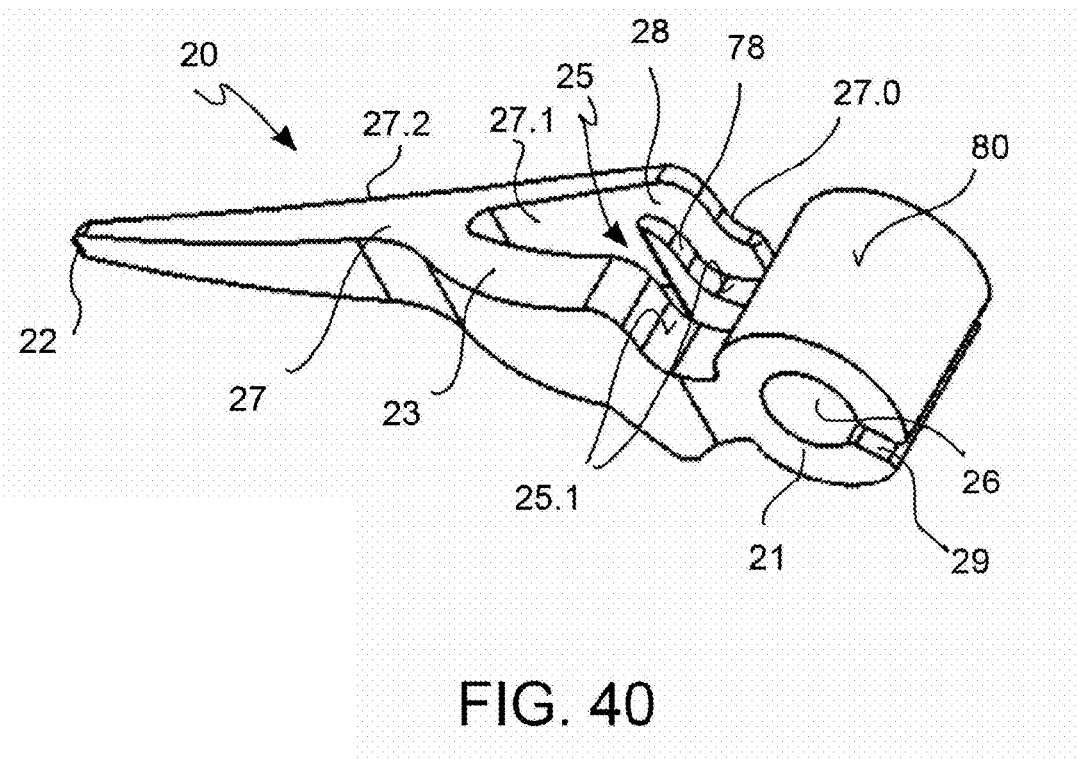
FIG. 40 shows an axonometric view of a reaction link of the end-effector in FIG. 38.

As shown for example in FIG. 39-A, for relatively high opening angles (e.g., angle in the range 50°-60°), the contact between cutting edge 34 with counter-blade portion 24 occurs in a portion of proximal arm 27.1 close to or at the proximal free end 27.0 of the cutting interface portion 27 of the reaction link 20, and the cutting mechanical interference contact thus results in the external axial deformation of the proximal arm 27.1 inside the deformation seat 28 of the reaction link 20, while the blade link 30 remains substantially deformed i.e., does not bend elastically because it is axially supported externally for example by the blade holder link 50. This allows exerting the cutting action even for high opening angles, for example opening angles up to about 60°. As the opening angle decreases, the point of contact POC moves in the distal direction.

As shown for example in FIG. 39-B, for smaller opening angles than those above, i.e., for example opening angles in the range 10°-25°, the point of contact POC between the cutting edge 34 with the counter-blade portion 24 is in a portion of the cutting interface portion 27 of the reaction link 20 close to or at the portion in which the connecting stem 23 terminates, and the cutting mechanical interference contact results in the external axial deformation of the connecting stem 23 which carries the cutting interface portion 25 back in the axially external direction, while the blade link 30 can also not bend elastically but preferably axially externally bends regardless, especially in case of extreme miniaturization of the pieces. This allows the cutting action to be exerted, utilizing the external axial deformation of the reaction link 20 for intermediate opening angles, for example in the range of 10°-25°. In this case, a proximal portion of the blade link 30 can still be in interference contact with the counter-blade portion 24 of the proximal arm 27.1 of the cutting interface portion 27 of the reaction link 20.

As diagrammatically shown for example in FIG. 39-C, for small opening angles, for example in the range 0°-5° and/or 0°-10°, the point of contact POC between the cutting edge 34 with the counter-blade portion 24 is close to or at the distal free ends 22, 32 and the cutting mechanical interference contact results in the external axial deformation of both the blade link 30 and the cutting interface 27 and the connecting stem 23 of the reaction link 20.

The curvature of the counter-blade portion 24 as well as the structure and elastic properties of the cutting interface portion 27 and the connecting stem 23 can be chosen to optimize the cutting performance for an unusually wide range of opening angles, for example in the range of 0°-60°.

A further counter-blade link 40 can be provided, comprising the counter-blade portion 2 in which the counter-blade link 40 is integral in rotation with the reaction link 20, and preferably the counter-blade link 40 comprises in a single piece a root 41 of the counter-blade link 40 next to the root 21 of the reaction link 20 and to the root 31 of the blade link 30.

In accordance with an embodiment, the counter-blade link 40 comprises a counter-blade cutting edge which is preferably arranged opposite with respect to the cutting edge 34 of the blade link 30.

Needle-Driver/Sutures-Cutter Type Surgical Instrument

With reference to the previous description of embodiments of the invention, said surgical instrument 1 can be a surgical instrument of the needle-driver/sutures-cutter type (or "needle-holder/cutter" according to a commonly adopted terminology) as shown for example in FIGS. 2, 4, 6, 10 and 16-29 and 42. Embodiments of said surgical cutting instrument 1 will be described below where said surgical instrument 1 is a surgical instrument of the needle-driver/sutures-cutter type.

In accordance with a preferred embodiment, the distal end 32 of the blade link 30 does not form a free end, while the distal end 52 of the blade holder link 50 forms a distal free end.

Figure 21:
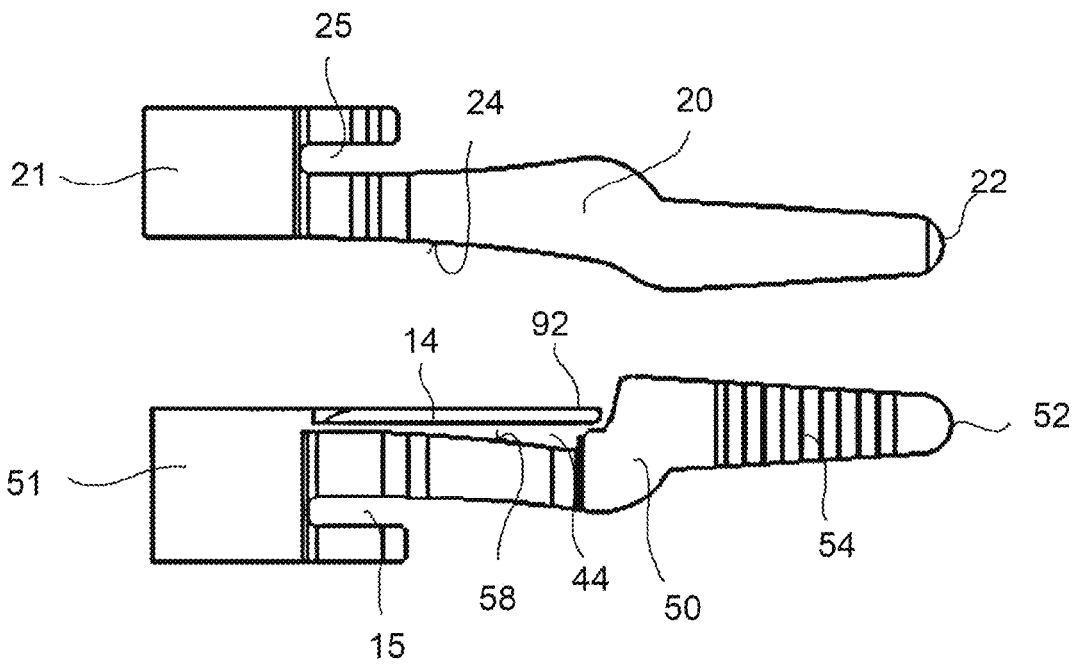
FIG. 21 shows a plan view with separate parts of a portion of an end-effector of a surgical instrument of the needle-driver/suture-cutter type, in accordance with an embodiment.

In accordance with an embodiment, the distal ends 32 and 52 can be made in a single piece in which the distal end 32 of the blade link 30 is a longitudinally retracted free end, i.e., more proximal to the free end 52 of the blade holder link 50, as shown for example in FIG. 21. In this embodiment, the blade link 30 and the blade holder link 50 are made in a single piece, i.e., as a single link.

In accordance with an embodiment, the blade holder link 50 comprises a stroke end surface 54 between the root 51 and the free end 52, in which the stroke end surface 54 also acts as a gripping surface for exerting a gripping action, cooperating with an opposite and faceable gripping surface 53 of the reaction link 20, placed between the root 21 and the free end 22 of the reaction link 20. When in use, the gripping surface 54 of the blade holder link 50 and the gripping surface 53 of the reaction link 20 are intended to be opposite each other and facing each other in rotation, to move in mutual contact to exert a gripping action for example on a surgical needle. Each gripping surface 53, 54 can be machined according to known techniques, forming reliefs and recesses to increase the gripping capacity.

In accordance with an embodiment, the body of the blade link 30 comprises a distal end 32 which preferably acts as a drag engagement portion 37 and thus is not a free end when the blade link 30 is assembled to the blade holder link 50.

In accordance with an embodiment, the body of the blade holder link 50 and the body of the reaction link 20 each have a longitudinally elongated conformation extending from the respective attachment root to the respective free end, in which the respective gripping surface is placed close to the respective free end, and in which the roots of the blade holder link 50, of the blade link 30 and of the reaction link 20 are next to one another, while the blade portion 14 of the blade link 30 is received in an axial seat between the body of the blade holder link 50 and the reaction link 20. In other words, the elongated body of the blade holder link 50 and the reaction link 20 are next to each other at the respective root and at the respective gripping surface, while the blade link 30 is next to the roots of the blade holder link 50 and the reaction link 20 at the root 31 thereof and is next to and interposed between the bodies of the blade holder link 50 and the reaction link 20 along the entire longitudinal extension thereof.

In accordance with an embodiment, the root of the blade link 31 is interposed between the roots of the blade holder link 50 and the reaction link 20. Preferably, the body of the blade link 30 is also longitudinally elongated and comprises a blade link end 32, but is made shorter than the body of the blade holder link 50 and the reaction link 20, and extends substantially in the longitudinal direction from the attachment roots, next to each other, up to the area of the gripping surfaces 53, 54 of the blade holder link 50 and of the reaction link 20, i.e., the distal end 32 of the blade link 30 extends longitudinally to a level which is close to the proximal edge of the gripping surfaces 53, 54.

The gripping surfaces 53, 54 preferably act as closing stroke ends for the degree of freedom of opening/closing G.

In accordance with an embodiment, the blade holder link 50 comprises a surface 58 facing axially inwards which is inclined away from the body of the blade link 30 axially internally delimiting an axial deformation recess 44 (or deformation seat 44) adapted to accommodate the blade portion 14 of the body of the blade link 30 when elastically bent by the action of the protruding surface of the counter-blade 24 during the cutting action. Therefore, the counter-blade portion 24 and the surface 58 facing axially inwards both result facing the blade portion 14 of the blade link 30 and both contacting thereto during the cutting action. Preferably, the internally axially facing surface 58 of the blade holder link 50 serves as the axial stroke end abutment surface for the deformation of the blade portion 14 of the blade link 30 when deformed by bending by the counter-blade portion 24, during the cutting action. The profiles of the protruding surface of the counter-blade 24 and the axially facing surface 58 of the blade holder link 50 can be parallel to each other, and in an embodiment are correspondingly identical.

The at least one point of contact POC between the cutting edge 34 and the counter-blade portion 24 preferably varies in position and/or size as a function of the opening angle of the degree of freedom of opening/closing G, as diagrammatically shown for example in FIG. 19. In particular, at relatively high opening angles (e.g., angle in the range of 20°-30°) the contact occurs in a portion which is more proximal to the cutting edge 34, i.e., closer to the attachment root 31 of the blade link 30, and as the opening angle reduces the contact moves in the distal direction, accentuating the elastic deformation bending of the blade portion 14 of the blade link 30 with respect to the root 31 of the blade link 30. Therefore, the deformed configuration of the blade link 30 and the blade holder link 50 and the reaction link 20 are in a substantially closed configuration is maximally bent, and in any case more bent than the deformed configuration of the blade link 30 when the blade holder link 50 and the reaction link 20 are in a partially closed and partially open configuration. Preferably, when the opening angle is maximally open and the blade is free, the blade is straight the blade link has a substantially planar configuration.

In accordance with an embodiment, the counter-blade portion 24 can be at least in part overlapping on the rotational approaching footprint of the body of the blade holder link 50 and the blade portion 14 of the blade link 30 when in an elastically deformed configuration it locally translates with respect to the rotational footprint of the blade holder link 50 in a direction transverse to the longitudinal extension direction of the blade holder link 50, i.e., in an external axial direction, although in accordance with a preferred embodiment, the counter-blade portion 24 and the surface 58 facing axially inwards of the blade holder link 50 are geometrically shaped so as not to overlap in their respective rotational clearances.

Figure 22:
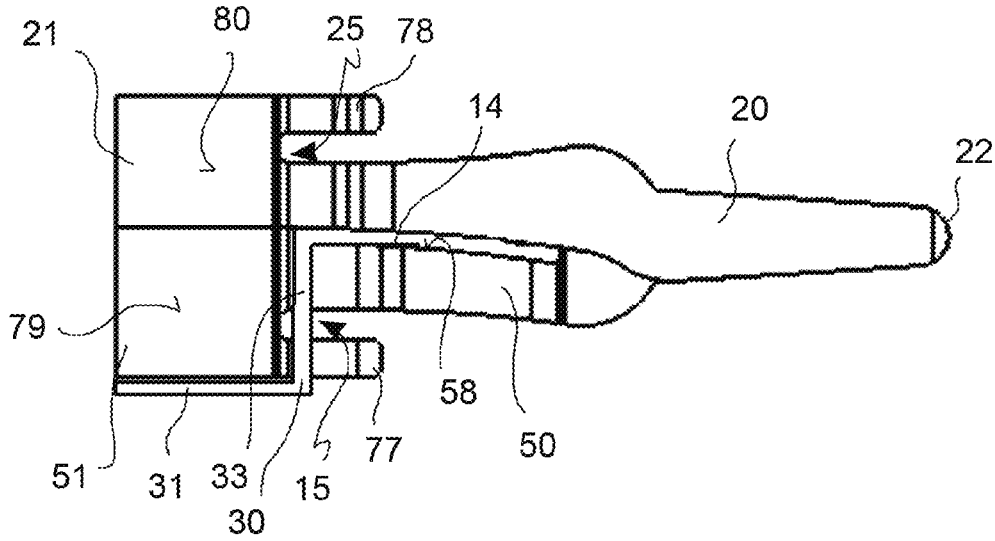
FIG. 22 shows a plan view of a portion of an end-effector of a surgical instrument of the needle-driver/suture-cutter type, in accordance with an embodiment.
Figure 23:
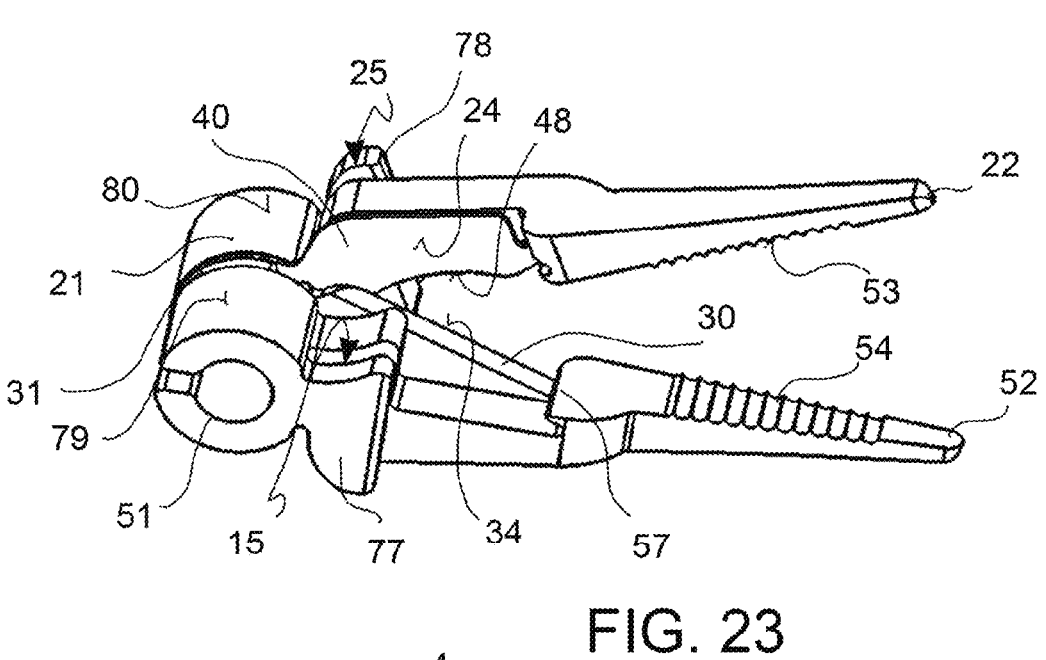
FIG. 23 shows an axonometric view of a portion of an end-effector of a surgical instrument of the needle-driver/suture-cutter type, in accordance with an embodiment.
Figure 24:
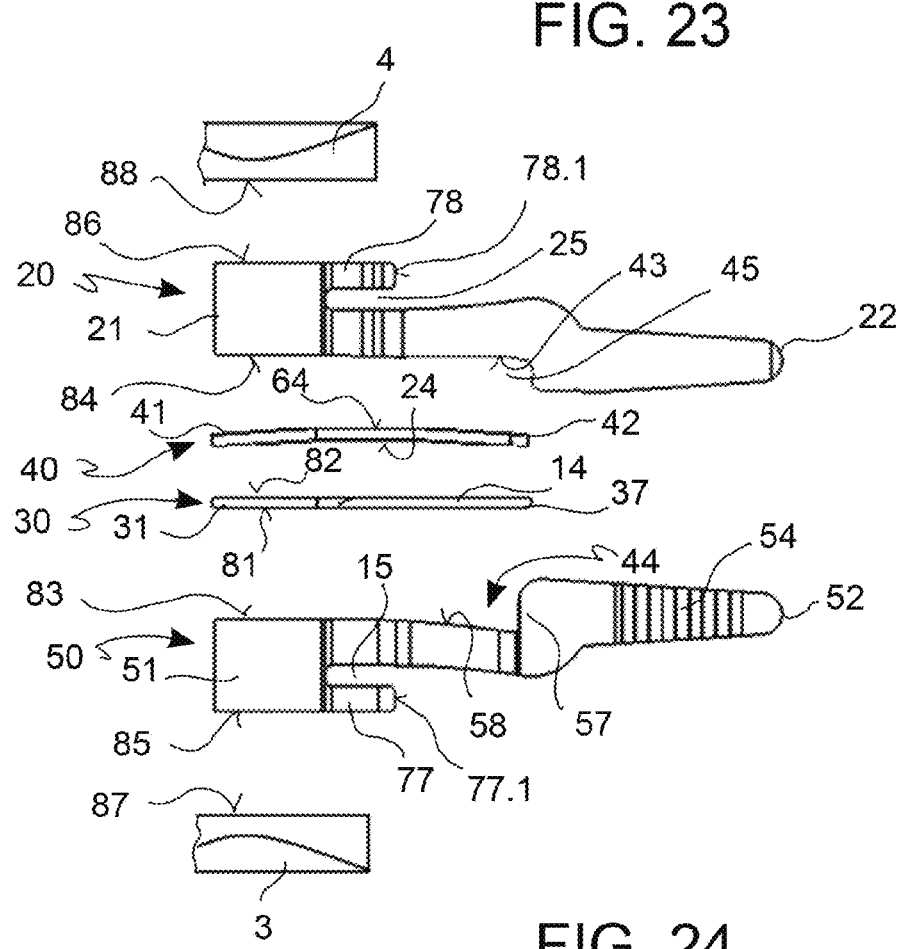
FIG. 24 shows a plan view with separate parts of a portion of an end-effector of a surgical instrument of the needle-driver/suture-cutter type, in accordance with an embodiment.
Figure 25:
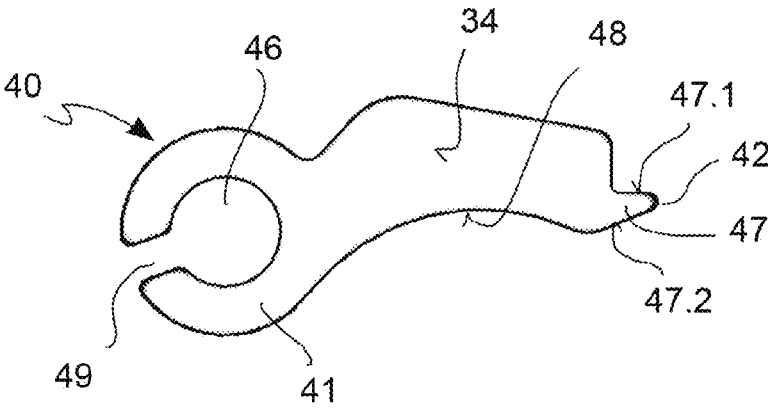
FIG. 25 shows a vertical elevation view of a counter-blade link, according to an embodiment.
Figure 26:
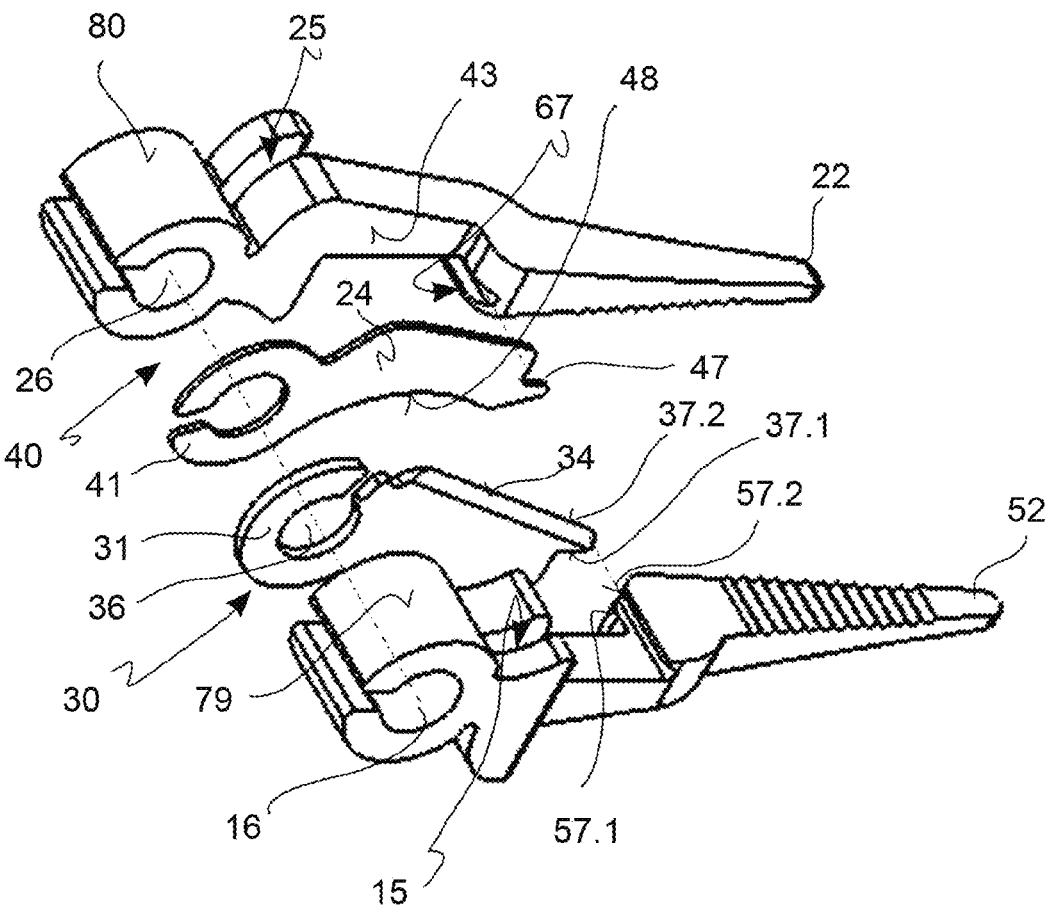
FIG. 26 shows an axonometric view with separate parts of a portion of the end-effector in FIG. 23.
Figure 27:
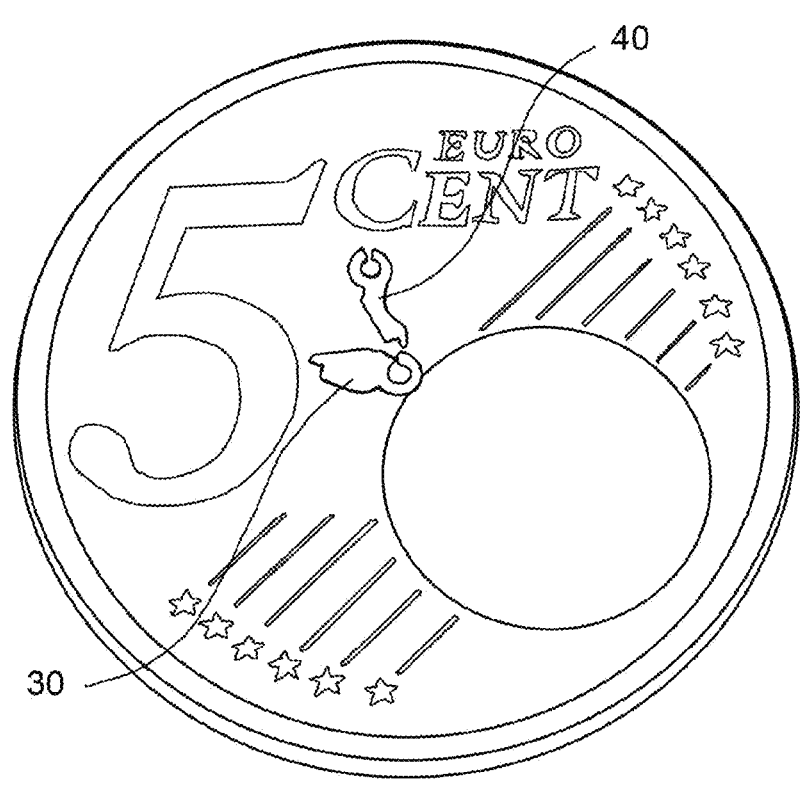
FIG. 27 is an electron microscope photographic image depicting a blade link and a counter-blade link placed on a face of a five euro cent coin.
Figure 28:
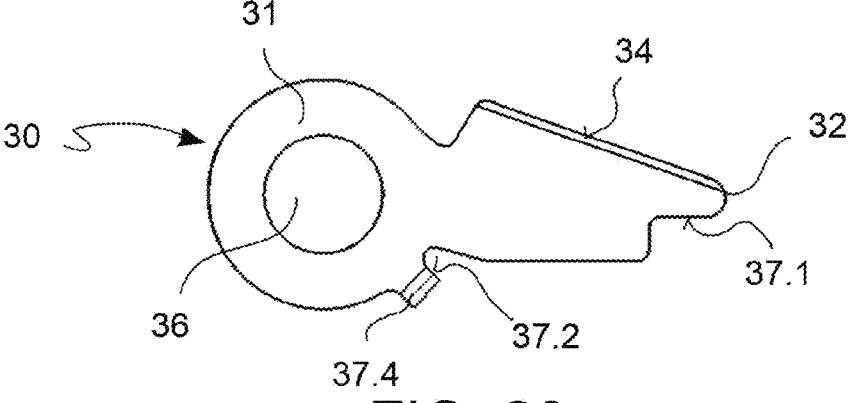
FIG. 28 shows a vertical elevation view of a blade link, according to an embodiment.

In accordance with an embodiment as shown for example in FIG. 22, the root 31 of the blade link 30 is interposed between and at direct and intimate contact with the first prong 3 of the support structure and the root 51 of the blade holder link 50. The provision of a transverse bridge 33 in the body of the blade link 30 which crosses the rotational approaching footprint of the body of the counter-blade holder link 50 brings the blade portion 14 with the cutting edge 34 thereof into contact with the counter-blade portion 24, i.e., between the blade holder link 50 and the reaction link 20.

In accordance with an embodiment, a counter-blade link 40 is provided, comprising in a single piece said counter-blade portion 24, in which the counter-blade link 40 is integral in rotation with the reaction link 20. Preferably, the counter-blade link 40 comprises in a single piece a proximal attachment root 41 and said counter-blade portion 24, and the reaction link 20 comprises in a single piece the root 21, the gripping surface 53 and the distal free end 22, in which the root 41 of the counter-blade link 40 and the root 21 of the reaction link 20 are next to and in direct and intimate contact with each other. Where said counter-blade link 40 is provided, then the group formed by said root 51 of the blade holder link 50, and said root 31 of the blade link 30, and said root 41 of the counter-blade link 40 and said root 21 of the reaction link 20 is globally interposed between said two prongs 3, 4 of the distal connecting portion 17 of the support link 2 and in direct and intimate contact therewith. In other words, where said counter-blade link 40 is provided, the axially rigid distal rotational joint 502 is also formed by the root 41 of the counter-blade link 40.

By virtue of such a pack arrangement of the roots, impingements of the root 31 of the blade link 30 and of the root 41 of the counter-blade link 40, which are preferably thinner, with respect to the articulation pin 5 are avoided so as to provide a satisfactory certainty of positioning of the cutting edge 34 with respect to the counter-blade portion 24 for each opening angle of the degree of freedom of opening/closing G, thus providing extreme cutting precision.

In accordance with an embodiment in which a counter-blade portion 24 is provided, which is made on a separate counter-blade link 40 having a proximal attachment root 41, then the root 31 of the blade link 30 is axially interposed between said root 41 of the counter-blade link 40 and the root 51 of the blade holder link 50, and in direct and intimate contact therewith, and in which said root 41 of the counter-blade link 40 is axially interposed between said root 31 of the blade link 30 and said root 21 of the reaction link 20, and in direct and intimate contact therewith, to provide a reaction to the elastic bending of the blade portion 14 during the cutting action.

As mentioned above, the roots preferably have a cylindrical geometry about the common rotation axis Y-Y, and where the root 41 of the counter-blade link 40 has significantly smaller thickness than the root 51 of the blade holder link 50 and the root 21 of the reaction link 20, said root 41 of the counter-blade link 40 has a cylindrical geometry of the discoid type, similar to the root 31 of the blade link 30.

Where said root 41 of the counter-blade link 40 is provided, it will be provided with a through hole 46 which can be coaxial with the through holes 16, 26, 26 and of equal diameter. In accordance with an embodiment, said through hole 46 of the root 41 of the counter-blade link 40 has a hole edge in direct and intimate contact with the articulation pin 5 for the entire extension of the hole edge, to exert with an arc surface thereof the thickness of the hole edge a reaction to the friction exchanged between the blade link 30 and the counter-blade portion 24 of the counter-blade link 40 during the cutting action.

In accordance with an embodiment in which the blade link 30 and the blade holder link 50 further comprise respective drag engagement portions 37, 57 for making the blade link 30 and the blade holder link 50 integral in rotation, the drag engagement portion 57 of the blade holder link 50 is made as a drag seat 57 delimited by a drag tooth facing the rotation axis Y-Y which forms an undercut seat with respect to the gripping surface 54, i.e., a seat 57 which opens proximally and also extends axially, to receive the distal end 32 of the blade link 30 in rotation drag contact while receiving the deformation of the distal end 32 of the blade link 30 in the axial direction. In other words, a portion close to or at the distal end 32 of the blade link 30 serves in this embodiment as a drag engagement portion 37 of the blade link 30 which is received in rotation drag contact, i.e., in the opening/closing direction, inside the drag seat 57 of the blade holder link 50, and at the same time the distal end 32 of the blade link 30 is free to deform axially externally inside the same drag seat 57 which therefore forms part of the axial deformation seat 44 for the blade portion 14. In other words, the drag seat 57 extends distally with respect to the surface 58 facing axially inwards of the blade holder link 50, i.e., with respect to the surface 58 which can act as an axial abutment for the bending of the blade portion 14. In such a case, the drag seat 57 has an axial extension such as to accommodate the distal end 32 of the blade link 30, thus receiving together with said deformation seat 44 the deformation of the blade link 30 during the cutting action. The distal end 32 of the blade link 30 can comprise a distal portion of said cutting edge 34, and in such a case said distal portion of said cutting edge 34 acts as a drag counter-surface in the opening direction 37.2 cooperating against a respective opening drag surface 57.2 of the drag tooth delimiting the drag seat 57 of the blade holder link 50.

In accordance with an embodiment in which the blade link 30 and the blade holder link 50 further comprise respective drag engagement portions 37, 57 to make the blade link 30 and the blade holder link 50 integral in rotation, the drag engagement portion 57 of the blade holder link 50 is made as two distinct and separate drag surfaces. In other words, the opening drag surface 57.2 and the closing drag surface 57.1 of the blade holder link 50 can be placed at different distances from the common rotation axis Y-Y, as well as the opening drag surface 37.2 and the closing drag surface 37.1 of the blade link 30 can be arranged at different distances from the common rotation axis Y-Y, for example on different protrusions of the blade link 30, as shown for example in FIG. 28. In particular, with reference to such FIG. 28, the root 31 of the blade link 30 can comprise a radial drag ear 37.4 folded on the root 51 of the blade holder link 50, said drag ear 37.4 comprising said opening drag surface 37.2.

In accordance with an embodiment, said blade holder link 50 and said blade link 30, being made in separate pieces, are integral in rotation with each other in a releasable manner and the release can preferably occur only by disassembling the articulated end-effector 9.

In accordance with an embodiment, the reaction link 20 comprises a thread-stop wall 48 facing the common rotation axis Y-Y delimiting a thread-stop recess for receiving a suture thread 68 to keep the suture thread 68 in contact with the cutting edge 34 of the blade of the blade link 30 during a cutting closure. The provision of the thread-stop wall 48 prevents the suture thread 68 from sliding distally during the cutting action beyond the distal end 32 of the blade, as an effect of the closing action.

For example, the thread-stop wall 48 is an arched wall which has a concavity defining the recess facing the cutting edge 34. The recess can be made in the form of a notch provided in the body of the reaction link 20 and in such a case the thread-stop wall 48 is a wall delimiting said notch. The recess can be made in the form of an undercut wall provided on a protrusion of the body of the reaction link 20 and in such a case the thread-stop wall 48 is an undercut wall of said protrusion facing the common rotation axis Y-Y.

In accordance with an embodiment, the thread-stop wall 48 delimits with an axially internal edge thereof the counter-blade portion 24. Where the counter-blade portion 24 is made in a separate piece with respect to the reaction link 20, the thread-stop wall 48 and the recess can be formed in the body of the counter-blade link 40.

In accordance with an embodiment, the reaction link 20 comprises an axial recess 45 forming a housing seat 45 for the counter-blade link 40. Said axial recess 45 is preferably axially delimited by a surface 43 facing axially inwards of the reaction link 20.

In accordance with a preferred embodiment, the counter-blade link 40 is elastically deformable by bending. Thereby, when the cutting edge 34 of the blade link 30 is in mechanical interference contact with the counter-blade portion 24 of the counter-blade link 40 to exert a cutting action, the body of the counter-blade link 40 elastically bends in the axial direction as well.

The counter-blade link 40 is preferably made from an elastic sheet or strip and is pre-curved to form a curved, protruding counter-blade portion 24 having a concavity facing axially inwards, in order to elastically bend the blade link 30 during the cutting action. The provision of a counter-blade link 40 having a curved, protruding counter-blade portion 24 elastically deformable by bending allows obtaining an elastic reaction between the surface 43 facing axially inwards of the axial recess 45 of the reaction link 20 and the cutting edge 34 of the blade link 30, during the cutting action. In particular, the counter-blade link 40 comprises a resting surface 64 directed axially and opposite the counter-blade portion 24 which abuts against said surface 43 facing axially inwards of the axial recess 45 of the reaction 20 to allow the counter-blade link 40 to provide an elastic action on the cutting edge 34 of the blade link 30 aimed at resiliently bending the blade link 30 during the cutting action. For example, the counter-blade link 40, where present, can be made of spring steel.

The counter-blade link 40 can have at least some, but also all, of the features and properties described above with reference to the blade link 30. The thickness of the counter-blade link 40 can be substantially comparable to or equal to the thickness of the blade link 30, as described above. In accordance with an embodiment, the counter-blade link 40 comprises a counter-blade cutting edge which is preferably arranged opposite with respect to the cutting edge 34 of the blade link 30. The proximal attachment root 41 of the counter-blade link 40 can have at least some, but also all, of the features and properties described above with reference to the root 31 of the blade link 30. The root 41 of the counter-blade link 40 can comprise a radial cutting channel 49 misaligned with the radial cutting channel 39 of the blade link 30 to prevent the edges of the cutting channels 39, 49 from engaging during the opening/closing action.

In accordance with an embodiment, to make the counter-blade link 40 and the reaction link 20 integral in rotation, a drag engagement is provided along the longitudinal extension of the counter-blade surface 24 or distally with respect thereto. Preferably, the drag engagement is obtained close to or at the distal end 42 of the counter-blade link 24. In accordance with an embodiment, the reaction link 20 substantially acts as a counter-blade holder link and comprises a drag seat 67 having an opening drag surface and an opposite closing drag surface to make the counter-blade link 40 integral in rotation. The drag seat 67 can be placed distally in a drag seat made undercut with respect to the gripping surface 53 of the reaction link 20 to receive the distal end 42 of the counter-blade link 40. In accordance with an embodiment, said distal end 42 of the counter-blade link 40 comprises an opening drag surface 47.2 in dragging contact with said opening drag surface of the reaction link 20, and an opposite closing drag surface 47.1 in dragging contact with said closing drag surface. In other words, in this embodiment, the drag engagement portion 47 of the counter-blade link 40 is positioned close to or at the distal end 42 of the counter-blade link 40. The distal end 42 of the counter-blade link 40 is preferably a distal end constrained to the reaction link 20.

Figure 29:
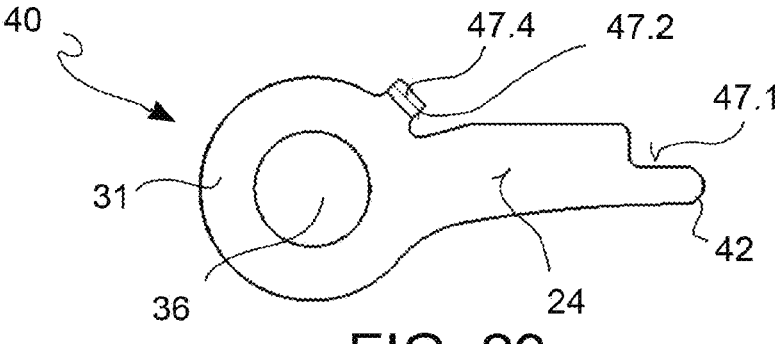
FIG. 29 shows a vertical elevation view of a counter-blade link, according to an embodiment.
Figures 30, 31:
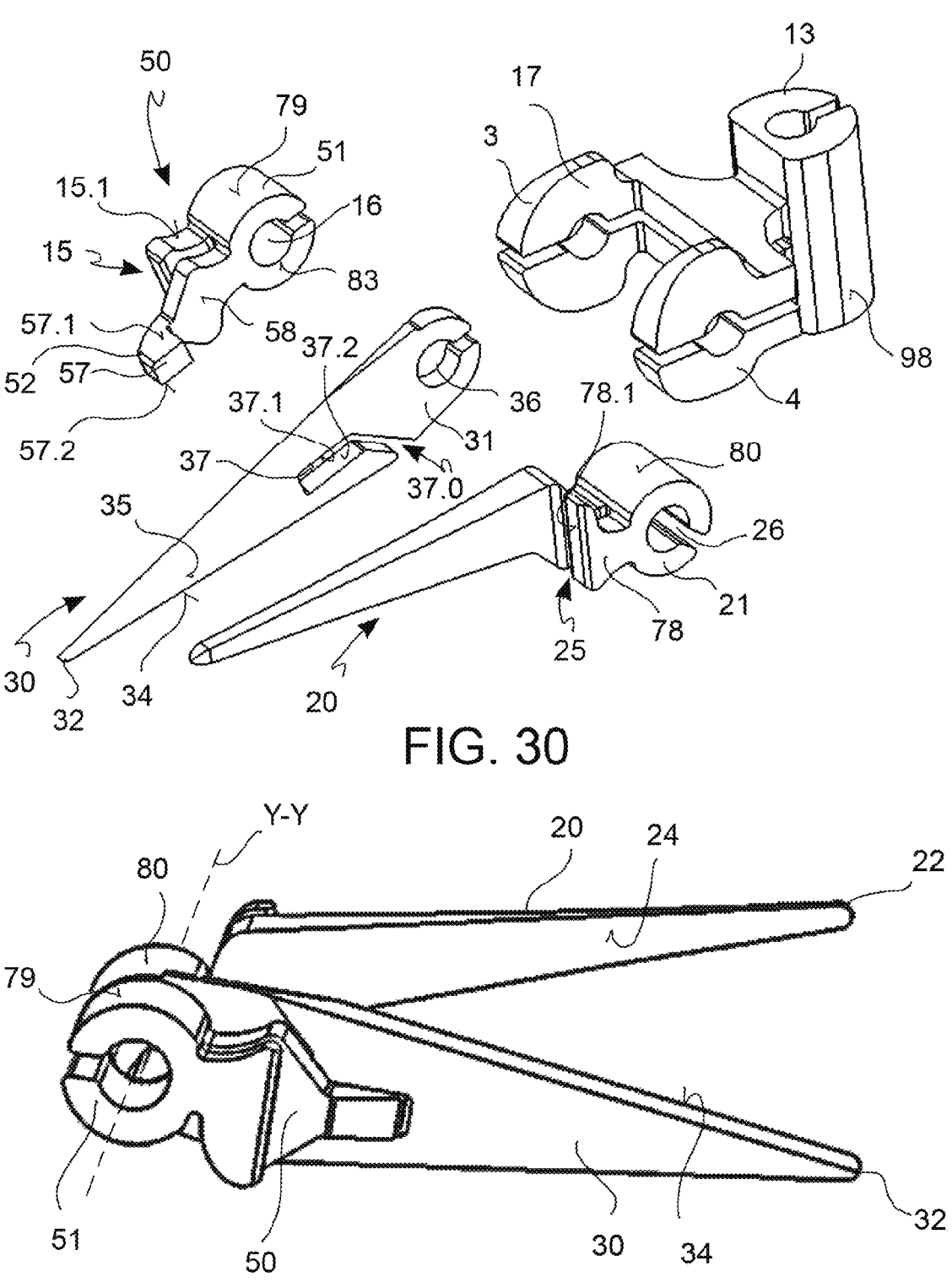
FIG. 30 shows an axonometric view with separate parts of a portion of an end-effector of a surgical instrument of the surgical scissors type, according to an embodiment.
FIG. 31 shows an axonometric view of a portion of an end-effector of a surgical instrument of the surgical scissors type, according to an embodiment, in which the degree of freedom of opening/closing is partially open.
Figure 32:
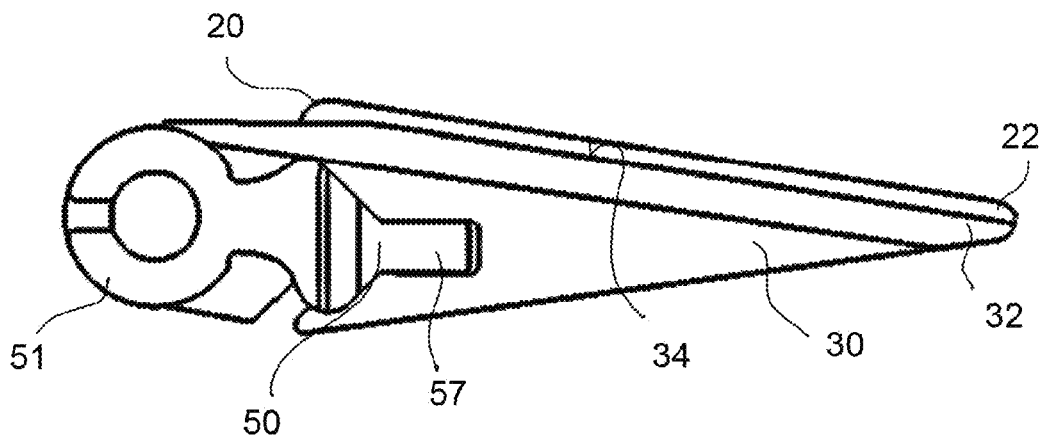
FIG. 32 shows a vertical elevation view of a portion of an end-effector of a surgical instrument of the surgical scissors type, according to an embodiment, in which the degree of freedom of opening/closing is closed.
Figure 33:
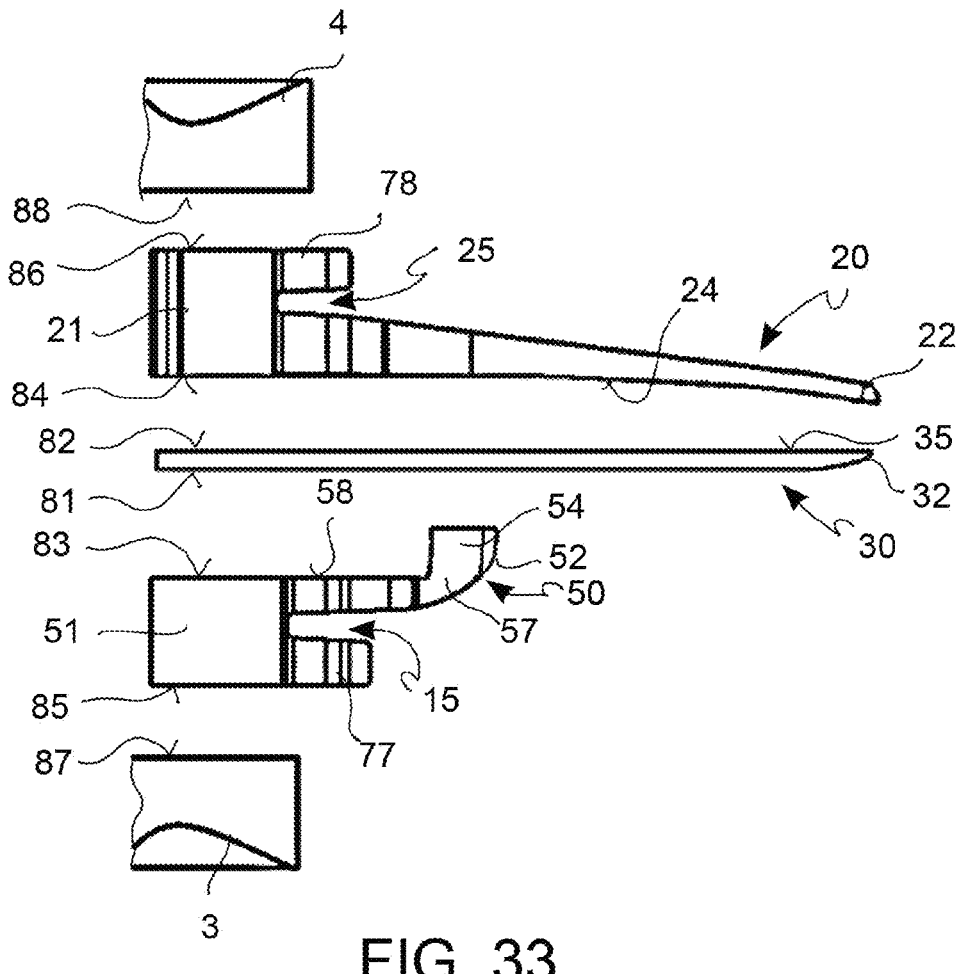
FIG. 33 shows a plan view with separate parts of a portion of an end-effector of a surgical instrument of the surgical scissors type, according to an embodiment.

In accordance with an embodiment as shown for example in FIG. 29, the counter-blade link 40 comprises a radial drag ear 47.4 folded on the root 21 of the reaction link 20, said drag ear 47.4 of the counter-blade link 40 comprising an opening drag surface 47.2 in drag contact with an opening drag surface 67.2 which is for example placed on a back portion of the body of the reaction link 20, and in which the counter-blade link 40 further comprises a closing drag surface 47.1 placed close to the distal end 42 of the counter-blade link 40 in drag contact with a closing drag surface 67.1 of the counter-blade holder link 60.

In accordance with an embodiment, the counter-blade cutting edge can have a concave shape with respect to the opening/closing direction.

In accordance with a general embodiment, a robotic surgery system 101 is provided, comprising at least one surgical instrument 1 according to any one of the embodiments described above. The robotic surgery system 101 is thus capable of performing surgical or microsurgical procedures including cutting a biological tissue and/or cutting sutures.

In accordance with an embodiment, said robotic surgery system 101 comprises at least two surgical instruments, at least one of which is a surgical instrument 1 according to any one of the embodiments described above and the other surgical instrument can be a surgical instrument of the needle-driver type or a surgical instrument of the dilator type, although in accordance with an embodiment both surgical instruments are surgical instruments 1 according to any one of the embodiments described above, not necessarily mutually identical although they can be. For example, a surgical instrument of the at least two surgical instruments can be a surgical instrument of the surgical scissor type and another surgical instrument of the at least two surgical instruments can be a surgical instrument of the needle-driver/scissor type.

The robotic surgery system 101 preferably comprises at least one robotic manipulator 103 and the at least one surgical instrument 1 is operatively connected to said at least one robotic manipulator 103. For example, a sterile surgical barrier (not shown), such as a sterile surgical cloth, for example, is interposed between the at least one robotic manipulator 103 and the backend portion 104 of the at least one surgical instrument 1. The robotic manipulator 103 can comprise motorized actuators for stressing said actuation tendons of the degrees of freedom of pitch P, yaw Y and grip G, i.e., cutting G of the surgical instrument 1, and a motorized actuator for rotating the surgical instrument 1 about the shaft 7 defining a degree of freedom of roll R. The robotic surgery system 101 can comprise a support portion 106 (cart or tower) for example comprising wheels or other ground contact units, and an articulated positioning arm 105, for example manually movable i.e., passive, extending between the support portion 106 and the at least one robotic manipulator 103. In accordance with an embodiment, the robotic surgery system 101 comprises at least one master console 107 for controlling the at least one surgical instrument 1 and preferably also the respective robotic manipulator 103 according to a master-slave architecture, and preferably the robotic surgery system 101 further comprises a control unit operatively connected to the master console 107 and the robotic manipulator 103 for determining the tracking of the surgical instrument 1 to at least one master control device 108 of the master console 107. In accordance with an embodiment, the master console 107 comprises at least one master control device 108 which is unconstrained, i.e., mechanically disconnected from the ground, and a tracking system, for example optical and/or magnetic.

A cutting method for a surgical instrument will be described below.

A cutting method for a surgical instrument comprising the steps below.

Longitudinally sliding the tendons 71, 72, 75, 76 of at least one pair of antagonistic tendons on convex ruled surfaces with parallel generator lines of at least one of a connection link 90 and a support link 2 to orient a cutting edge 34 in a desired orientation;

Longitudinally sliding the tendons 71, 72, 73, 74 of at least one pair of antagonistic actuation tendons of the distal rotational joint 502 on the convex ruled surfaces of the connection link 90 and the support link 2 to bring the cutting edge 34 into contact with a counter-blade portion 24. This step can be performed by relatively approaching the blade link 30 and the reaction link 20, i.e., moving with the sliding of said tendons 71, 72, 73, 74 on the convex ruled surfaces of the connection link 90 and of the support link 2 by a degree of freedom of opening/closing G.

In accordance with a preferred operating mode, the step of longitudinally sliding the tendons 71, 72, 73, 74 of at least one pair of antagonistic actuation tendons of the distal rotational joint 502 on the convex ruled surfaces of the connection link 90 and the support link 2, comprises the step of winding at least one movement tendon 71, 72, 73, 74 of the distal rotational joint 502 on the ruled surfaces of the links 2 and 90 on which it slides by a winding angle between 60° and 300°, and preferably greater than 120°. In other words, each movement tendon 71, 72, 73, 74 of the distal rotational joint 502 describes on each of the convex ruled surfaces 96, 97, 98, 99 of the connection link 90 and of the support link 2 on which an arcuate longitudinal sliding path slides which subtends a local winding angle, and the sum of all the local winding angles for at least one movement tendon of the distal rotational joint 502 provides a value between 60° and 300°, and preferably greater than 120°. It should be noted that the convex ruled surfaces 79, 80 of the pulley portions of the blade holder links 50 and reaction links 20, not performing any sliding of the tendons, do not participate in the count.

In accordance with a preferred operating mode, the steps of sliding the tendons longitudinally are performed by sliding each tendon along a stationary longitudinal path, preventing the tendons from translating in a direction parallel to the distal rotation axis Y-Y as well as preventing the tendons from translating in a direction parallel to the proximal rotation axis P-P.

The method further comprises the step of elastically bending at least one of the cutting edge 34 and the counter-blade portion 24, making a mechanical interference contact therebetween which exerts a cutting action.

In accordance with a preferred operating mode, the method is performed with a surgical instrument 1 according to any one of the previously described embodiments.

It is well understood that the combination of features, structures or functions disclosed in one or more of the appended claims forms an integral part of the present description.

By virtue of the features described above, provided either separately or in combination with one another in particular embodiments, it is possible to meet the needs mentioned above, and to obtain the aforementioned advantages, and in particular:

the degree of freedom of opening/closing allows performing a cutting action;

an axially rigid rotational joint is provided in which the cutting action is carried out by elements forming the rotational joint;

the termination seats of the tendons and the ruled pulley surfaces made in a single piece with the respective links favor miniaturization, helping keep the number of pieces small and the articulated end-effector compact;

the degree of freedom of opening/closing actuation tendons slide longitudinally on the ruled surfaces of the connection link and of the support link during the movement of the degree of freedom of opening/closing, avoiding sliding axially on such ruled surfaces even if the ruled surfaces have no guide channels or grooves for guiding the tendons; i.e., in other words, the sliding path of the tendons remains stationary for any operating configuration;

preferably, the paths of the tendons are all parallel to one another;

a same convex ruled surface of the support link can be a sliding surface for an actuation tendon of the degree of freedom of opening/closing and a winding surface i.e., a pulley portion for an actuation tendon of the degree of freedom of pitch;

the pulley portions of the blade holder link and the reaction link are formed by convex ruled surfaces which do not comprise guide channels or grooves on which they wind without sliding either longitudinally or axially end sections (close to the respective termination) of the respective actuation tendons;

an extreme miniaturization of the articulated end-effector of the surgical instrument as compared to known solutions is allowed;

it is possible to stack the roots of the links between the prongs of the distal connecting portion of the support link and meanwhile avoiding the provision of elastic washers as well as adjustment screws, as well as tapping or threading machining at the level of the attachment roots, thus allowing an extreme miniaturization of the articulated end-effector;

in particular, the articulation pin 5 is unthreaded;

neither are the hole edges surfaces of the through holes of the roots of the respective links tapped, i.e., internally threaded, nor are the internal surfaces of the prong through holes of the prongs of the distal connecting portion of the support link;

no elastic elements are provided, such as the Belleville washer type fitted on the articulation pin;

it allows substantially providing all the elasticity necessary for the cutting action concentrated outside the roots, i.e., in the blade portion of the blade link and, if necessary, also in the counter-blade surface of the reaction link, allowing performing a precise cutting action while creating extremely miniaturized articulated end-effectors;

in particular, for relatively high opening angles of the degree of freedom of opening/closing the blade is free, i.e., elastically non-deformed, and is preferably straight in such a configuration;

as the opening angle of the degree of freedom of opening/closing closes, the blade is elastically bent, elastically pushing against the counter-blade;

since the elasticity necessary for the cutting action is
concentrated distally with respect to the roots, a defor-
mation seat can be provided, which receives the rela-
tively high axial bending of the blade or counter-blade;
the roots stacked in packs between the prongs provide a
reaction to the elastic bending deformation of the blade
portion, avoiding axial sliding on the articulation pin,
thus allowing a precise and effective cutting action of
the cutting edge;
the blade link and the counter-blade link, where present,
are dragged in rotation by the blade holder link and
reaction link;
the provision of through holes of all the coaxial and
receiving roots with contact with the articulation pin
allows avoiding undesired relative rotations between
the roots, providing positioning certainty of the cutting
edge with respect to the counter-blade, thus allowing an
extreme miniaturization of the articulated end-effector,
since small rotational movements at the level of the
root, i.e., close to the common rotation axis would
impose relatively large cutting inaccuracies;
in addition, the hole of the blade link exerts with the
proximal edge thereof pushing on the pin a reaction to
the frictional force between the blade and the counter-
blade during the cutting action, helping obtain a precise
cutting action;
the cutting edge of the blade link can be made straight i.e.,
without concavity, facilitating production in series, for
example starting from a single band or strip;
the provision of a single drag engagement portion in
rotation between blade link and blade holder link
allows minimizing the drag clearance, favoring minia-
turization;
the rotational joint 502 defining the common rotation axis
Y-Y can be a hinge.

In order to meet specific, contingent needs, those skilled
in the art can make several changes and adaptations to the
above-described embodiments and can replace elements
with other functionally equivalent ones, without departing
from the scope of the appended claims.

LIST OF REFERENCE SIGNS

1 Surgical cutting instrument
2 Support link
3 First support link prong
4 Second support link prong
5 Articulation pin or pivot pin
6 Termination seat for the third pair of support link
actuation tendons, or third support link termination seat
6.1 Drag abutment walls of the third termination seat
7 Surgical instrument rod or shaft
8 Rod distal end
9 Articulated end-effector, or articulated terminal
13 Proximal connecting portion of the support link
14 Bridge portion
15 First termination seat
15.1 Drag abutment walls of the first termination seat
16 First through hole
17 Distal connecting portion of the support link
19 Radial cutting channel
20 Reaction link
21 Proximal attachment root of the reaction link
22 Distal free end of the reaction link
23 Connecting stem of the reaction link
24 Counter-blade portion
25 Second termination seat

25.1 Second termination seat drag abutment walls
26 Through hole of the reaction link root
27 Cutting interface portion of the reaction link
27.0 Proximal free end of the cutting interface portion
27.1 First proximal arm of the cutting interface portion
27.2 Second distal arm of the cutting interface portion
28 Axial deformation seat of the reaction link, or axial
deformation seat of the counter-blade
29 Radial cutting channel
30 Blade link
31 Proximal attachment root of the blade link, or blade
link root
32 Distal blade link end
33 Transverse blade link bridge
34 Blade link cutting edge
35 Blade portion surface facing axially inwards
36 Through hole of the blade link root
37 Blade link drag engagement portion
37.0 Blade link drag seat inlet opening
37.1 Blade link closing drag surface
37.2 Blade link opening drag surface
37.4 Cantilevered blade link ear
38 Arc surface of the hole edge of the blade link root
39 Blade link root cutting channel
40 Counter-blade link
41 Proximal attachment root of the counter-blade link, or
counter-blade link root
42 Distal counter-blade link end
43 Surface facing axially inwards of the counter-blade
holder link recess
44 Axial deformation seat for the blade of the blade holder
link
45 Axial counter-blade link recess
46 Through hole of the counter-blade link root
47 Drag engagement portion of the counter-blade link
47.1 Counter-blade link closing drag surface
47.2 Counter-blade link opening drag surface
47.4 Counter-blade link drag ear
48 Thread-stop wall
49 Radial cutting channel of the counter-blade link
50 Blade holder link
51 Proximal attachment root of the blade holder link, or
blade holder link root
52 Distal blade holder link end
54 Closing stroke end surface of the blade holder link
57 Blade holder link drag engagement portion
57.1 Blade holder link closing drag surface
57.2 Blade holder link opening drag surface
58 Surface facing axially inwards of the blade holder link
64 Counter-blade link support surface
67 Drag engagement portion of the reaction link
68 Suture thread
70 Tendon termination
71 First tip opening actuation tendon
72 First tip closing actuation tendon
73 Second tip opening actuation tendon
74 Second tip closing actuation tendon
75 Support link actuation tendon
76 Support link actuation counter-tendon
77 First cantilevered drag leg of the first termination seat
of the first tip
77.1 Free end of the first leg
78 Second cantilevered drag leg of the second termination
seat of the second tip
78.1 Free end of the second leg
79 Ruled surface of the blade holder link pulley portion
80 Ruled surface of the reaction link pulley portion 81 Contact surface of the blade link root
82 Opposite contact surface of the blade link root
83 Internal contact surface of the blade holder link root
84 Internal contact surface of the reaction link root
85 External contact surface of the blade holder link root
86 External contact surface of the reaction link root
87 Internal contact counter-surface of the first prong
88 Internal contact counter-surface of the second prong
90 Connection link
91 First prong of the connection link
92 Second prong of the connection link
93 Proximal articulation pin
94 Fixing device
95 Distal connecting portion of the connection link
96 Convex ruled surface of the support link
97 Convex ruled surface of the connection link
98 Convex ruled surface of the support link
99 Convex ruled surface of the connection link
101 Robotic surgery system
102 Rod proximal end
103 Robotic manipulator
104 Proximal interface portion of the surgical instrument, or surgical instrument backend portion
105 Positioning arm
106 Support portion, or cart, or tower
107 Master console
108 Master control device
502 Distal rotational joint
509 Proximal rotational joint
X-X Rod longitudinal axis
Y-Y Common rotation axis, or common distal rotation axis or common yaw rotation axis
P-P Common proximal rotation axis, or common pitch rotation axis
Y Degree of freedom of yaw
P Degree of freedom of pitch
G Opening/closing direction, or degree of freedom of cutting
R Degree of freedom of roll
POC At least one point of contact between blade and counter-blade
Y5 First axial distance
Y5' Second axial distance
Y8 Further axial distance

The invention claimed is:

1. A surgical cutting instrument comprising a rod having a distal end and an articulated end-effector connected to the distal end of the rod, wherein said articulated end-effector comprises:

a connection link connected to the distal end of the rod having a body comprising in a single piece:
one or more convex ruled surfaces of connection links with parallel generator lines,
a first distal connecting portion;
a support link articulated to the connection link and having a body comprising in a single piece:
one or more convex ruled surfaces of support links with parallel generator lines;
a proximal connecting portion articulated to the first distal connecting portion of the first connection link, defining a proximal rotational joint for the connection link and the support link so that the connection link and the support link are rotatable relatively about a common proximal rotation axis;
a second distal connecting portion;
a blade holder link articulated to the support link having a body comprising in a single piece:

a blade holder link attachment root having a pulley portion formed by one or more convex ruled surfaces of blade holder root with parallel generator lines,
a drag portion
a blade link, integral in rotation with said blade holder link, having a body comprising in a single piece a cutting edge and a drag counter-portion engaged with said drag portion of the blade holder link;
a reaction link articulated to the support link and to the group formed by the blade link and the blade holder link, having a body comprising in a single piece an attachment root having a pulley portion formed by one or more convex ruled surfaces of reaction link root, with parallel generator lines; wherein:
the blade holder link attachment root and the attachment root of the reaction link define with the second distal connecting portion of the support link a distal rotational joint for the blade holder link, the reaction link and the support link, so that the blade holder link, the reaction link and the support link are relatively rotatable about a common distal rotation axis, orthogonal to said common proximal rotation axis;
a counter-blade portion which is integral in rotation with said attachment root of the reaction link; and wherein said surgical cutting instrument further comprises:
a first pair of antagonistic tendons extending along the rod and connected to the blade holder link to move the blade link about said common distal rotation axis,
a second pair of antagonistic tendons extending along the rod and connected to said reaction link to move the counter-blade portion about said common distal rotation axis,
each tendon having a longitudinal extension; and wherein:
the attachment root of the blade holder link comprises in a single piece at least a first termination seat which receives said first pair of antagonistic tendons;
the attachment root of the reaction link comprises in a single piece at least a second termination seat which receives said second pair of antagonistic tendons; and wherein:
said one or more convex ruled surfaces with parallel generator lines of the connection link are parallel to said common proximal rotation axis;
at least one of said one or more convex ruled surfaces with parallel generator lines of the support link is parallel to said common proximal rotation axis;
said one or more convex ruled surfaces of blade holder root with parallel generator lines of the blade holder link and said one or more convex ruled surfaces of further root with parallel generator lines of the reaction link are parallel to the common distal rotation axis;
the first pair of antagonistic tendons and the second pair of antagonistic tendons are adapted to slide longitudinally on said one or more convex ruled surfaces of the connection link and on said one or more convex ruled surfaces of the support link and are adapted to wind/unwind without sliding on the respective convex ruled surface of the root of the blade holder link or of the reaction link, to move the blade link and the counter-blade portion respectively in opening/closing; and wherein
the cutting edge of the blade link is adapted to abut against said counter-blade portion during the movement of the degree of freedom of opening/closing in a mechanical interference contact condition to exert a cutting action;
the cutting edge of the blade link is elastically bendable in a direction parallel to the common distal rotation axis;

a first distance in a direction parallel to the common distal rotation axis between the first termination seat of the root of the blade holder link and a surface of said one or more convex ruled surfaces of the support link is constant for any cutting condition;

a second distance in a direction parallel to the common distal rotation axis between the second termination seat of the root of the reaction link and a surface of said one or more convex ruled surfaces of the support link is constant for any cutting condition.

2. The surgical instrument according to claim 1, wherein the overall sliding friction force exchanged between each tendon and all the ruled surfaces of the links on which the tendon slides, when in operating conditions, is much less than the tensile force transmitted by the same tendon to achieve the elastic bending deformation of the blade portion of the blade link when the degree of freedom of opening/closing is moved in closing to exert a cutting action.

3. The surgical instrument according to claim 1, wherein said distal rotational joint is a rigid rotational joint in an axial direction.

4. The surgical instrument according to claim 1, wherein all the convex ruled surfaces of the connection link, the support link, the pulley portion of the blade holder link and the pulley portion of the reaction link lack longitudinal channels.

5. The surgical instrument according to claim 1, wherein the attachment root of the blade holder link comprises a first surface facing axially outwards, and wherein the root of the reaction link comprises a second surface facing axially outwards, and wherein a distance in an axial direction between said first surface of the attachment root of the blade holder link and said second surface of the attachment root of the reaction link is constant for any cutting condition.

6. The surgical instrument according to claim 1, wherein the blade holder link comprises in a single piece a first cantilevered drag leg extending from the root of the blade holder link forming a free first leg end, said first cantilevered drag leg axially delimiting said first termination seat; and wherein the reaction link comprises in a single piece a second cantilevered drag leg extending from the root of the reaction link forming a free second leg end, said second cantilevered drag leg axially delimiting said second termination seat; and wherein said first and second cantilevered legs each comprise abutment and drag walls placed undercut with respect to the respective termination seats acting as dragging abutments for the respective tendon termination;

wherein a first distance in an axial direction between the first cantilevered leg of the blade holder link and a surface of said one or more convex ruled surfaces of the support link is constant for any cutting condition;

a second distance in a direction parallel to the common distal rotation axis between the second cantilevered leg and a surface of said one or more convex ruled surfaces of the support link is constant for any cutting condition.

7. The surgical instrument according to claim 1, wherein at least one of the blade holder link and the blade link comprises a free distal end in a single piece.

8. The surgical instrument according to claim 1, wherein the counter-blade portion protrudes axially internally.

9. The surgical instrument according to claim 1, further comprising a third pair of antagonistic tendons for moving the support link about said common proximal rotation axis with respect to the connection link;

wherein the support link comprises at least a third termination seat which receives the tendon terminations of said third pair of antagonistic tendons.

10. The surgical instrument according to claim 1, wherein the counter-blade portion protrudes axially internally, and comprises an internally curved protruding surface having a concavity facing axially inwards.

11. The surgical instrument according to claim 1, further comprising a third pair of antagonistic tendons for moving the support link about said common proximal rotation axis with respect to the connection link;

wherein the support link comprises at least a third termination seat which receives the tendon terminations of said third pair of antagonistic tendons; and wherein actuation tendons of said third pair of antagonistic tendons wind/unwind without longitudinally sliding on said one or more convex ruled surfaces of the support link, which act as pulley surfaces for the actuation tendons of the third pair of antagonistic tendons.

* * * * *